United States Patent
Collier et al.

(10) Patent No.: US 11,246,924 B2
(45) Date of Patent: Feb. 15, 2022

(54) ALPHA-HELICAL PEPTIDE NANOFIBERS AS A SELF-ADJUVANTING VACCINE PLATFORM

(71) Applicants: Duke University, Durham, NC (US); Emory University, Atlanta, GA (US)

(72) Inventors: Joel H. Collier, Durham, NC (US); Yaoying Wu, Durham, NC (US); Vincent P. Conticello, Atlanta, GA (US)

(73) Assignees: Duke University, Durham, NC (US); Emory University, Atlanta, GA (US)

( * ) Notice: Subject to any disclaimer, the term of this patent is extended or adjusted under 35 U.S.C. 154(b) by 480 days.

(21) Appl. No.: 16/090,561

(22) PCT Filed: Mar. 31, 2017

(86) PCT No.: PCT/US2017/025596
§ 371 (c)(1),
(2) Date: Oct. 1, 2018

(87) PCT Pub. No.: WO2017/173398
PCT Pub. Date: Oct. 5, 2017

(65) Prior Publication Data
US 2020/0390882 A1 Dec. 17, 2020

Related U.S. Application Data

(60) Provisional application No. 62/316,973, filed on Apr. 1, 2016.

(51) Int. Cl.
| A61K 38/00 | (2006.01) |
| A61K 39/00 | (2006.01) |
| A61K 39/385 | (2006.01) |
| A61K 47/64 | (2017.01) |
| A61K 38/05 | (2006.01) |
| A61K 39/39 | (2006.01) |
| C07K 14/71 | (2006.01) |

(52) U.S. Cl.
CPC ...... *A61K 39/39* (2013.01); *A61K 39/001104* (2018.08); *A61K 47/646* (2017.08); *C07K 14/71* (2013.01); *A61K 2039/55516* (2013.01); *A61K 2039/575* (2013.01); *A61K 2039/6031* (2013.01); *A61K 2039/64* (2013.01)

(58) Field of Classification Search
CPC . A61P 25/28; C07K 14/4711; C07K 5/06078; C07K 5/06165; C07K 5/0812
See application file for complete search history.

(56) References Cited

U.S. PATENT DOCUMENTS

| 4,338,298 A | 7/1982 | Myers |
| 4,367,110 A | 1/1983 | Yoshikawa |
| 4,452,901 A | 6/1984 | Gordon et al. |
| 4,554,101 A | 11/1985 | Hopp |
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,748,018 A | 5/1988 | Stolle et al. |
| 5,487,898 A | 1/1996 | Lu et al. |
| 5,512,282 A | 4/1996 | Krivan et al. |
| 5,548,066 A | 8/1996 | Leneau et al. |
| 5,580,859 A | 12/1996 | Felgner et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,302,874 B1 | 10/2001 | Zhang et al. |
| 6,651,655 B1 | 11/2003 | Licalsi et al. |
| 6,733,754 B2 | 5/2004 | Roberts et al. |
| 6,756,361 B1 | 6/2004 | Fattom et al. |
| 6,770,278 B1 | 8/2004 | Skelly |
| 6,793,923 B2 | 9/2004 | Brown et al. |
| 6,936,258 B1 | 8/2005 | Pavliak et al. |
| 7,664,545 B2 | 2/2010 | Westersten et al. |
| 2003/0165512 A1 | 9/2003 | Wheeler et al. |
| 2007/0087114 A1 | 4/2007 | Chilkoti et al. |
| 2009/0162437 A1 | 6/2009 | Horii et al. |
| 2010/0034896 A1 | 2/2010 | Tarasova et al. |
| 2014/0273148 A1* | 9/2014 | Collier et al. ......... C12N 11/06 435/177 |

FOREIGN PATENT DOCUMENTS

WO    WO 2017/173398 A1    10/2017

OTHER PUBLICATIONS

Egelman, E. et al., "Structural Plasticity of Helical Nanotubes based on coiled-coil assemblies", Structure, 2015, 23(2):280-289.*

(Continued)

*Primary Examiner* — Barry A Chestnut
(74) *Attorney, Agent, or Firm* — Michael Best & Friedrich LLP

(57) ABSTRACT

Embodiments are directed to fibrillar adjuvants. Epitopes assembled into nanofibers by a short synthetic fibrillization domain elicited high antibody titers in the absence of any adjuvant.

19 Claims, 31 Drawing Sheets

Specification includes a Sequence Listing.

(56) References Cited

OTHER PUBLICATIONS

Aggeli et al., "Responsive gels formed by the spontaneous self-assembly of peptides into polymeric beta-sheet tapes," Nature, 1997, 386:259-262.
Altunbas et al., "Encapsulation of curcumin in self-assembling peptide hydrogels as injectable drug delivery vehicles," Biomaterials, 2011, 32(25):5906-5914.
Bergquist et al., "Intranasal vaccination of humans with recombinant cholera toxin B subunit induces systemic and local antibody responses in the upper respiratory tract and the vagina," Infection and immunity, 1997, 65:2676-2684.
Bettahi et al., "Antitumor activity of a self-adjuvanting glycolipopeptide vaccine bearing B cell, CD4+ and CD8+ T cell epitopes," Cancer Immunol Immunother, 2009, 58:187-200.
Black et al., "Self-assembled peptide amphiphile micelles containing a cytotoxic T-cell epitope promote a protective immune response in vivo," Adv Mater, 2012, 24(28):3845-3849.
Boekhoven et al., "25th Anniversary article: supramolecular materials for regenerative medicine," Adv Mater, 2014, 26(11):1642-1659.
Bookstaver et al., "Improving Vaccine and Immunotherapy Design Using Biomaterials," Trends in immunology, 2018, 39(2):135-150.
Bowerman et al., "Review—Self-Assembly of Amphipathic β-Sheet Peptides: Insights and Applications," Peptide Science, 2012, 98(3):169-184.
Burkoth et al., "Self-assembly of αβ (10-35)-peg block copolymer fibrils," Journal of the American Chemical Society, 1999, 121:7429-7430.
C.T.F.A. Cosmetic Ingredient Handbook, 1992, pp. 587-592.
Cao et al., "Successful adjuvant-free vaccination of BALB/c mice with mutated amyloid β peptides," BMC Neurosci., 2008, 9:25.
Castelletto et al., "Self assembly of a model amphiphilic phenylalanine peptide/polyethylene glycol block copolymer in aqueous solution," Biophysical chemistry, 2009, 141:169-174.
Castelletto et al., "Self-assembly and bioactivity of a polymer/peptide conjugate containing the RGD cell adhesion motif and PEG," European Polymer Journal, 2013, 49:2961-2967.
Castelletto et al., "Self-assembly of PEGylated peptide conjugates containing a modified amyloid β-peptide fragment," Langmuir, 2010, 26:9986-9996.
Chen et al., "The use of self-adjuvanting nanofiber vaccines to elicit high-affinity B cell responses to peptide antigens without inflammation," Biomaterials, 2013, 34:8776-8785.
Chesson et al., "Antigenic peptide nanofibers elicit adjuvant-free CD8+ T cell responses," Vaccine, 2014, 32:1174-1180.
Choi et al., "EGFRvIII-targeted vaccination therapy of malignant glioma," Brain Pathol, 2009, 19(4):713-23.
Collier et al., "Enzymatic Modification of Self-Assembled Peptide Structures with Tissue Transglutaminase," Bioconjug. Chem., 2003, 14:748-755.
Collier et al., "Self-Assembling Polymer-Peptide Conjugates: Nanostructural Tailoring," Advanced Materials, 2004, 16:907-910.
Collier, "Modular self-assembling biomaterials for directing cellular responses," Soft Matter, 2008, 4:2310-2315.
Cong et al., "Identification of an immunodominant T cell epitope on cholera toxin," European journal of immunology, 1996, 26:2587-2594.
Çuburu et al., "Sublingual immunization induces broad-based systemic and mucosal immune responses in mice," Vaccine, 2007, 25:8598-8610.
Daftarian et al., "Eradication of established HPV 16-expressing tumors by a single administration of a vaccine composed of a liposome-encapsulated CTL-T helper fusion peptide in a water-in-oil emulsion," Vaccine, 2006, 24:5235-5244.
Davis et al., "Injectable self-assembling peptide nanofibers create intramyocardial microenvironments for endothelial cells," Circulation, 2005, 111:442-450.
Donnelly et al., "DNA vaccines," Ann. Rev. Immunol., 1997, 15:617-648.
Dowling et al., "Toll-like receptor 8 agonist nanoparticles mimic immunomodulating effects of the live BCG vaccine and enhance neonatal innate and adaptive immune responses," Journal of Allergy and Clinical Immunology, 2017, 140:1339-1350.
Dubois et al., "Self-assembling peptide nanofibers and skeletal myoblast transplantation in infarcted myocardium," J. Biomed. Mater. Res. B Appl. Biomater., 2008, 87:222-228.
Egelman et al., "Structural plasticity of helical nanotubes based on coiled-coil assemblies," Structure, 2015, 23:280-289.
Franklin, "Enzymes," Remington's Pharmaceutical Sciences, 15th Ed., 1990, Chapter 52, pp. 1035-1038.
Friedrich et al., "Supramolecular peptide hydrogel adjuvanted subunit vaccine elicits protective antibody responses against West Nile virus," Vaccine, 2016, 34(46):5479-5482.
Genove et al., "The effect of functionalized self-assembling peptide scaffolds on human aortic endothelial cell function," Biomaterials, 2005, 26:3341-3351.
Gras et al., "Functionalised amyloid fibrils for roles in cell adhesion," Biomaterials, 2008, 29:1553-1562.
Guler et al., "Presentation of RGDS Epitopes on Self-Assembled Nanofibers of Branched Peptide Amphiphiles," Biomacromolecules, 2006, 7:1855-1863.
Hamley et al., "Self-Assembly and Collagen-Stimulating Activity of a Peptide Amphiphile Incorporating a Peptide Sequence from Lumican," Langmuir, 2015, 31:4490-4495.
Hartgerink et al., "Self-assembly and mineralization of peptide-amphiphile nanofibers," Science, 2001, 294:1684-1688.
Hauri et al., "The global burden of disease attributable to contaminated injections given in health care settings," International journal of STD & AIDS, 2004, 15:7-16.
Heagerty et al., "Time-dependent ROC curves for censored survival data and a diagnostic marker," Biometrics, 2000, 56:337-44.
Heimberger et al., "Epidermal growth factor receptor VIII peptide vaccination is efficacious against established intracerebral tumors," Clin Cancer Res, 2003, 9(11):4247-4254.
Holmes et al., "Extensive neurite outgrowth and active synapse formation on self-assembling peptide scaffolds," Proc. Natl. Acad. Sci. USA, 2000, 97:6728-6733.
Horii et al., "Biological Designer Self-Assembling Peptide Nanofiber Scaffolds Significantly Enhance Osteoblast Proliferation, Differentiation and 3-D Migration," PLoS ONE, 2007, 2:e190.
Hotaling et al., "Biomaterial strategies for immunomodulation," Annual review of biomedical engineering, 2015, 17:317-349.
Hsieh et al., "Controlled delivery of PDGF-BB for myocardial protection using injectable self-assembling peptide nanofibers," J. Clin. Invest., 2006, 116:237-248.
Huang, "A totally synthetic, self-assembling, adjuvant-free MUC1 glycopeptide vaccine for cancer therapy," Journal of the American Chemical Society, 2012, 134(21):8730-8733. Supporting Information S1-S27.
Huebener et al., "Vaccination with minigenes encoding for novel 'self' antigens are effective in DNA-vaccination against neuroblastoma," Cancer Lett, 2003, 197(1-2): 211-217.
International Search Report and Written Opinion for Application No. PCT/US2017/025596 dated Jul. 21, 2017 (10 pages).
International Search Report and Written Opinion for Application No. PCT/US2018/042762 dated Oct. 17, 2018 (13 pages).
Ishii et al., "Toll or toll-free adjuvant path toward the optimal vaccine development," J Clin Immunol, J. Clin. Immunol., 2007, 27:363-371.
Jung et al., "Co-assembling peptides as defined matrices for endothelial cells," Biomaterials, 2009, 30:2400-2410.
Jung et al., "Modulating the mechanical properties of self-assembled peptide hydrogels via native chemical ligation," Biomaterials, 2008, 29:2143-2151.
Kalafatovic et al., "MMP-9 triggered self-assembly of doxorubicin nanofiber depots halts tumor growth," Biomaterials, 2016, 98, 192-202.
Kelly et al., "Biomaterial strategies for generating therapeutic immune responses," Advanced drug delivery reviews, 2017, 114:3-18.
Kraan et al., "Buccal and sublingual vaccine delivery," Journal of controlled release, 2014, 190:580-592.

(56) References Cited

OTHER PUBLICATIONS

Krysmann et al., "Self-assembly and hydrogelation of an amyloid peptide fragment," Biochemistry, 2008, 47:4597-4605.
Kuai et al., "Designer vaccine nanodiscs for personalized cancer immunotherapy," Nature materials, 2017, 16:489-498.
Kyte et al., "A simple method for displaying the hydropathic character of a protein," J. Mol. Biol., 1982, 157:105-132.
Lai et al., "Micro- and macrorheology of mucus," Advanced drug delivery reviews, 2009, 61:86-100.
Lai et al., "Mucus-penetrating nanoparticles for drug and gene delivery to mucosal tissues," Advanced drug delivery reviews, 2009, 61:158-171.
Lai et al., "Nanoparticles reveal that human cervicovaginal mucus is riddled with pores larger than viruses," Proceedings of the National Academy of Sciences, 2010, 107:598-603.
Lambrecht et al., "Mechanism of action of clinically approved adjuvants," Curr. Opin. Immunol., 2009, 21:23-29.
Law et al., "Protease-sensitive fluorescent nanofibers," Bioconjugate chemistry, 2007, 18:1701-1704.
Li et al., "Missing tooth multidomain peptide nanofibers for delivery of small molecule drugs," Biomacromolecules, 2016, 17(6):2087-2095.
Loo et al., "Self-assembled proteins and peptides as scaffolds fortissue regeneration," Advanced Healthcare Materials, 2015, 4(16):2557-2586.
Lutolf et al., "Synthetic biomaterials as instructive extracellular microenvironments for morphogenesis in tissue engineering," Nat. Biotechnol., 2005, 23:47-55.
Lycke, "Recent progress in mucosal vaccine development: potential and limitations," Nature Reviews Immunology, 2012, 12:592-605.
Maraskovsky et al., "Development of prophylactic and therapeutic vaccines using the ISCOMATRIX adjuvant," Immunol. Cell Biol., 2009, 87:371-376.
Marrack et al., "Towards an understanding of the adjuvant action of aluminium," Nat. Rev. Immunol., 2009, 9:287-293.
Matoba, "N-Glycosylation of Cholera Toxin B Subunit: Serendipity for Novel Plant-Made Vaccines?," Frontiers in plant science, 2015, 6:1132, 7 pages.
McCutcheon's vol. 1, Emulsifiers & Detergents, 1994, North American Edition, pp. 236-239.
McKee et al., "How do adjuvants work? Important considerations for new generation adjuvants," Immunity, 2007, 27:687-690.
McSorley et al., "Bacterial Flagellin Is an Effective Adjuvant for CD4* T Cells In Vivo," J. Immunol., 2002, 169:3914-3919.
Merrifield, "Solid Phase Peptide Synthesis. I. The Synthesis of a Tetrapeptide," J. Am. Chem. Soc., 1963, 85:2149-2156.
Monteverde et al., "The relevance of ADCC for EGFR targeting: a review of the literature and a clinically-applicable method of assessment in patients," Crit Rev Oncol Hematol, 2015, 95(2):179-190.
Moon et al., "Interbilayer-crosslinked multilamellar vesicles as synthetic vaccines for potent humoral and cellular immune responses," Nature materials, 2011, 10:243-251.
Mora-Solano et al., "Active immunotherapy for TNF-mediated inflammation using self-assembled peptide nanofibers," Biomaterials, 2017, 149:1-11.
Mueller et al., "Rapid and persistent delivery of antigen by lymph node targeting PRINT nanoparticle vaccine carrier to promote humoral immunity," Molecular pharmaceutics, 2015, 12:1356-1365.
Neutra et al., "Mucosal vaccines: the promise and the challenge," Nature reviews immunology, 2006, 6:148-158.
Oberoi et al., "PEG modified liposomes containing CRX-601 adjuvant in combination with methylglycol chitosan enhance the murine sublingual immune response to influenza vaccination," Journal of Controlled Release, 2016, 223:64-74.
Place et al., "Complexity in biomaterials fortissue engineering," Nat. Mater., 2009, 8:457-470.

Pompano et al., "Titrating T-cell epitopes within self-assembled vaccines optimizes CD4+ helper T cell and antibody outputs," Advanced Healthcare Materials, 2014, 3:1898-908.
Purcell et al., "More than one reason to rethink the use of peptides in vaccine design," Nat. Rev. Drug Discov., 2007, 6:404-414.
Remington's Pharmaceutical Sciences, 15th Ed. 1975, pp. 335-337.
Riley et al., "Bioproduction and characterization of a pH responsive self-assembling peptide," Biotechnol. Bioeng., 2009, 103:241-251.
Rincon-Restrepo et al., "Vaccine nanocarriers: Coupling intracellular pathways and cellular biodistribution to control CD4 vs CD8 T cell responses," Biomaterials, 2017, 132:48-58.
Rudra et al., "A combined carrier-adjuvant system of peptide nanofibers and toll-like receptor agonists potentiates robust CD8+ T cell responses," Vaccine, 2018, 36:438-441.
Rudra et al., "A self-assembling peptide acting as an immune adjuvant," Proceedings of the National Academy of Sciences, 2010, 107:622-627.
Rudra et al., "Modulating adaptive immune responses to peptide self-assemblies," ACS Nano, 2012, 6:1557-1564.
Rudra et al., "Self-assembled peptide nanofibers raising durable antibody responses against a malaria epitope," Biomaterials, 2012, 33:6476-6484.
Sampson et al., "An epidermal growth factor receptor variant III-targeted vaccine is safe and immunogenic in patients with glioblastoma multiforme," Mol Cancer Ther, 2009, 8(10):2773-9.
Schneider et al., "Responsive hydrogels from the intramolecular folding and self-assembly of a designed peptide," J. Am. Chem. Soc., 2002, 124:15030-15037.
Scott et al., "Antibody therapy of cancer," Nat Rev Cancer, 2012, 12:278-287.
Seth et al., "Modular virus-like particles for sublingual vaccination against group A *Streptococcus*," Vaccine, 2016, 34:6472-6480.
Shakya et al., "Mucosal vaccine delivery: current state and a pediatric perspective," Journal of Controlled Release, 2016, 240:394-413.
Shen et al., "The future of routine immunization in the developing world: challenges and opportunities," Global Health: Science and Practice, 2014, 2:381-394.
Si et al., "Intranasal delivery of adjuvant-free peptide nanofibers elicits resident CD8+ T cell responses," Journal of Controlled Release, 2018, 282:120-130.
Silva et al., "Selective differentiation of neural progenitor cells by high-epitope density nanofibers," Science, 2004, 303:1352-1355.
Snapper et al., "Towards a comprehensive view of immunoglobulin class switching," Immunol Today, 1993, 14(1):15-17.
Song J-H et al., "Sublingual vaccination with influenza virus protects mice against lethal viral infection," Proceedings of the National Academy of Sciences, 2008, 105:1644-1649.
Spinner et al., "Methylglycol chitosan and a synthetic TLR4 agonist enhance immune responses to influenza vaccine administered sublingually," Vaccine, 2015, 33:5845-5853.
Stratmann, "Cholera toxin subunit B as adjuvant—An accelerator in protective immunity and a break in autoimmunity," Vaccines, 2015, 3:579-596.
Sun et al., "Advances in saponin-based adjuvants," Vaccine, 2009, 27:1787-1796.
Tang et al., "Biodegradable polymer nanoparticles that rapidly penetrate the human mucus barrier," Proceedings of the National Academy of Sciences, 2009, 106:19268-19273.
Teubl et al., "The effect of saliva on the fate of nanoparticles," Clinical oral investigations, 2018, 22:929-940.
Thiyagarajan et al., "pH dependent self assembly of β-amyloid (10-35) and β-amyloid (10-35)-PEG3000," Journal of applied crystallography, 2000, 33:535-539.
Toth et al., "Recent advances in design and synthesis of self-adjuvanting lipopeptide vaccines," Int. J. Pept. Res. Ther., 2008, 14:333-340.
Trent et al., "Peptide amphiphile micelles self-adjuvant group A *Streptococcal* vaccination," The AAPS journal, 2015, 17:380-388.
Turco, "Intravenous Admixtures," Remington's Pharmaceutical Sciences, 15th Ed., Chapter 85, 1990, pp. 1570-1580.

(56) References Cited

OTHER PUBLICATIONS

Turecek et al., "PEGylation of Biopharmaceuticals: A Review of Chemistry and Nonclinical Safety Information of Approved Drugs," Journal of Pharmaceutical Sciences, 2016, 105:460-475.

Tysseling-Mattiace et al., "Self-assembling nanofibers inhibit glial scar formation and promote axon elongation after spinal cord injury," J. Neurosci., 2008, 28:3814-3823.

Ustun Yaylaci et al., "Supramolecular GAG-like self-assembled glycopeptide nanofibers induce chondrogenesis and cartilage regeneration," Biomacromolecules, 2016, 17(2):679-689.

Wagh et al., "A short circulating peptide nanofiber as a carrier for tumoral delivery," Nanomedicine: Nanotechnology, Biology and Medicine, 2013, 9:449-457.

Webber et al., "Development of bioactive peptide amphiphiles for therapeutic cell delivery," Acta Biomater., 2010, 6(1):3-11.

Webber et al., "Supramolecular biomaterials," Nat Mater, 2016, 15(1):13-26.

Wen et al., "Switching the Immunogenicity of Peptide Assemblies Using Surface Properties," ACS Nano, 2016, 10(10):9274-9286.

Wendorf et al., "A practical approach to the use of nanoparticles for vaccine delivery," J. Pharm. Sci., 2006, 95:2738-2750.

Wilson et al., "pH-Responsive nanoparticle vaccines for dual-delivery of antigens and immunostimulatory oligonucleotides," ACS nano, 2013, 7:3912-3925.

Woodrow et al., "Mucosal vaccine design and delivery," Annual review of biomedical engineering, 2012, 14:17-46.

Wu et al., "A Supramolecular Vaccine Platform Based on α-Helical Peptide Nanofibers," ACS Biomaterials Science & Engineering, 2017, 3:3128-3132.

Wu et al., "Alpha-helical peptide nanofibers as a self-adjuvanting vaccine plataform," Frontiers in Bioengineering and Biotechnol. Conference Abstract, 10th World Biomaterials Congress, 2016.

Xu et al., "Impact of surface polyethylene glycol (PEG) density on biodegradable nanoparticle transport in mucus ex vivo and distribution in vivo," ACS nano, 2015, 9:9217-9227.

Yang et al., "Novel T-cell epitopes of ovalbumin in BALB/c mouse: potential for peptide-immunotherapy," Biochem. Biophys. Res. Commun., 2009, 378:203-208.

Yuba et al., "pH-Responsive Micelle-Based Cytoplasmic Delivery System for Induction of Cellular Immunity," Vaccines, 2017, 5:41, 14 pages.

Zeng et al., "Advanced manufacturing of microdisk vaccines for uniform control of material properties and immune cell function," Biomaterials science, 2018, 6:115-124.

Zhang et al., "Self-assembled Tat nanofibers as effective drug carrier and transporter," ACS Nano, 2013, 7(7):5965-5977.

Zhou et al., "Self-assembled peptide-based hydrogels as scaffolds for anchorage-dependent cells," Biomaterials, 2009, 30:2523-2530.

\* cited by examiner

FIG. 5A-B

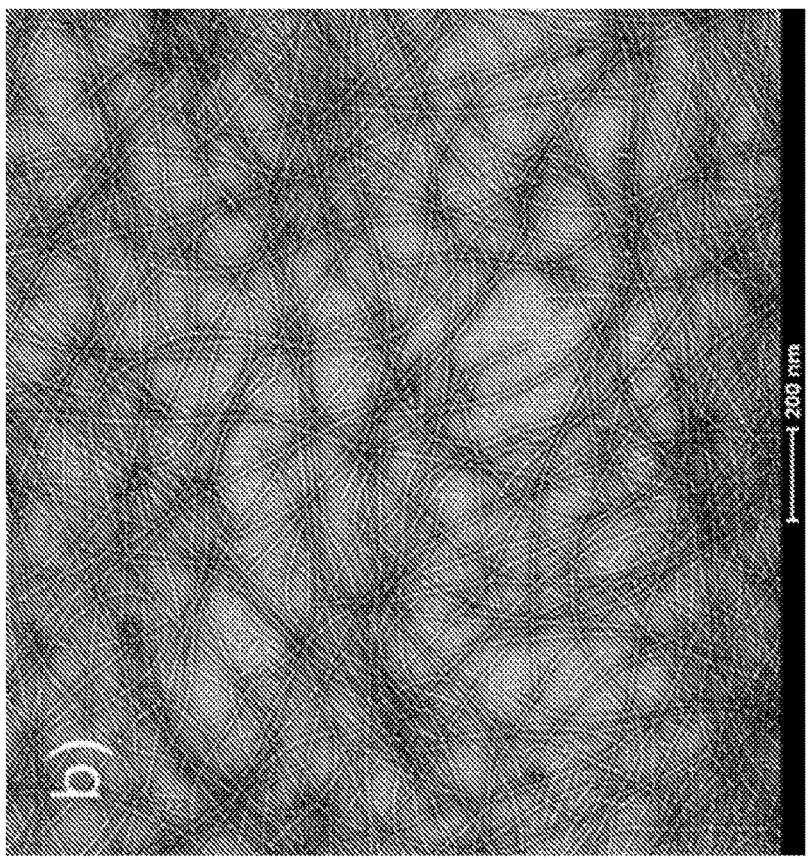
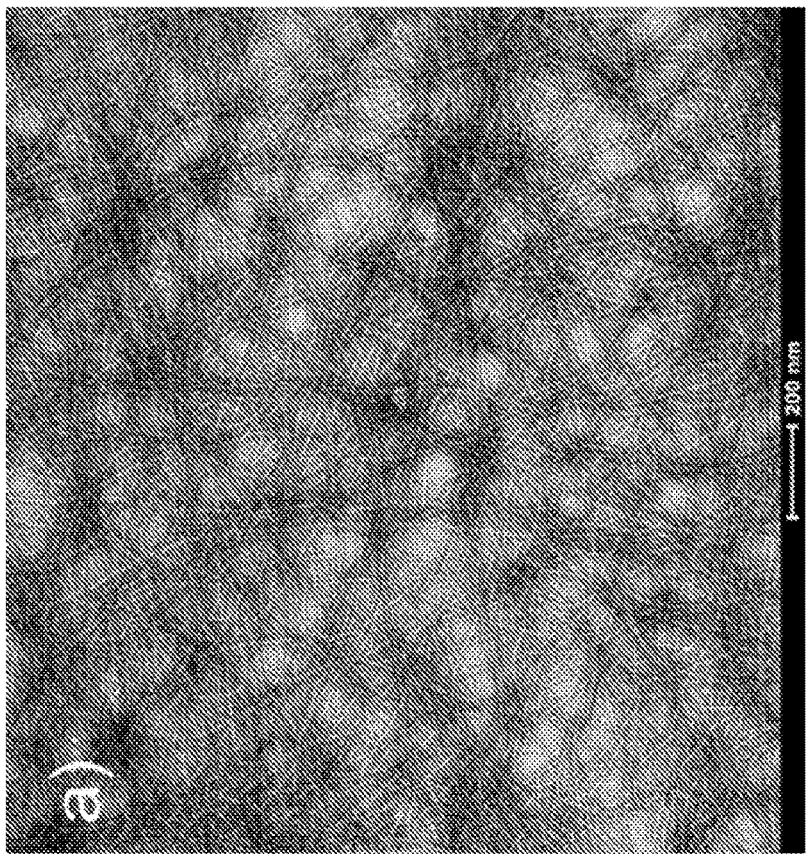
FIG. 12

ALPHA-HELICAL PEPTIDE NANOFIBERS AS A SELF-ADJUVANTING VACCINE PLATFORM

CROSS-REFERENCE TO RELATED APPLICATIONS

This application is the U.S. national stage entry, under 35 U.S.C. 371, of international application number PCT/US2017/025596, filed Mar. 31, 2017, which claims priority to U.S. Provisional Patent Application No. 62/316,973, filed Apr. 1, 2016, the entire contents of which are incorporated herein by reference.

STATEMENT REGARDING FEDERALLY SPONSORED RESEARCH

This invention was made with government support under grant R01EB009701 awarded by the National Institutes of Health. The government has certain rights in the invention.

SEQUENCE LISTING

The sequence listing is filed with the application in electronic format only and is incorporated by reference herein. The sequence listing text file "028193-9266-US02_As_Filed_Sequence_Listing" was created on Sep. 27, 2018 and is 7,490 bytes in size.

FIELD

Embodiments of this invention are directed generally to biology, medicine, and immunology. Certain aspects are directed to immunogenic fibrils and their use in inducing an immune response.

INTRODUCTION

The development of vaccines and other immunotherapies has been challenged by imprecise antigen display and the use of heterogeneous immune adjuvants whose mechanisms of action are complex and incompletely understood. Synthetic peptides are useful as antigens because their precise chemical definition allows one to specify the exact epitopes against which an immune response is to be raised. However, peptides are poorly immunogenic by themselves and require co-administration with strong adjuvants, a process that sacrifices the chemical definition that peptides possess initially and complicates their development and regulatory approval. Although several adjuvants have been investigated for peptide immunotherapies to date, current strategies such as particulates, oil emulsions, toll-like receptor ligands, ISCOMs, and other biologically sourced materials utilize chemically or structurally heterogeneous materials, making characterization and mechanistic understanding challenging. This situation has motivated the pursuit of self-adjuvanting or adjuvant-free systems).

Peptide self-assembly has been previously explored for biomaterials applications, including cell delivery, drug delivery, and vaccine platforms. It has been previously demonstrated that epitope-bearing β-sheet fibrillizing peptides can elicit strong and specific antibody responses without supplemental immune adjuvants, making them an attractive platforms for vaccine development. However, β-sheet fibrillizing peptides lack structural precision, and the kinetics of their assembly and disassembly are difficult to control. In most cases immunization results in antibody responses that last for the lifetime of the subject, which may not be desirable for some applications, such as acute treatments or for targets that may include self-epitopes. Furthermore, the toxicity profile of β-sheet nanofibers is incompletely understood. Some β-sheet nanofibers are considerably cytotoxic and neurotoxic, while others are not, and the structural determinants of this toxicity are not well understood. There remains a need for additional immunogenic compositions to induce immune responses for treating microbial infection and other pathogenic conditions such as cancer and autoimmunity.

SUMMARY

In an aspect, provided herein is an immunogenic composition including a peptide fibril coupled to a plurality of antigens, wherein the peptide fibril comprises a plurality of alpha helices. In some embodiments, the peptide fibril comprises a plurality of self-assembling peptides, wherein each self-assembling peptide forms an alpha-helix. In some embodiments, the peptide fibril has a coiled coil structure. In some embodiments, the peptide fibril has a structure of a helical filament formed around a central axis. In some embodiments, the N-terminus of each self-assembling peptide is positioned at the exterior of the helical filament. In some embodiments, the self-assembling peptide is conjugated to an antigen. In some embodiments, each self-assembling peptide is conjugated to an antigen. In some embodiments, the antigen is covalently coupled to the self-assembling peptide. In some embodiments, the antigen is covalently coupled to a terminus of the self-assembling peptide. In some embodiments, the antigen is covalently coupled to the N-terminus of the self-assembling peptide. In some embodiments, the antigens are exposed on the exterior surface of the peptide fibril. In some embodiments, the antigens are exposed on the exterior surface of the helical filament of the peptide fibril. In some embodiments, wherein the antigen is selected from a small molecule, nucleotide, polynucleotide, peptide, polypeptide, protein, lipid, carbohydrate, and a combination thereof. In some embodiments, the antigen comprises a peptide. In some embodiments, the peptide is 5 to 35 amino acids in length. In some embodiments, the antigen is comprises a small molecule. In some embodiments, the antigen is comprises a cytokine. In some embodiments, the peptide fibril comprises at least two different antigens. In some embodiments, the peptide fibril comprises self-assembling peptides not conjugated to the antigen and self-assembling peptides conjugated to the antigen, and wherein the peptide fibril comprises at least two different antigens. In some embodiments, the plurality of antigens comprises a B cell epitope, or T cell epitope, or a combination thereof. In some embodiments, the plurality of antigens comprises a B cell epitope and a T cell epitope. In some embodiments, the peptide fibril is non-toxic. In some embodiments, the self-assembling peptide comprises an amino acid sequence of bXXXb (SEQ ID NO: 1), wherein X is independently any amino acid, and b is independently any positively charged amino acid. In some embodiments, b is independently selected from Arg and Lys. In some embodiments, b is Arg. In some embodiments, bXXXb (SEQ ID NO: 1) is RAYAR (SEQ ID NO: 2). In some embodiments, bXXXb (SEQ ID NO: 1) is KAYAK (SEQ ID NO: 3). In some embodiments, the self-assembling peptide comprises an amino acid sequence of $Z_n bXXXbZ_m$ (SEQ ID NO: 5), wherein b is independently any positively charged amino acid, Z is independently any amino acid, X is independently any amino acid, n is an integer from 0 to 20, and m is an integer from 0 to 20. In some embodiments, n is an integer from 5 to 15, and m is an integer from 5 to 15. In some embodiments, the self-assembling peptide comprises a glutamine at the C-terminus. In some embodiments, the self-assembling peptide comprises a glutamine at the N-terminus. In some embodiments, the self-assembling peptide comprises an amino acid sequence selected from QARILEADAEILRAYARILEAHAEILRAQ (SEQ ID NO: 6), or QAKILEADAEILKAYAKILEAHAEILKAQ (SEQ ID NO: 7), or ADAEILRAYARILEAHAEILRAQ (SEQ ID NO: 8). In some embodiments, the self-assembling peptide comprises an amino acid sequence of QARILEADAEILRAYARILEAHAEILRAQ (SEQ ID NO: 6). In some embodiments, the self-assembling peptide comprises an amino acid sequence of QAKILEADAEILKAYAKILEAHAEILKAQ (SEQ ID NO: 7). In some embodiments, the self-assembling peptide comprises an amino acid sequence of ADAEILRAYARILEAHAEILRAQ (SEQ ID NO: 8). In some embodiments, the self-assembling peptide further comprises a linker between the antigen and self-assembling peptide. In some embodiments, the linker comprises oligoethylene glycol, polyethylene glycol, or an amino acid sequence selected from SEQ ID NO: 9 ($G_n$, wherein n is an integer from 1 to 10), SEQ ID NO: 10 (SGSG), SEQ ID NO: 11 (GSGS), SEQ ID NO: 12 (SSSS), SEQ ID NO: 13 (GGGS), SEQ ID NO: 14 (GGC), SEQ ID NO: 15 ($(GGC)_8$), and SEQ ID NO: 16 ($(G_4S)_3$). In some embodiments, wherein the antigen is attached to the self-assembling peptide through a thiol reactive group in the linker. In some embodiments, the peptide fibril is at least 250 nanometers in length. In some embodiments, the composition further comprises an adjuvant. In some embodiments, the composition does not further comprise an adjuvant. In some embodiments, the peptide fibril is an adjuvant. In some embodiments, the self-assembling peptide is synthesized by a solid phase peptide synthesis.

In another aspect, provided herein is a method of inducing an antigen-specific immune response in a subject comprising administering to the subject the immunogenic composition as detailed herein in an amount sufficient to induce an immune response and antigen-specific immunity. In some embodiments, the immunogenic composition is administered to the subject intravenously, intraarterially, intraperitoneally, subcutaneously, intranasally, intramuscularly, or intratumorally. In some embodiments, the immune response is an antigen-specific immune response. In some embodiments, the antigen-specific immune response is temporary or not life-long. In some embodiments, the immune response comprises IgG1 antibody isotypes. In some embodiments, the immunogenic composition has increased immunogenicity relative to a control. In some embodiments, the control comprises the antigen without a self-assembling peptide. In some embodiments, the subject has cancer. In some embodiments, the immune response is an anti-cancer immune response. Further provided herein is an antibody produced in the immune response by a method as detailed herein.

In another aspect, provided is a method of treating a subject having or at risk of developing a microbial infection or pathological condition comprising administering to the subject an effective amount of a composition as detailed herein or the antibody as detailed herein. In some embodiments, the pathological condition is cancer or autoimmunity.

In a further aspect, provided is a method for making the composition as detailed herein, the method comprising: providing a first peptide fibril comprising self-assembling peptides conjugated to a first antigen; providing a second peptide fibril comprising self-assembling peptides conjugated to a second antigen; and mixing together the first and the second peptide fibrils.

In a further aspect, provided is a method for making the composition as detailed herein, the method comprising: providing a first peptide fibril comprising self-assembling peptides conjugated to an antigen; providing a second peptide fibril comprising self-assembling peptides not conjugated to an antigen; and mixing together the first and the second peptide fibrils.

In a further aspect, provided is a method for making the composition as detailed herein, the method comprising: providing a first peptide fibril comprising self-assembling peptides conjugated to a first antigen; providing a second peptide fibril comprising self-assembling peptides conjugated to a second antigen; providing a third peptide fibril comprising self-assembling peptides not conjugated to an antigen; and mixing together the first, the second, and the third peptide fibrils.

In a further aspect, provided is a method for making the composition as detailed herein, the method comprising: providing a first mixture comprising a plurality of self-assembling peptides, each self-assembling peptide conjugated to a first antigen; providing a second mixture comprising a plurality of self-assembling peptides, each self-assembling peptide conjugated to a second antigen; and mixing together the first mixture and the second mixture to form peptide fibrils, each peptide fibril comprising the first and second antigen.

In a further aspect, provided is a method for making the composition as detailed herein, the method comprising: providing a first mixture comprising a plurality of self-assembling peptides conjugated to an antigen; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen.

In a further aspect, provided is a method for making the composition as detailed herein, the method comprising: providing a first mixture comprising a plurality of self-assembling peptides conjugated to a first antigen; providing a second mixture comprising a plurality of self-assembling peptides conjugated to a second antigen; providing a third mixture comprising a plurality of self-assembling peptides not conjugated to an antigen; and mixing together the first, the second, and the third mixtures to form peptide fibrils, each peptide fibril comprising the first antigen, the second antigen, and a portion of the self-assembling peptides not conjugated to an antigen. In some embodiments, the first and second antigens are different.

In a further aspect, provided is a method for making the composition as detailed herein, the method comprising: providing a first mixture comprising a plurality of self-assembling peptides conjugated to one or more antigens; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen. In some embodiments, the antigens are the same. In some embodiments, the antigens are different. In some embodiments, the peptide fibril comprises n different antigens, wherein n is an integer from 1 to 10,000.

The disclosure provides for other aspects and embodiments that will be apparent in light of the following detailed description and accompanying figures.

BRIEF DESCRIPTION OF THE DRAWINGS

(FIG. 2E) Secondary structure of Coil29 and its derivative peptide, indicating alpha helical structure.

(FIG. 7A) Coil29 peptide self-assembled into high aspect ratio fibers characterized by TEM. (FIG. 7B) Epitope bearing nanofiber formed by PEPvIII-Coil29 alone exhibited similar morphology to Coil29 peptide fiber. (FIG. 7C) PEPvIII-Coil29 and PADRE-Coil29 co-assembled into fibers with a molar ratio of 20:1. (FIG. 7D) PADRE-Coil29 peptide self-assembled into relatively short fiber fragments. (FIG. 7E) Peptide nanofiber formed with SIINFEKL-Coil29 (FIG. 7F) Alpha-helical secondary structure is preserved in all the fiber formulation as evidenced by the characteristic peaks in circular dichroism spectra (all scale bars: 100 nm).

(FIG. 8A) Representative figures of the TAMRA positive dendritic cells (DC) and macrophages 20 h after i.p. injections of TAMRA-PEPvIII or TAMRA-PEPvIII-Coil29. (FIG. 8B) A significantly larger fraction of both DCs and Macrophages picked up labeled nanofibers as compared to labeled soluble epitopes. (N=5 mice per group, $p<0.05$, analyzed by two-way ANOVA for multiple comparison.

(FIG. 9A) Mice of all four groups were given a primary injection ($2\times10^{-3}$ M of PEPvIII epitopes, 100 μL per mouse) on week 0, followed by two boost injections ($2\times10^{-3}$ M of PEPvIII epitopes, 50 μL per mouse) on week 4 and 7 for all four groups. (N=5 mice per group, $p<0.05$, analyzed by two-way ANOVA for multiple comparison. * represents significant difference compared with both PEPvIII and P—C groups; ** represents significant difference compared with all other groups). (FIG. 9B) Antibody isotype distribution of PEPvIII-specific antibodies in sera from mice immunized by PEPvIII peptide with CFA adjuvant (left panel), and P-C/P co-assembled peptide fibers (right panel). Each point represents one mouse; bar graph represents the mean value and standard deviation. (N=5 mice per group, $p<0.05$, analyzed by two-way ANOVA for multiple comparison.)

(FIG. 10A) Increasing PADRE epitopes doses led to sustained higher titers of epitope-specific antibody production over 17 weeks. (N=5 mice per group, $p<0.05$, analyzed by two-way ANOVA for multiple comparison. * represents significant difference compared with PEPvIII group). (FIG. 10B) Total IgG titer elevated gradually as PADRE epitope dosing increased on the week after boost injections. (N=5 mice per group, $p<0.05$, analyzed by two-way ANOVA for multiple comparison. * represents significant difference compared with PEPvIII group). (FIG. 10C) The higher T cell IL-4 and IFNγ responses were elicited against higher PADRE epitope dosing regime, according to ELISPOT assays (splenocytes collected on week 18).

(FIG. 11A) Representative figures of the SIINFEKL/MHC-I positive DC 20 h after i.p. injections of SIINFEKL/Alum, SIINFEKL-Coil29, or SIINFEKL-Q11. (FIG. 11B) Quantitative summary of the SIINFEKL (SEQ ID NO: 23) presentation in DCs. SIINFEKL-Coil29 immunization led to a significantly larger proportion of SIINFEKL presenting DCs compared with SIINFEKL-Q11 and SIINFEKL/Alum (N=3 mice per group, $p<0.05$, analyzed by two-way ANOVA for multiple comparison). (FIG. 11C) Splenocytes harvested from mice immunized with SIINFEKL/Alum, SIINFEKL-Coil29, or SIINFEKL-Q11 exhibited comparable IFNγ responses when restimulated with SIINFEKL peptide. (#statistically insignificant, N=12 mice per group, analyzed by two-way ANOVA for multiple comparison.)

FIG. 12A-12B: Comparison of Coil29 and Q11. TEM images of (FIG. 12A) OVA-Coil29|Coil29 (1|2) nanofibers and (FIG. 12B) OVA-Q11|Q11 (1|2).

(FIG. 16A) $NH_2$—PEPvIII, (FIG. 16B) $NH_2$—PADRE, (FIG. 16C) Biotin-PEPvIII, (FIG. 16D) Coil29, (FIG. 16E) Biotin-SGSG Coil29, (FIG. 16F) PEPvIII-Coil29, (FIG. 16G) PADRE-Coil29.

(FIG. 17A) TAMRA-PEPvIII-Coil29. (FIG. 17B) PEPvIII-Coil29.

DETAILED DESCRIPTION

Figure 1A:
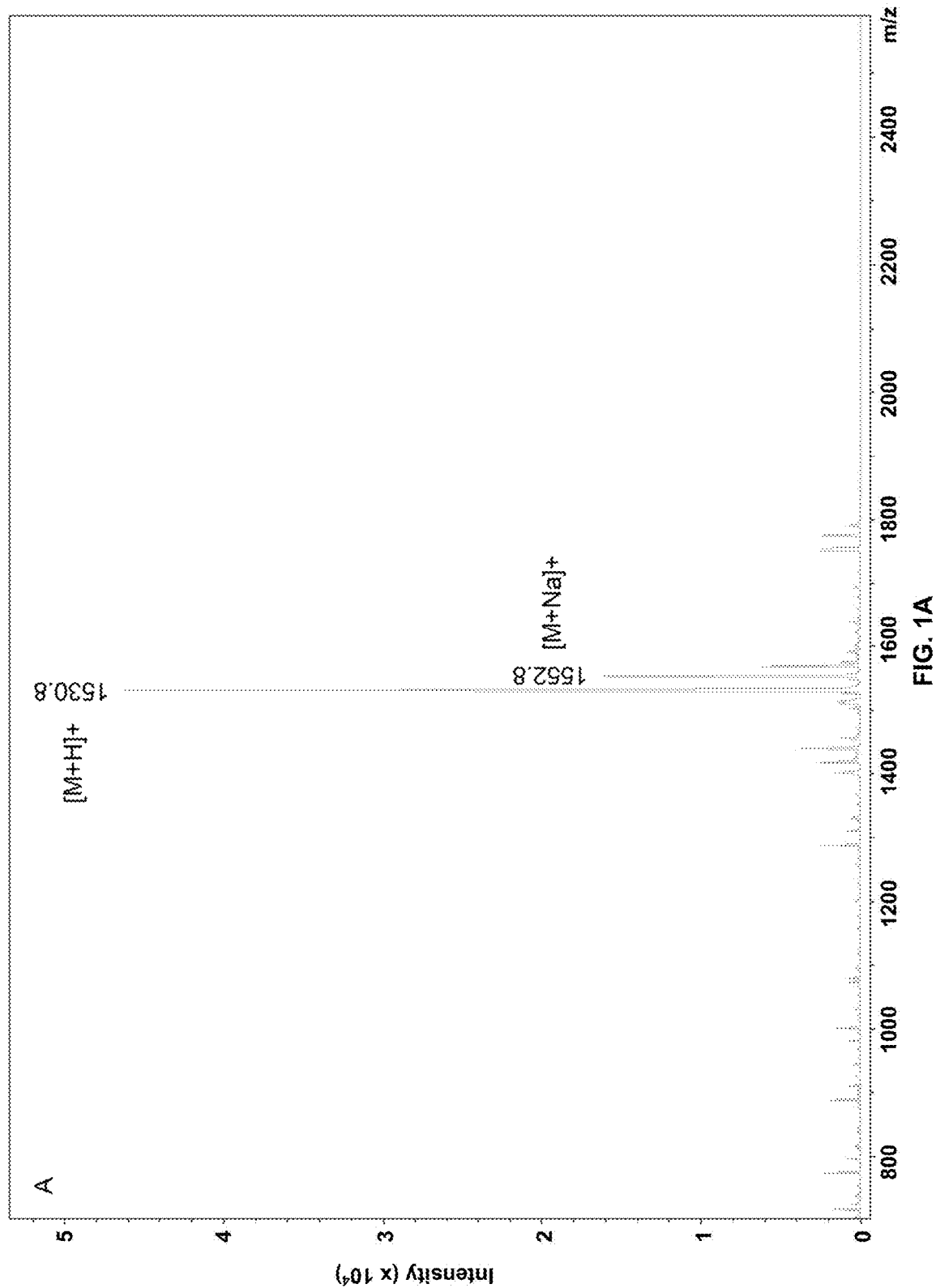
FIGS. 1A-1G: MALDI-TOF mass spectrometry for purified peptides, (FIG. 1A) NH2-PEPvIII, (FIG. 1B) NH2-PADRE, (FIG. 1C) Biotin-PEPvIII, (FIG. 1D) coil29, (FIG. 1E) Biotin-SGSG coil29, (FIG. 1F) PEPvIII-coil29, and (FIG. 1G) PADRE-coil29.
Figure 1B:
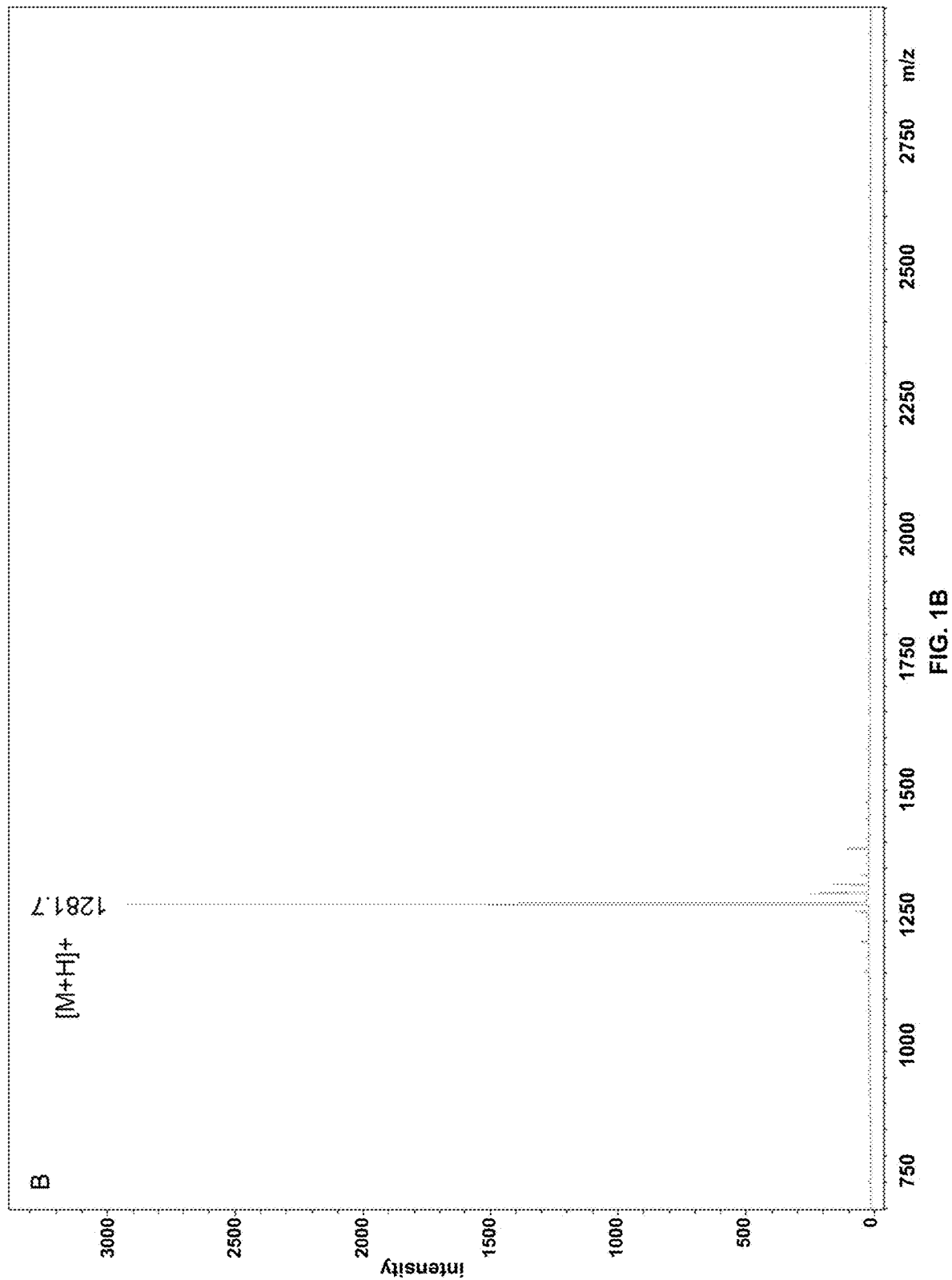
Figure 1C:
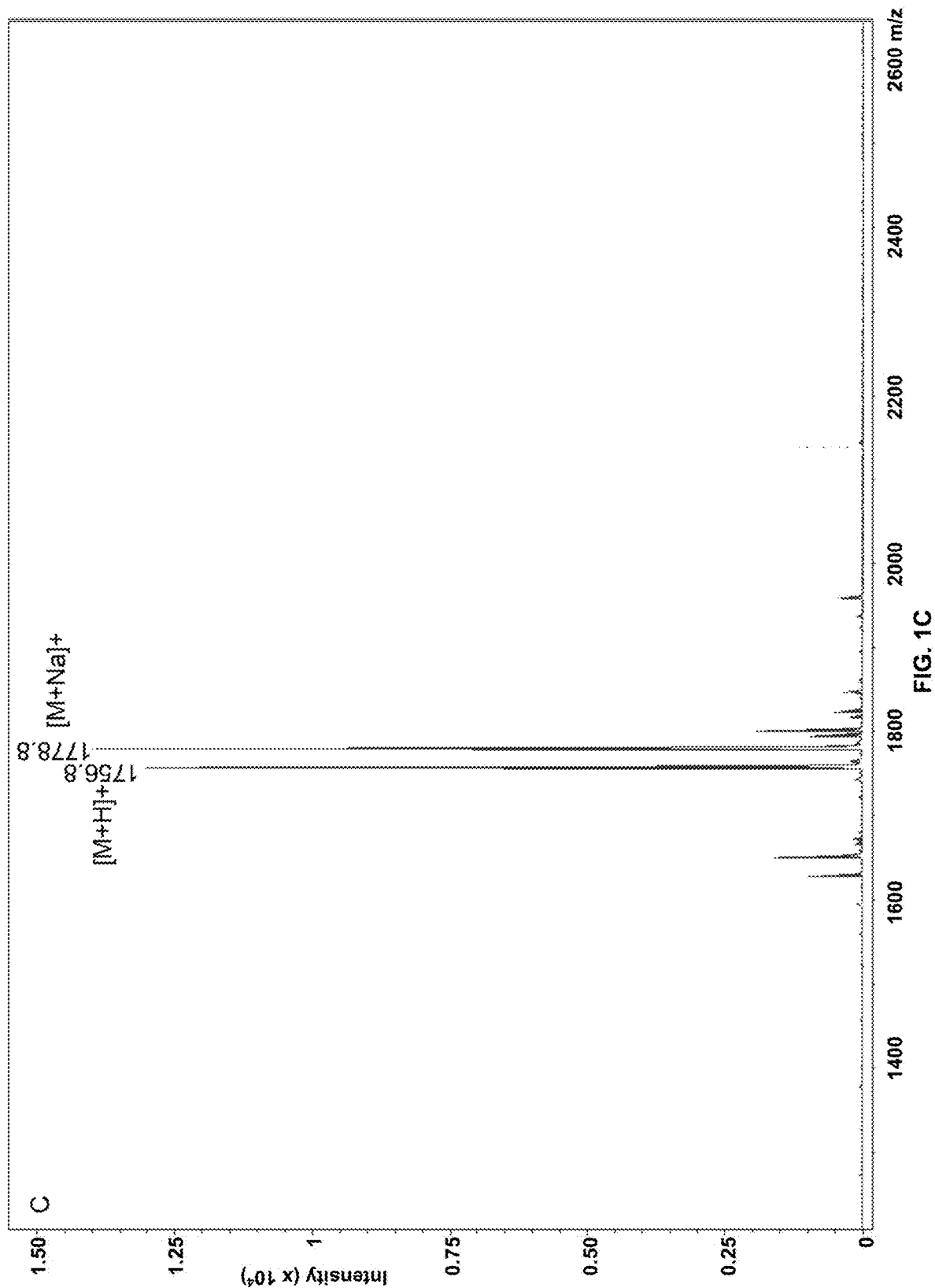
Figure 1D:
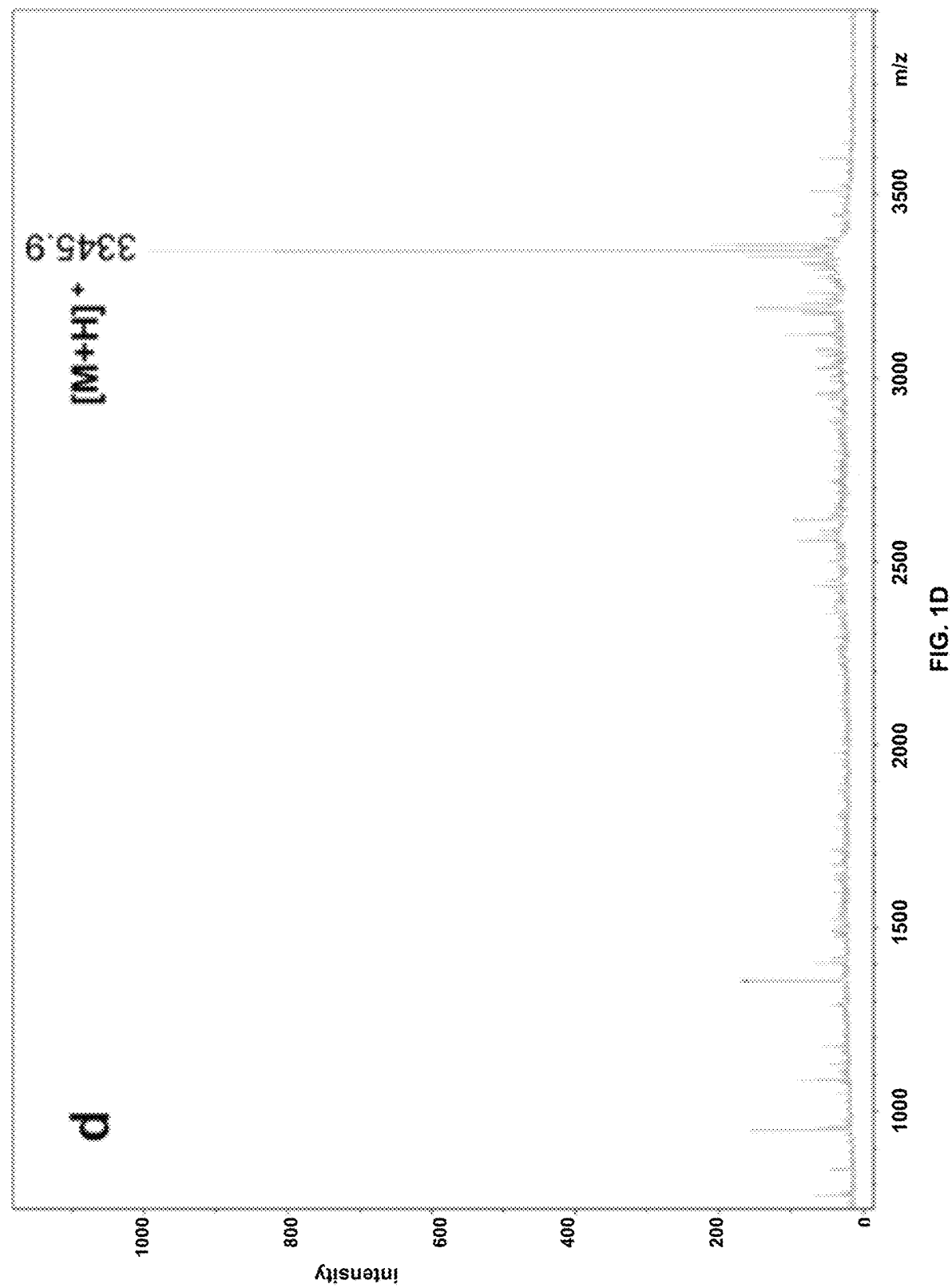
Figure 1E:
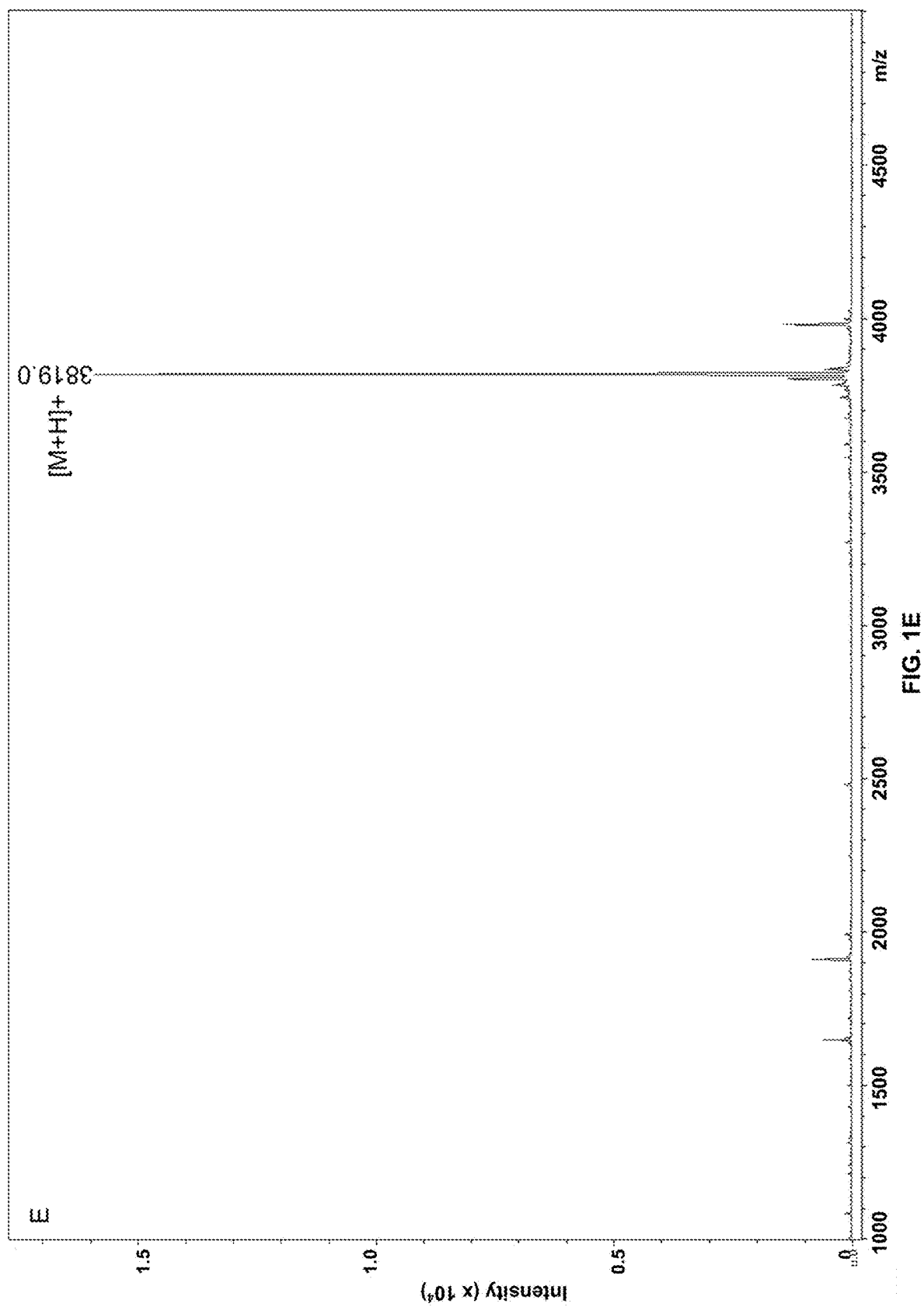
Figure 1F:
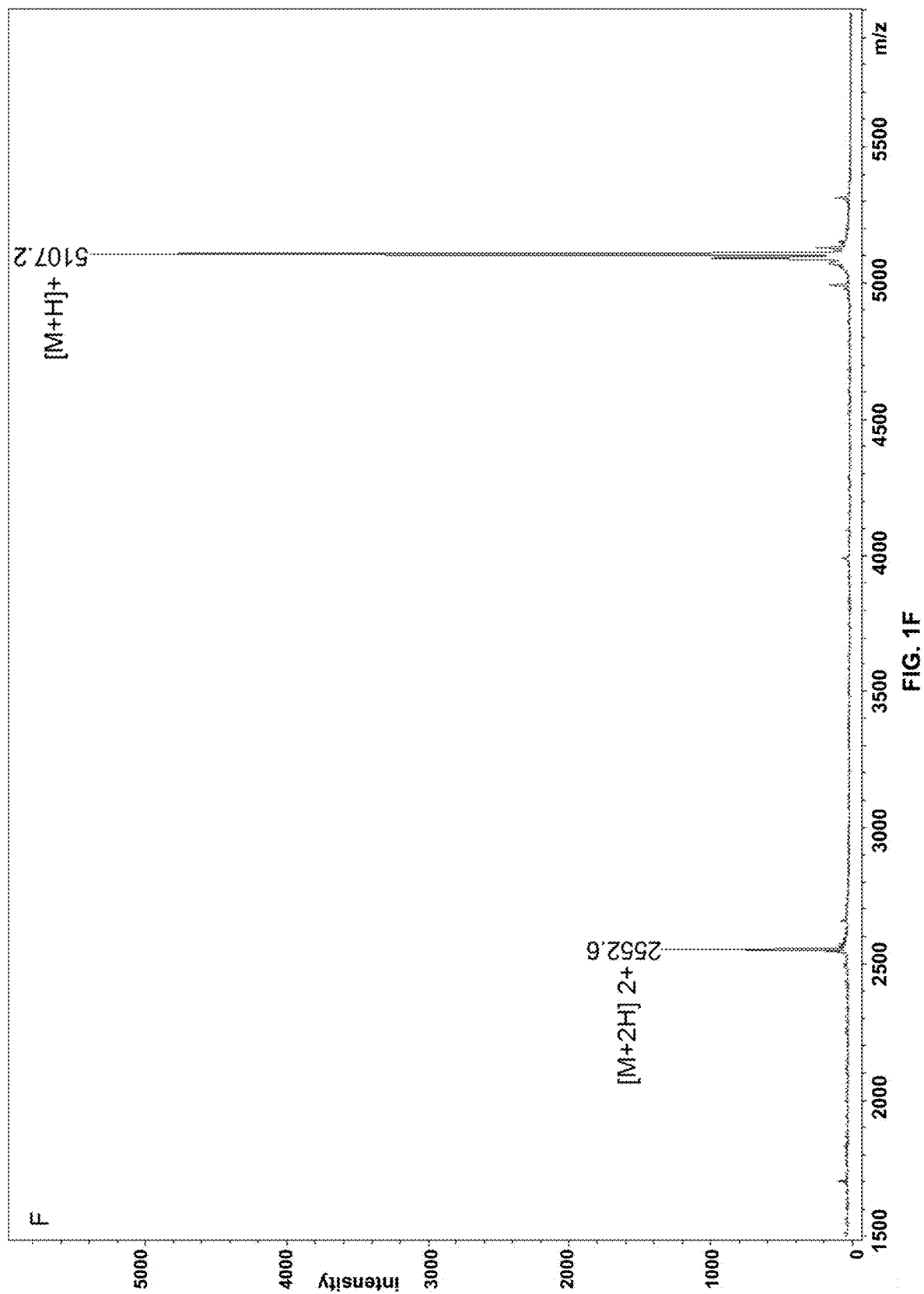
Figure 1G:
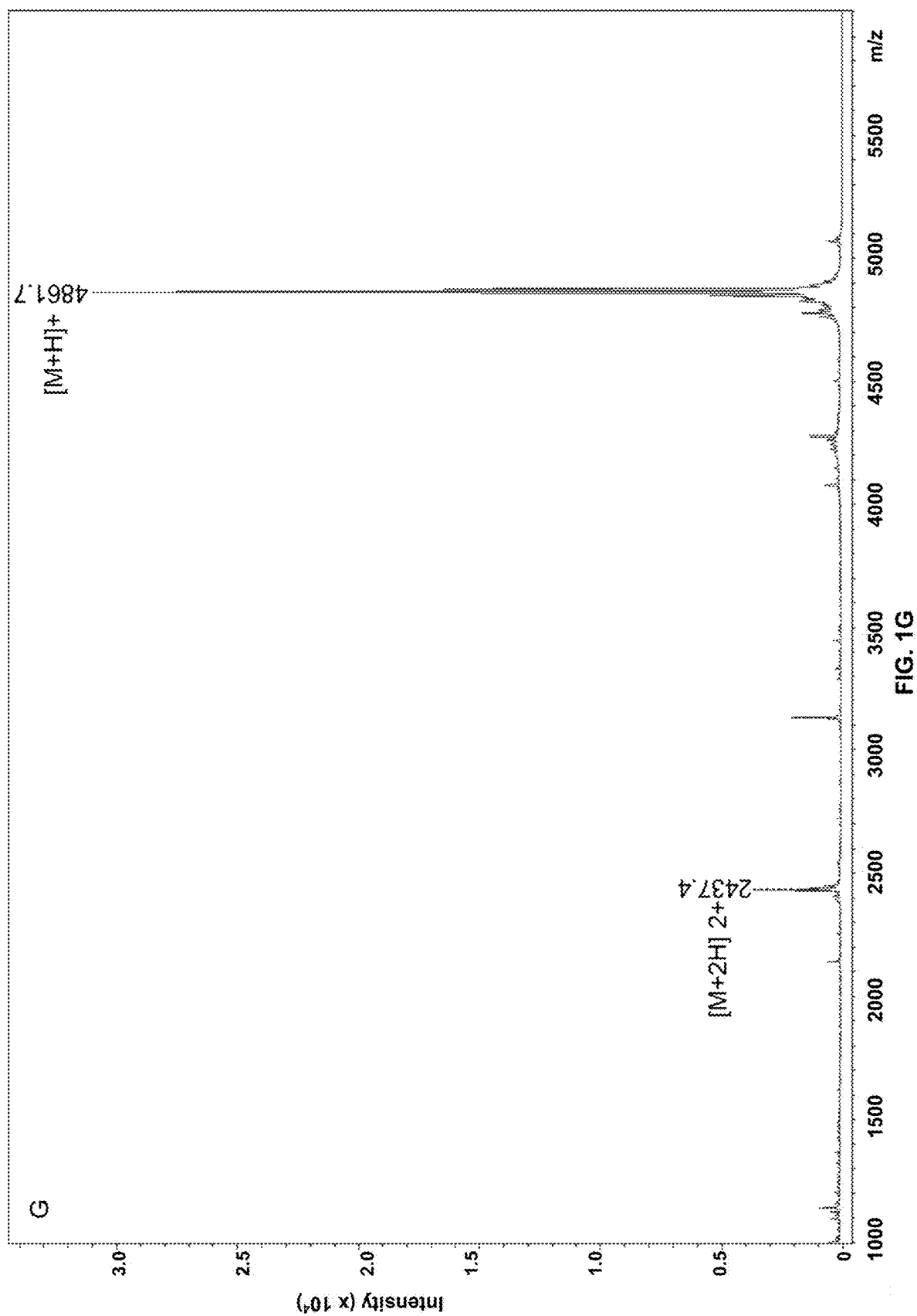

Provided herein are immunogenic compositions that are non-toxic and self-adjuvating. Described herein is a platform for vaccination based on alpha-helical self-assembling peptides assembled into nanofibers. In this strategy, peptides fold into a complex helical nanofiber. The individual peptide coils run perpendicular to the axis of a long fibril. The resultant nanostructure is composed of thousands of individual peptides or more. This folding strategy allows for greater structural control and tunable rates of assembly and disassembly. Furthermore, specific antibody responses against a tumor-specific receptor relevant to the treatment of certain cancers were raised without adjuvant. Aspects relate to an immunogenic composition comprising a peptide fibril coupled to a plurality of antigens, wherein the peptide fibril comprises alpha helices.

Peptide self-assembly has been previously explored for biomaterials applications, including cell delivery, drug delivery, and vaccine platforms. It has been previously demonstrated that epitope-bearing β-sheet fibrillizing peptides can elicit strong and specific antibody responses without supplemental immune adjuvants, making them an attractive platforms for vaccine development. However, β-sheet fibrillizing peptides lack structural precision, and the kinetics of their assembly and disassembly are difficult to control. In most cases immunization results in antibody responses that last for the lifetime of the subject, which may not be desirable for some applications, such as acute treatments or for targets that may include self-epitopes. Furthermore, the toxicity profile of β-sheet nanofibers is incompletely understood. Some β-sheet nanofibers are considerably cytotoxic and neurotoxic, while others are not, and the structural determinants of this toxicity are not well understood. The immunogenic compositions described herein avoid this complication altogether by being able to elicit adjuvant-free immune responses while avoiding β-sheet folding altogether. Instead α-helical coiled coils are used to create long nanofibers with embedded immune epitopes.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "adjuvant" refers to a compound or mixture that enhances the immune response to an antigen. Adjuvants may contain a substance to protect the antigen from rapid catabolism, such as aluminum hydroxide or a mineral oil, and also a protein derived from lipid A, *Bordatella pertussis*, or *Mycobacterium tuberculosis*. Suitable adjuvants may be commercially available and include, for example, complete or incomplete Freund's adjuvant; AS-2; aluminum salts such as aluminum hydroxide (as a gel, where appropriate) or aluminum phosphate; calcium salts, iron salts, or zinc salts; an insoluble suspension of acylated tyrosine; acylated sugars; cationically or anionically derivatized polysaccharides; polyphosphazenes; biologically degradable microspheres; monophosphoryl lipid A, cytokines such as GM-CSF, Interleukin-2, Interleukin-7, and Interleukin-12.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result.

"Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (Biometrics 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof.

"Immunogenicity" refers to the ability of an antigen to induce an immune response and includes the intrinsic ability of an antigen to generate antibodies in a subject.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. Secondary structure may include beta-sheet and alpha-helices. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. In some embodiments, a carrier includes a solution at neutral pH. In some embodiments, a carrier includes a salt. In some embodiments, a carrier includes a buffered solution. In some embodiments, a carrier includes phosphate buffered saline solution.

"Sample" or "test sample" as used herein can mean any sample in which the presence and/or level of a target is to be detected or determined or a portion from a subject or portion of an immunogenic composition as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described immunogenic compositions. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

2. Immunogenic Compositions

Described herein is a platform for vaccination or treatment based on alpha-helical peptides assembled into nanofibers. In this strategy, peptides fold into a complex alpha-helix-based nanofiber where individual peptide coils run perpendicular to the axis of a long fibril. The resultant nanostructure is composed of thousands of individual peptides or more. Nanofibers have been observed to be up to several microns long. The self-assembling peptide may be extended N-terminally with a flexible spacer and an immune epitope. In some embodiments, the composition does not further comprise an adjuvant. In some embodiments, the peptide fibril is an adjuvant.

Multiple epitope-bearing self-assembling peptides are then co-assembled into nanofibers composed not of β-sheets, but of α-helices. Coiled coil folding requires more extensive design considerations compared to β-sheet fibrillization, as both inter-helical interactions as well as those between the C-terminus and the main chain must be considered. This folding strategy allows for greater structural control and tunable rates of assembly and disassembly. This control may be useful in optimizing the materials' trafficking and engagement of specific immune cells in vivo.

a. Peptide Fibril

Certain embodiments are directed to immunogenic compositions comprising a peptide fibril. The peptide fibril comprises a plurality of self-assembling peptides. The peptide fibril may comprise a plurality of antigens coupled thereto. In some embodiments, an antigen is conjugated to a self-assembling peptide.

The peptide fibril can have a length of at least, at most, or exactly 0.01, 0.05, 0.1, 0.15, 0.20, 0.25, 0.5, 1, 5, 10, 20, 30, 40, 50, 75, 100, 125, 150, 175, 200, 225, 250, or 300 µm, including all values and ranges there between. In some embodiments, the peptide fibril is at least 100, 150, 200, 250, 300, or 350 nanometers in length. In some embodiments, the peptide fibril is less than 10, 5, or 2 µm in length. In certain aspects, the peptide fibril has a molecular weight of at least 100, 500, 1,000, 5,000, 10,000, 100,000 Da to $1 \times 10^6$, $1 \times 10^7$, $7 \times 10^8$ Da, including all values and ranges there between. The peptide fibril can have a diameter or width of at least, at most, or exactly 5, 10, 15, or 20 nm. In some embodiments, the peptide fibril is 5-20 nm in diameter or width.

In some embodiments, the composition does not further comprise an adjuvant. In some embodiments, the composition further comprises an adjuvant. In some embodiments, the peptide fibril is an adjuvant.

i) Self-Assembling Peptide

Certain aspects include self-assembling peptides. As used herein, the term "self-assembling peptide" refers to peptides that are able to spontaneously associate and form stable structures.

The self-assembling peptide may comprise an amino acid sequence of bXXXb (SEQ ID NO: 1), wherein X is independently any amino acid, and b is independently any positively charged amino acid. In some embodiments, b is independently selected from Arg and Lys. In some embodiments, b is Arg. In some embodiments, bXXXb (SEQ ID NO: 1) is RAYAR (SEQ ID NO: 2). In some embodiments, bXXXb (SEQ ID NO: 1) is KAYAK (SEQ ID NO: 3). In some embodiments, the self-assembling peptide comprises the sequence of RXXXR (SEQ ID NO: 4), wherein X is any amino acid. The self-assembling peptide may comprise an amino acid sequence of $Z_n bXXXbZ_m$ (SEQ ID NO: 5), wherein b is independently any positively charged amino acid, Z is independently any amino acid, X is independently any amino acid, n is an integer from 0 to 20, and m is an integer from 0 to 20. In some embodiments, n is an integer from 5 to 15, and m is an integer from 5 to 15. In some embodiments, the self-assembling peptide comprises a glutamine at the C-terminus. In some embodiments, the self-assembling peptide comprises a glutamine at the N-terminus. The self-assembling peptide may include at least, at most, or exactly 5, 10, 15, 16, 17, 18, 19, 20, 21, 22, 23, 24, 25, 26, 27, 28, 29, 30, 31, 32, 33, 34, 35, or 40 amino acids. In some embodiments, the self-assembling peptide comprises 5 to 40 amino acids in length.

In some embodiments, the self-assembling peptide comprises an amino acid sequence of QARILEADAEILRAYARILEAHAEILRAQ (SEQ ID NO: 6) or QAKILEADAEILKAYAKILEAHAEILKAQ (SEQ ID NO: 7) or ADAEILRAYARILEAHAEILRAQ (SEQ ID NO: 8) or a polypeptide with at least 75% identity thereto. In some embodiments, the self-assembling peptide comprises an amino acid sequence of QARILEADAEILRAYARILEAHAEILRAQ (SEQ ID NO: 6) or QAKILEADAEILKAYAKILEAHAEILKAQ (SEQ ID NO: 7) or ADAEILRAYARILEAHAEILRAQ (SEQ ID NO: 8) or a variant thereof. In some embodiments, the self-assembling peptide comprises an amino acid sequence of QARILEADAEILRAYARILEAHAEILRAQ (SEQ ID NO: 6). In some embodiments, the self-assembling peptide comprises an amino acid sequence of QAKILEADAEILKAYAKILEAHAEILKAQ (SEQ ID NO: 7). In some embodiments, the self-assembling peptide comprises an amino acid sequence of ADAEILRAYARILEAHAEILRAQ (SEQ ID NO: 8).

Self-assembling peptides may further comprise other compounds, for example, immunogenic peptides.

In some embodiments, the self-assembling polypeptide includes a modification to the C-terminus, to the N-terminus, or to both the C-terminus and N-terminus. N-terminal modifications may include, for example biotin and actyl. C-terminal modifications may include, for example, amide.

The peptides described herein can be chemically synthesized using standard chemical synthesis techniques. In some embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides described herein. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc., 85: 2149-2156, and Stewart et al. (1984) Solid Phase Peptide Synthesis, 2nd ed. Pierce Chem. Co., Rockford, Ill. In some embodiments, the self-assembling peptide is synthesized by a solid phase peptide synthesis.

Figure 6:
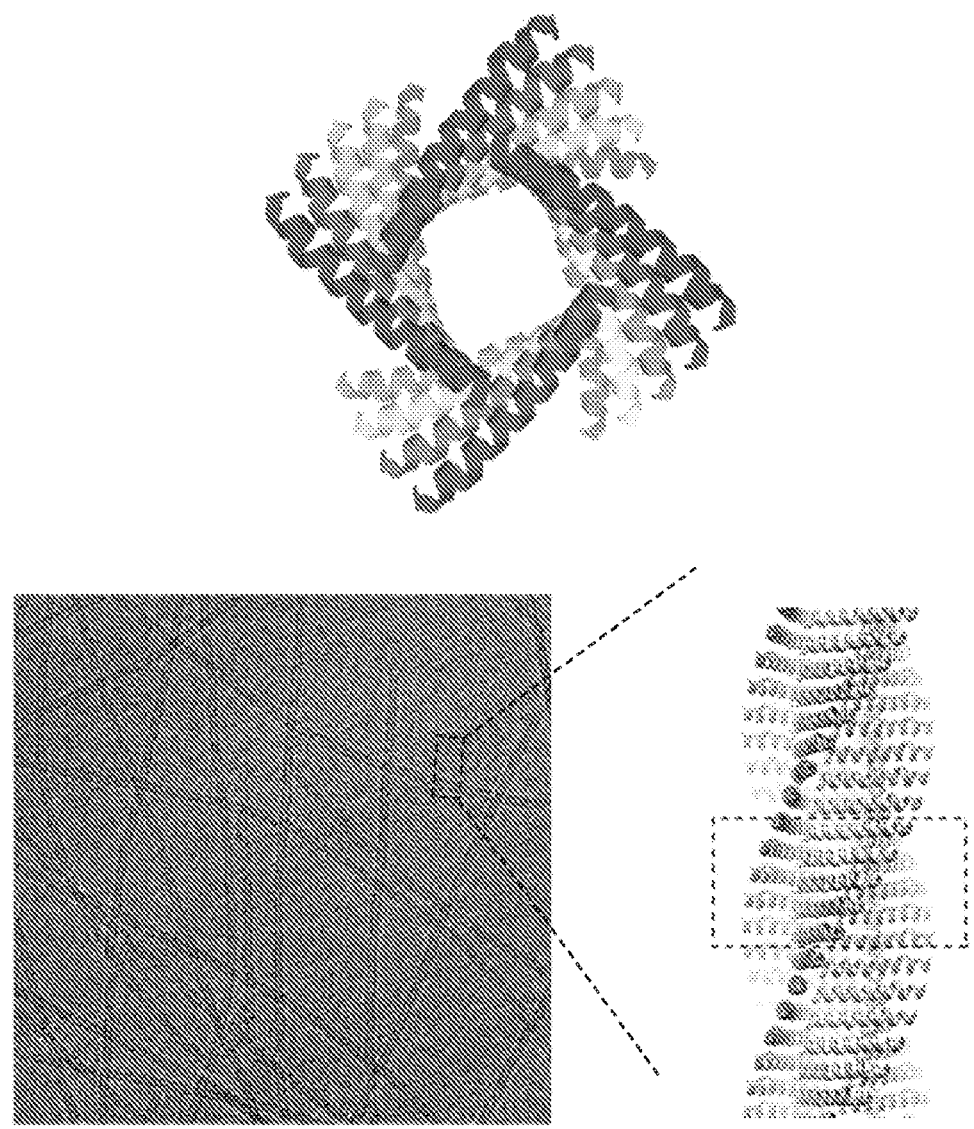
FIG. 6: Ribbon structure of alpha-helical self-assembling peptides that have spontaneously formed into a helical filament. The top is a view down the center core of the helical filament. The bottom right is a side view of the helical filament.

Each self-assembling peptide comprises or forms an alpha helix. The plurality of self-assembling peptides may form a peptide fibril in the form of a helical filament. The helical filament may be formed around a central axis or core. The plurality of self-assembling peptides may form a peptide fibril in the form of a coiled coil. In some embodiments, the N-terminus of each self-assembling peptide is positioned at the exterior of the helical filament. An example of the self-assembling peptides formed into a peptide fibril is shown schematically in FIG. 6 (Egelman et al. *Structure* 2015, 23, 280-289, incorporated herein by reference).

ii) Antigens

In in some embodiments, the peptide fibril is coupled to a plurality of antigens. A self-assembling peptide of the peptide fibril may be conjugated to an antigen. In some embodiments, each self-assembling peptide is conjugated to an antigen.

The antigen may be conjugated or coupled to a self-assembling peptide by any means known in the art, including, for example, click chemistry, Spytag/Spycatcher, oxime ligation, condensation reactions. In some embodiments, the antigen is covalently coupled to the self-assembling peptide. In some embodiments, the antigen is attached to the self-assembling peptide through a thiol reactive group. The antigen may be covalently coupled to a terminus of the self-assembling peptide. In some embodiments, the antigen is covalently coupled to the N-terminus of the self-assembling peptide. The conjugation of the antigen to the N-terminus of the self-assembling peptide may orient the antigen towards the exterior of the helical peptide fibril. In some embodiments, the antigens are exposed on the exterior surface of the peptide fibril. In some embodiments, the antigens are exposed on the exterior surface of the helical filament of the peptide fibril. In some embodiments, the antigen is covalently coupled to the self-assembling peptide. In some embodiments, the antigen is covalently coupled to a terminus of the self-assembling peptide. In some embodiments, the antigens are covalently coupled to the amino terminus of the self-assembling peptide. In some embodiments, the antigens are covalently coupled to the carboxy terminus of the self-assembling peptide.

In some embodiments, the peptide fibril comprises the same antigen. In some embodiments, the peptide fibril comprises at least two different antigens. The peptide fibril may comprise at least, at most, or exactly 1, 2, 3, 4, 5, 6, 7, 8, 9, 10, 11, 12, 13, 14, 15, 16, 17, 18, 19, 20, 30, 40, 50, 100, 500, 1000, or 10,000 different antigens (or any derivable range therein). In some embodiments, the peptide fibril includes n different antigens, wherein n is an integer from 1 to 10,000. The relative ratio of one antigen to another in the peptide fibril may be at least, at most, or exactly 1, 2, 3, 4, 5, 6, 7, 8, 9, 10, 11, 12, 13, 14, 15, 16, 17, 18, 19, 20, 50, 100, 200, 300, 400, or 500 to 1, 2, 3, 4, 5, 6, 7, 8, 9, 10, 11, 12, 13, 14, 15, 16, 17, 18, 19, 20, 50, 100, 200, 300, 400, or 500 (or any derivable range therein).

In some embodiments, the antigens are exposed on the surface of the peptide fibril. In certain aspects the ratio of antigen to self-assembling peptide is 1:1000, 1:100:1:10, or 1:1, including all values and ranges there between.

As used herein, the term "antigen" is a molecule capable of being bound by an antibody or T-cell receptor. The term "antigen", as used herein, also encompasses T-cell epitopes. An antigen also refers to a molecule against which a subject can initiate a humoral and/or cellular immune response leading to the activation of B-lymphocytes and/or T-lymphocytes. An antigen is capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In some embodiments, the antigen contains or is linked to a Th cell epitope. An antigen can have one or more epitopes (B-epitopes and T-epitopes). Antigens may also be mixtures of several individual antigens.

Antigens can be any type of biologic molecule including, for example, simple intermediary metabolites, sugars, lipids, and hormones as well as macromolecules such as complex carbohydrates, phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens. Antigens can be microbial antigens, such as viral, fungal, or bacterial; or therapeutic antigens such as antigens associated with cancerous cells or growths, or autoimmune disorders. In some embodiments, the antigen is selected from a small molecule, nucleotide, polynucleotide, peptide, polypeptide, protein, lipid, carbohydrate, other immunogenic molecules, and a combination thereof. In some embodiments, the plurality of antigens comprises a B cell epitope or T cell epitope. In some embodiments, the plurality of antigens comprises a B cell epitope and a T cell epitope. In some embodiments, the antigen comprises an autologous target. In some embodiments, the antigen comprises a cytokine. In certain compositions and methods, the antigen comprises a peptide. In some embodiments, the antigen comprises a peptide 5 to 20 amino acids in length. The peptide may be at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90 or 100 amino acids (or any derivable range therein). In some embodiments, the peptide is 5 to 20 amino acids in length. In some embodiments, the peptide fibril is peptide fibril is non-toxic.

Viral Antigens. Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B. and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS 1, NS 1, NS 1-NS2A, 80% E, and other Japanese encephalitis viral antigen components; rabies viral antigens such as rabies glycoprotein, rabies nucleoprotein and other rabies viral antigen components. See Fundamental Virology, Second Edition, e's. Fields, B. N. and Knipe, D. M. (Raven Press, New York, 1991) for additional examples of viral antigens.

Bacterial Antigens. Bacterial antigens which can be used in the compositions and methods include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diphtheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; hemophilus influenza bacterial antigens such as capsular polysaccharides and other hemophilus influenza bacterial antigen components; anthrax bacterial antigens such as anthrax protective antigen and other anthrax bacterial antigen components; rickettsiae bacterial antigens such as romps and other rickettsiae bacterial antigen component. Also included with the bacterial antigens described herein are any other bacterial, mycobacterial, mycoplasmal, rickettsial, or chlamydial antigens.

Fungal Antigens. Fungal antigens which can be used in the compositions and methods include, but are not limited to, *Candida* fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Parasite Antigens. Examples of protozoa and other parasitic antigens include, but are not limited to, *Plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; *toxoplasma* antigens such as SAG-1, p30 and other *toxoplasma* antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

Tumor antigens. Tumor antigens which can be used in the compositions and methods include, but are not limited to, telomerase components; multidrug resistance proteins such as P-glycoprotein; MAGE-1, alpha fetoprotein, carcinoembryonic antigen, mutant p53, immunoglobulins of B-cell derived malignancies, fusion polypeptides expressed from genes that have been juxtaposed by chromosomal translocations, human chorionic gonadotrpin, calcitonin, tyrosinase, papillomavirus antigens, gangliosides or other carbohydrate-containing components of melanoma or other tumor cells. It is contemplated that antigens from any type of tumor cell can be used in the compositions and methods described herein.

Antigens Relating to Autoimmunity. Antigens involved in autoimmune diseases, allergy, and graft rejection can be used in the compositions and methods. For example, an antigen involved in any one or more of the following autoimmune diseases or disorders can be used: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. An antigen can also be an altered peptide ligand useful in treating an autoimmune disease.

Examples of miscellaneous antigens which can be can be used in the compositions and methods include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

iii) Linker

The self-assembling peptide may further comprise a linker. The linker may be between the antigen and self-assembling peptide. In some embodiments, a linker is covalently attached to the self-assembling peptide between the antigen and the self-assembling peptide. In some embodiments, the linker comprises glycine and serine. In some embodiments, the antigen is attached to the self-assembling peptide through a thiol reactive group in the linker.

In some embodiments, the conjugate includes more than one linker. In such embodiments, the linkers may be the same or different from one another. The conjugate may include at least 1, at least 2, at least 3, at least 4, at least 5, at least 6, at least 7, at least 8, at least 9, or at least 10 linkers. The conjugate may include less than 20, less than 15, less than 10, or less than 5 linkers. The conjugate may include between 1 and 20, between 5 and 15, or between 1 and 5 linkers. The linker may be positioned at the C-terminus of the self-assembling peptide, at the N-terminus of the self-assembling peptide, or at both the N- and C-termini of the self-assembling peptide. In some embodiments, the linker is positioned at the N-terminus of the self-assembling peptide. Multiple linkers may be positioned adjacent to one another.

In some embodiments, the linker comprises oligoethylene glycol, polyethylene glycol, or an amino acid sequence selected from SEQ ID NO: 9 ($G_n$ wherein n is an integer from 1 to 10), SEQ ID NO: 10 (SGSG), SEQ ID NO: 11 (GSGS), SEQ ID NO: 12 (SSSS), SEQ ID NO: 13 (GGGS), SEQ ID NO: 14 (GGC), SEQ ID NO: 15 ($(GGC)_8$), and SEQ ID NO: 16 ($(G_4S)_3$).

b. Immune Response and Immunoassays

As discussed above, the compositions and methods provided herein include evoking or inducing an immune response in a subject against an antigen. In one embodiment, the immune response can protect against or treat a subject having, suspected of having, or at risk of developing an infection or related disease, or a pathological condition such as cancer or autoimmunity. One use of the immunogenic compositions is to provide effective vaccines, such as cancer vaccines. The compositions detailed herein may induce an immune response. The immune response may be an antigen-specific immune response. In some embodiments, the antigen-specific immune response is temporary or not life-long. In some embodiments, the immune response comprises IgG1 antibody isotypes. In some embodiments, the immune response is an anti-cancer immune response. The immunogenic composition may have increased immunogenicity relative to a control. In some embodiments, the control comprises the antigen without a self-assembling peptide.

Further provided herein is the implementation of serological assays to evaluate whether and to what extent an immune response is induced or evoked by compositions. There are many types of immunoassays that can be implemented. Immunoassays include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain immunoassays are the various types of enzyme linked immunosorbent assays (ELISAs) and radioimmunoassays (RIA) known in the art. Immunohistochemical detection using tissue sections is also useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non-specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non-specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

c. Protective Immunity

In some embodiments, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides may have different functionalities. While according to one aspect, a polypeptide is derived from an immunogen designed to induce an active immune response in a recipient, according to another aspect, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition as detailed herein can be administered to a subject who then acts as a source or donor for globulin, produced in response to challenge with the antigenic composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

d. Pharmaceutical Compositions

Further provided herein are methods for immunization against microbial infections or for the treatment of cancer. As such, contemplated are vaccines and therapeutics for use in active immunization of subjects. Immunogenic compositions can include a peptide fibril coupled to a plurality of antigens, "fibril complex."

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines and therapeutics may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The compositions described herein may be formulated into a pharmaceutical composition as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Typically, compositions are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the vaccine will depend on the route of administration and will vary according to the size and health of the subject.

The compositions and related methods, particularly administration of a peptide fibril/antigen complex may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

With respect to cancer treatments, the current methods and compositions described herein may be used in combination with traditional cancer therapies such as surgery, chemotherapeutics, and/or radiation therapy. Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

In yet another embodiment, the treatment is a gene therapy. In certain embodiments, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell. Examples of tumor suppressor nucleic acids within this definition include, but are not limited to APC, CYLD, HIN-I, KRAS2b, pló, pl9, p21, p27, p27mt, p53, p57, p73, PTEN, Rb, Uteroglobin, Skp2, BRCA-I, BRCA-2, CHK2, CDKN2A, DCC, DPC4, MADR2/JV18, MENI, MEN2, MTSI, NF1, NF2, VHL, WRN, WTI, CFTR, C-CAM, CTS-I, zacl, scFV, MMACI, FCC, MCC, Gene 26 (CACNA2D2), PL6, Beta* (BLU), Luca-1 (HYALI), Luca-2 (HYAL2), 123F2 (RASSFI), 101F6, Gene 21 (NPRL2), or a gene encoding a SEM A3 polypeptide and FUSI. Other exemplary tumor suppressor genes are described in a database of tumor suppressor genes at www.cise.ufl.edu/~yyl/HTML-TSGDB/Homepage.litml. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied.

In one aspect, it is contemplated that a peptide fibril/antigen vaccine and/or therapy is used in conjunction with an additional treatment described herein. Alternatively, the therapy may precede or follow the other agent treatment by intervals ranging from minutes to weeks. In embodiments where the other agents and/or a proteins is administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6, or 7) to several weeks (1, 2, 3, 4, 5, 6, 7, or 8) lapse between the respective administrations.

Various combinations may be employed, for example antibiotic therapy is "A" and the immunogenic composition is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the immunogenic compositions to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

In some embodiments, pharmaceutical compositions are administered to a subject. Different aspects involve administering an effective amount of a composition to a subject. In some embodiments, immunogenic compositions may be administered to the patient to protect against infection by one or more microbial pathogens. Additionally, such compounds can be administered in combination with an antibiotic or other known anti-microbial therapy. Such compositions will generally be dissolved or dispersed in a pharmaceutically acceptable carrier or aqueous medium. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active compounds can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. In some embodiments, the immunogenic composition is administered to the subject intravenously, intraarterially, intraperitoneally, subcutaneously, intranasally, intramuscularly, or intratumorally.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

e. Methods i) Methods of Inducing an Immune Response

Further provided herein are methods of inducing an immune response in a subject. The methods may include administering to the subject the immunogenic composition as detailed herein in an amount sufficient to induce an immune response in a subject. In some embodiments, the immune response is an antigen-specific immune response. Further provided herein is an antibody produced in the immune response.

Further aspects relate to a method of inducing an immune response and/or antigen-immune response in a subject comprising administering to the subject the immunogenic composition as detailed herein in an amount sufficient to induce an immune response and/or antigen-specific immunity. In some embodiments, the immune response is an antigen-specific immune response. In some embodiments, the antigen-specific immunity is temporary and/or not life-long. Antigen-specific immunity refers to an adaptive immune response that occurs upon subsequent encounter with an antigenic determinant. In life-long immunity, vaccination protects the subject from environmental encounters with the antigen by inducing an immune response after the antigen has been encountered. Aspects relate to embodiments in which the immunity is temporary or lasts less than 20, 15, 10, 9, 8, 7, 6, 5, 4, 3, 2, or 1 years (or any derivable range therein). In some embodiments, the immune response comprises IgG1 antibody isotypes. In some embodiments, IgG1 antibody isotypes are the dominant antibody isotype produced in the immune response. In some embodiments, IgG1 antibody isotypes are significantly more in relation to the other antibody isotypes in the immune response. In some embodiments, the titer of IgG1 is at least 1, 1.5, 2, 2.5, or 3 log 10 units higher than other isotypes.

Further aspects relate to an antibody produced in the immune response of the methods as detailed herein.

Further methods relate to a method of treating a subject having or at risk of developing a microbial infection or pathological condition, the method comprising administering to the subject an effective amount of a composition or antibody as detailed herein. In some embodiments, the pathological condition is cancer. In some embodiments, the pathological condition is an autoimmune disorder.

Further aspects relate to a method for making the compositions as detailed herein comprising mixing self-assembling peptides and a carrier to make a peptide fibril.

ii) Treatment of Disease

Further provided herein are methods of treating a subject having or at risk of developing a microbial infection or pathological condition. The methods may include administering to the subject an effective amount of a composition or antibody as detailed herein.

Embodiments relate to treatments, such as vaccines for treating cancer. In some embodiments, the cancer is glioblastoma. In some embodiments, the immune response is an anti-cancer immune response. The cancers amenable for vaccination according to the methods described herein include, but are not limited to, tumors and cancers of all types, locations, sizes, and characteristics. The methods and compositions as detailed herein are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye Cancer, intraocular melanoma eye Cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma, squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

Embodiments can be used to treat or ameliorate a number of immune-mediated, inflammatory, autoimmune, or auto-immune-inflammatory diseases, e.g., allergies, asthma, diabetes (e.g. type 1 diabetes), graft rejection, etc. Examples of such diseases or disorders also include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen *nitidus*, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus *foliaceus*, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolysis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

In some embodiments, the pathological condition is cancer or autoimmunity.

iii) Methods of Making

Further provided herein are methods for making the immunogenic composition as detailed herein. The methods may include mixing self-assembling peptides, at least some of which are conjugated to antigen, to make a peptide fibril. The method may include mixing multiple self-assembling peptides to make a peptide fibril. In some embodiments, at least some of the self-assembling peptides are conjugated to antigen. In some embodiments, all of the self-assembling peptides are conjugated to antigen. The antigens of each peptide fibril may be the same or different. In some embodiments, the first and second antigens are different.

The methods may include providing a first peptide fibril comprising self-assembling peptides conjugated to a first antigen; providing a second peptide fibril comprising self-assembling peptides conjugated to a second antigen; and mixing together the first and the second peptide fibrils.

The methods may include providing a first peptide fibril comprising self-assembling peptides conjugated to an antigen; providing a second peptide fibril comprising self-assembling peptides not conjugated to an antigen; and mixing together the first and the second peptide fibrils.

The methods may include providing a first peptide fibril comprising self-assembling peptides conjugated to a first antigen; providing a second peptide fibril comprising self-assembling peptides conjugated to a second antigen; providing a third peptide fibril comprising self-assembling peptides not conjugated to an antigen; and mixing together the first, the second, and the third peptide fibrils.

The methods may include providing a first mixture comprising a plurality of self-assembling peptides, each self-assembling peptide conjugated to a first antigen; providing a second mixture comprising a plurality of self-assembling peptides, each self-assembling peptide conjugated to a second antigen; and mixing together the first mixture and the second mixture to form peptide fibrils, each peptide fibril comprising the first and second antigen.

The methods may include providing a first mixture comprising a plurality of self-assembling peptides conjugated to an antigen; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen.

The methods may include providing a first mixture comprising a plurality of self-assembling peptides conjugated to a first antigen; providing a second mixture comprising a plurality of self-assembling peptides conjugated to a second antigen; providing a third mixture comprising a plurality of self-assembling peptides not conjugated to an antigen; and mixing together the first, the second, and the third mixtures to form peptide fibrils, each peptide fibril comprising the first antigen, the second antigen, and a portion of the self-assembling peptides not conjugated to an antigen.

In some embodiments, the first and second antigens are different.

The methods may include providing a first mixture comprising a plurality of self-assembling peptides conjugated to one or more antigens; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen. In some embodiments, the antigens are the same. In some embodiments, the antigens are different. In some embodiments, the peptide fibril comprises n different antigens, wherein n is an integer from 1 to 10,000.

3. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Materials and Methods

Peptide Synthesis and Characterization: All peptides were synthesized using standard Fmoc solid-phase chemistry with PEG resin (manufacturer), purified via high performance liquid chromatography (HPLC) and confirmed via matrix-assisted laser desorption/ionization mass spectrometry (MALDI-MS). Biotinylated peptides were prepared by reacting Biotin-ONp (Novabiochem) in DMF overnight in a 3-fold molar excess with amine-terminated peptides before cleavage from the resin. TAMRA labeled peptides were synthesized by reacting 5(6)-TAMRA (Anaspec Inc.) in 3-fold molar excess with amine-terminated peptides on resin in the presence of N,N'-Diisopropylcarbodiimide (DIC) and 6-Chloro-1-Hydroxy-1H-Benzotriazole (HOBt-CI) in DMF overnight. A summary of peptides with sequences and molecular weights is provided in the TABLE 1. For analysis by transmission electron microscopy (TEM), peptide solutions were prepared in the same way as for immunization, diluted to $0.2\times10^{-3}$ M in 1×PBS immediately before deposition on 400 mesh carbon grids, stained with 1% uranyl acetate, and imaged using a FEI Tecnai F30.

Vaccine Preparation: To prepare PEPvIII-Coil29 peptide fibers solutions for immunization, the lyophilized peptides were first dissolved in $10\times10^{-3}$ M sterile acetate buffer (pH 4) at $8\times10^{-3}$ M and incubated overnight at −4° C. The peptide solutions were subsequently diluted to $2\times10^{-3}$ M in 1×PBS, and incubated 3 h at room temperature prior to immunization. For coassembled peptide fiber formation, PEPvIII-Coil29 and PADRE-Coil29 were weight out separately, and mixed on vortex for 5 mins before dissolved in $10 \times 10^{-3}$ M sterile acetate buffer (pH 4), and diluted in the same procedure as PEPvIII-Coil29 nanofiber preparation. To prepare CFA/IFA peptide emulsion for immunization, PEPvIII peptide was initially dissolved in $4 \times 10^{-3}$ M in sterile water, and equal volume of adjuvant solution was mixed in with peptide solution and vortexed for 45 min to bring the final concentration of peptide to $2 \times 10^{-3}$ M for injection.

Mice and Immunizations: Female 057B1/6 mice were purchased from Harlan laboratory and housed at the animal facility at the University of Chicago and Duke University. All procedures were approved by both the University of Chicago Institutional Animal Care and Use Committee (protocol 71-900) and the Duke Institutional Animal Care and Use Committee (protocol A314-15-12 19N). Mice (6-12 weeks old; age-matched within each experiment) were randomly assigned in groups of five for each condition based on previous findings that this size was sufficient to distinguish responding versus nonresponding groups. Anesthetized mice were immunized subcutaneously with the indicated solutions ($2 \times 50$ μL at the shoulders) and boosted where indicated with half-doses ($2 \times 25$ μL) after 4 weeks and 7 weeks. Sera were collected from the submandibular (cheek) vein for analysis via ELISA. Mice were sacrificed 7 d after the final immunization, and the cells from the draining lymph nodes (axillary, brachial, and inguinal) were collected.

Antibodies and Flow Cytometry: Antibodies were purchased from eBioscience unless specified. Flow cytometry was performed using LSRII blue (BD). FlowJo (Tree Star Inc.) was used in the analysis of flow data. For analysis of cell recruitment to the peritoneal cavity, cells isolated from i.p. lavage fluid were stained and analyzed as described.

T-Cell ELIspot: T-cell ELIspots were performed as described. Briefly, 0.25 million cells from the spleen were plated in each well of a 96-well ELIspot plate (Millipore, MSIPS4510), in 200 μL per well. The cells were then stimulated with peptide or left untreated as negative controls. Preliminary experiments showed that the response to PADRE saturated at concentrations above $0.5 \times 10^{-6}$ M. Therefore, stimulation was performed with $1 \times 10^{-6}$ M PADRE; when E214Q11 or pOVA were used, they were included at $5 \times 10^-$, M. IL-4 (551818) or INF-γ (551881) ELISPOT Pairs were from BD. Streptavidinalkaline phosphatase (3310-10) was purchased from Mabtech. Spots were developed using substrate Sigmafast BCIP/NBT (Sigma, B5655). Plates were imaged and enumerated using an ELISPOT reader (Cellular Technology, Ltd).

ELISA for Serum Antibodies: Serum was analyzed for antigenspecific Ig (Anti-IgG (H+L), Jackson Immuno Research, Cat #115-035-003) or IgG (gamma-specific, #115-035-071) by ELISA, as previously described (Egelman, E. H., et al. Structure 2015, 23, 280-28). To detect E214-specific antibodies, the plate was coated with 5 μg/mL E214-ahx-C (provided by Merck) in PBS or with 5 μg/mL streptavidin (Sigma #85878) followed by 10 μg/mL E214-PEG-biotin in PBS. To detect antibodies specific for Q11 or PADREQ11, the plate was coated with 20 μg/mL SGSG-Q11 or PADRE-Q11 in PBS. Isotyping was conducted similarly except that alkaline-phosphatase-conjugated antibodies for total IgG (#155-055-071) or IgG1, IgG2b, IgG2c, or IgG3 (#155-055-205, 155-055-207, 155-055-208, 155-055-209, respectively) were used (diluted 1:5000) along with SigmaFast pNPP substrate.

Example 2

Alpha-Helical Peptide Nanofibers as a Self-Adjuvanting Vaccine Platform

A peptide fibril was designed to incorporate both the universal CD4+ T cell epitope (PADRE, aKXVAAWTL-KAa, where "X" is cyclohexylalanine, and "a" is D-alanine)[3] and a B-cell target epitope (PEPvIII, LEEKKGNYVVTDH) from the epidermal growth factor receptor class III variant (EGFRvIII), a tumor-specific receptor present in a significant proportion of glioblastomas and other human cancers. Separate peptides were synthesized, containing one of the epitope peptides N-terminally linked to the coil29 peptide (TABLE 1). The T cell and B cell epitope peptides were then co-assembled into coiled coil nanofibers presenting both epitopes. In mice, the antibody responses elicited by the epitope-bearing fiber were found by ELISA to be epitope-specific, dependent upon self-assembly, and comparable in titers to that raised by epitope peptide delivered in complete Freund's adjuvant (CFA), a very strong adjuvant.

TABLE 1

Summary of the molecular weights of peptides involved in this study.

| Peptides | Sequence | Calculated [M + H]$^+$ | Observed [M + H]$^+$ |
| --- | --- | --- | --- |
| NH2-PEPvIII | NH2-LEEKKGNYVVTDH-Amide (SEQ ID NO: 17) | 1532 | 1530 |
| NH2-PADRE | NH2-aKXVAAVVTLKAa-Amide (SEQ ID NO: 18) | 1284 | 1282 |
| Biotin-PEPvIII | Biotin-LEEKKGNYVVTDH-Amide (SEQ ID NO: 17) | 1756 | 1756 |
| Biotin-SGSG-Coil29 | Biotin-SGSG QARILEADAEILRAYARILEAHAEILRAQ-Amide (SEQ ID NO: 19) | 3819 | 3819 |
| Coil29 | Actyl-QARILEADAEILRAYARILEAHAEILRAQ-Amide (SEQ ID NO: 6) | 3347 | 3346 |

TABLE 1-continued

Summary of the molecular weights of peptides involved in this study.

| Peptides | Sequence | Calculated [M + H]⁺ | Observed [M + H]⁺ |
|---|---|---|---|
| PEPvIII-Coil29 | NH2-LEEKKGNYVVTDH SGSG QARILEADAEILRAYARILEAHAEILRAQ-Amide (SEQ ID NO: 20) | 5107 | 5107 |
| PADRE-Coil29 | NH2-aKXVAAVVTLKAa SGSG QARILEADAEILRAYARILEAHAEILRAQ-Amide (SEQ ID NO: 21) | 4858 | 4861 |

Peptides were synthesized by solid phase peptide synthesis by methods known in the art. The morphology of the self-assembled fiber was studied using both circular dichroism (CD) and transmission electron microscopy (TEM). Immunizations were given in sterile PBS to female C57BL/6 mice subcutaneously. After 4 weeks, each mouse was boosted with one-half the primary dose. Mice in the CFA group were boosted with incomplete Freund's adjuvant (IFA). Antibody titers were determined using ELISA.

Figures 2A, 2B, 2C, 2D, 2E:
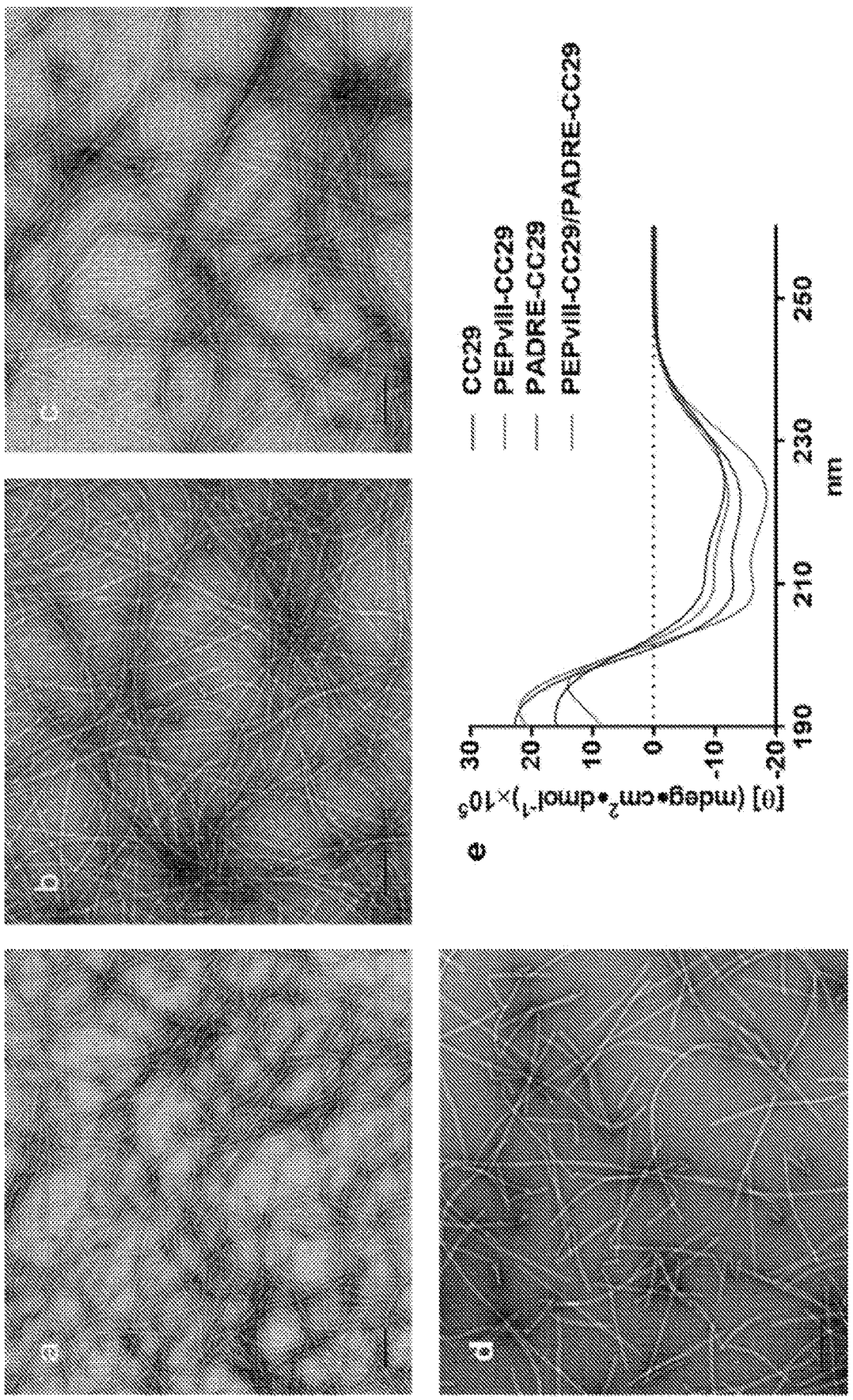
FIGS. 2A-2E: Coil29 and epitope bearing Coil29 fibril formation and structural analysis. TEM images of Coil29, and epitope bearing coil29 fibers after incubation in PBS, (FIG. 2A) Coil29, (FIG. 2B) PEPvIII-Coil29, (FIG. 2C) PEPvIII-Coil29/PADRE-Coil29, and (FIG. 2D) PADRE-Coil29, Scale bar 100 nm.

The coil29 peptide (QARILEADAEILRAYARILEAHAEILRAQ, SEQ ID NO: 6) self-assembled into cylindrical α-helical fibers in our hands. TABLE 1 summarizes all the peptides synthesized for the current study. With N-terminal extension of the epitope sequence, the modified coil29 peptide could still self-assemble into α-helical fibers according to TEM and CD (FIG. 2). This was a surprising finding, as one would expect that a long additional peptide would disrupt helix folding. According to TEM, the morphology of peptide fiber formed by mixing PEPvIII-Coil29 and PADRE-Coil29 (10/1 ratio) resembled that of Coil29 peptide alone, indicating that B cell epitope peptides are well tolerated by this system. The fibrillization process of PADRE-Coil29 was similar to that of PEPvIII-Coil29, although the fibers were somewhat shorter (FIG. 2D). Overall, the TEM and CD results showed that epitopes could be tolerated in the assembly of Coil29.

Figure 3:
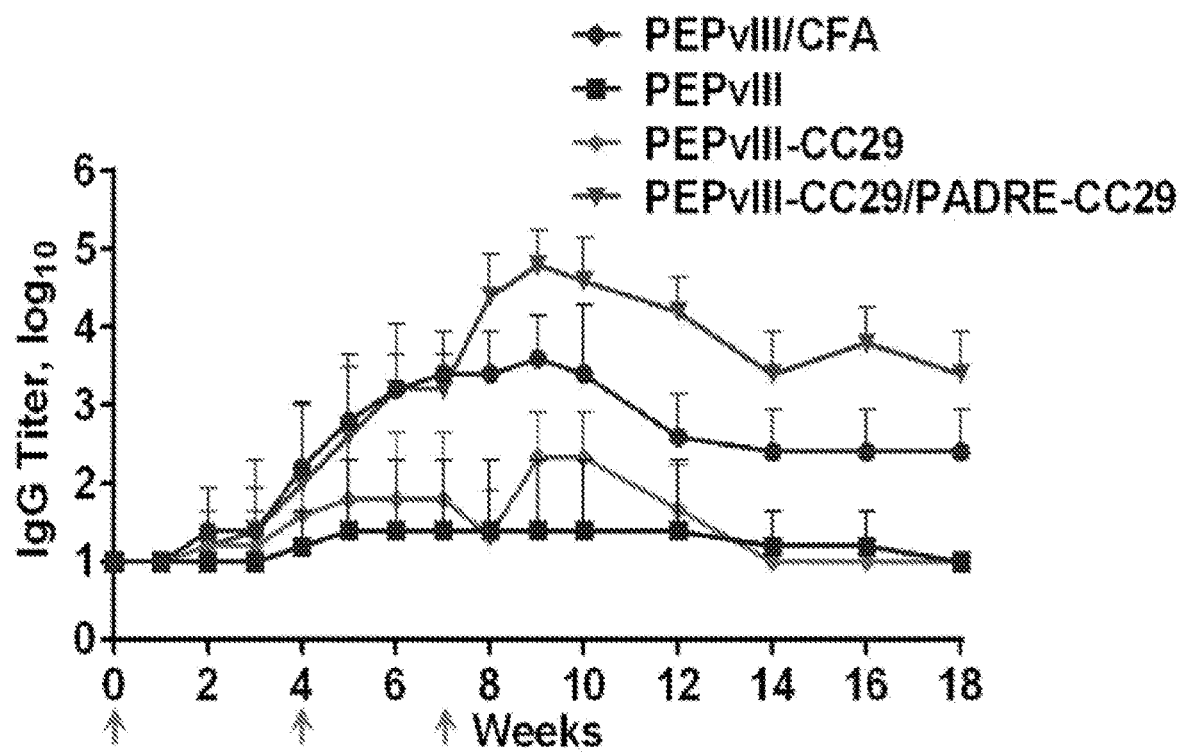
FIG. 3: IgG antibody responses against the PEPvIII epitope after immunization with various formulations. Two boosters containing half the primary immunization dose were given after 4 weeks and 7 weeks for all the groups. The co-assembled fibers containing both the PEPvIII B cell epitope and PADRE T cell epitope raised strong and durable antibody responses (in the legend, the Coil29 peptide is labeled "0029"). N=5 mice per group.
Figure 4:
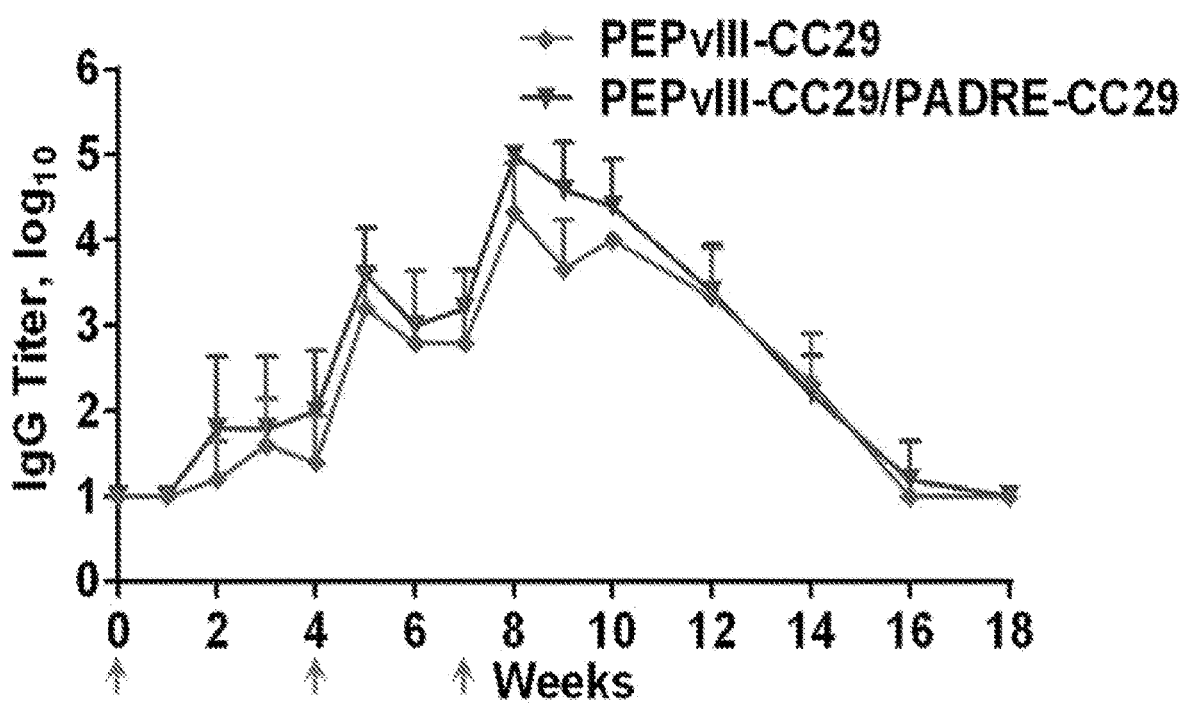
FIG. 4: IgG antibody response against the non-epitope portion (SGSG-Coil29) is T-cell independent, self-limiting, and significantly diminished after booster injections. Two boost containing half the primary immunization doses were given on week 4 and week 7 for both groups. Sera were collected to measure the IgG production against SGSG-Coil29 peptide using ELISA.

Without adjuvant, the nanofibers containing both the B cell epitope and the T cell epitope elicited titers greater than PEPvIII codelivered with a very strong adjuvant, CFA (FIG. 3). In contrast, the PEPvIII peptide alone (epitope only) did not elicit antibody responses, and the nanofibers containing only PEPvIII and lacking PADRE elicited very weak responses (FIG. 3), after which the titer level diminished to the same level as negative control group (PEPvIII). These results indicated that the antibody production in this system depends upon the self-assembled fibrillar organization and is T-cell dependent. Antibody responses against the carrier (SGSG Coil29 sequence) were also measured by ELISA for both PEPvIII-Coil29 group and PEPvIII-Coil29/PADRE-Coil29 group (FIG. 4). The antibody titer level was similar between both groups, regardless of the presence of PADRE sequence, and it was self-limiting, returning to baseline levels after 16 weeks.

Figure 5:
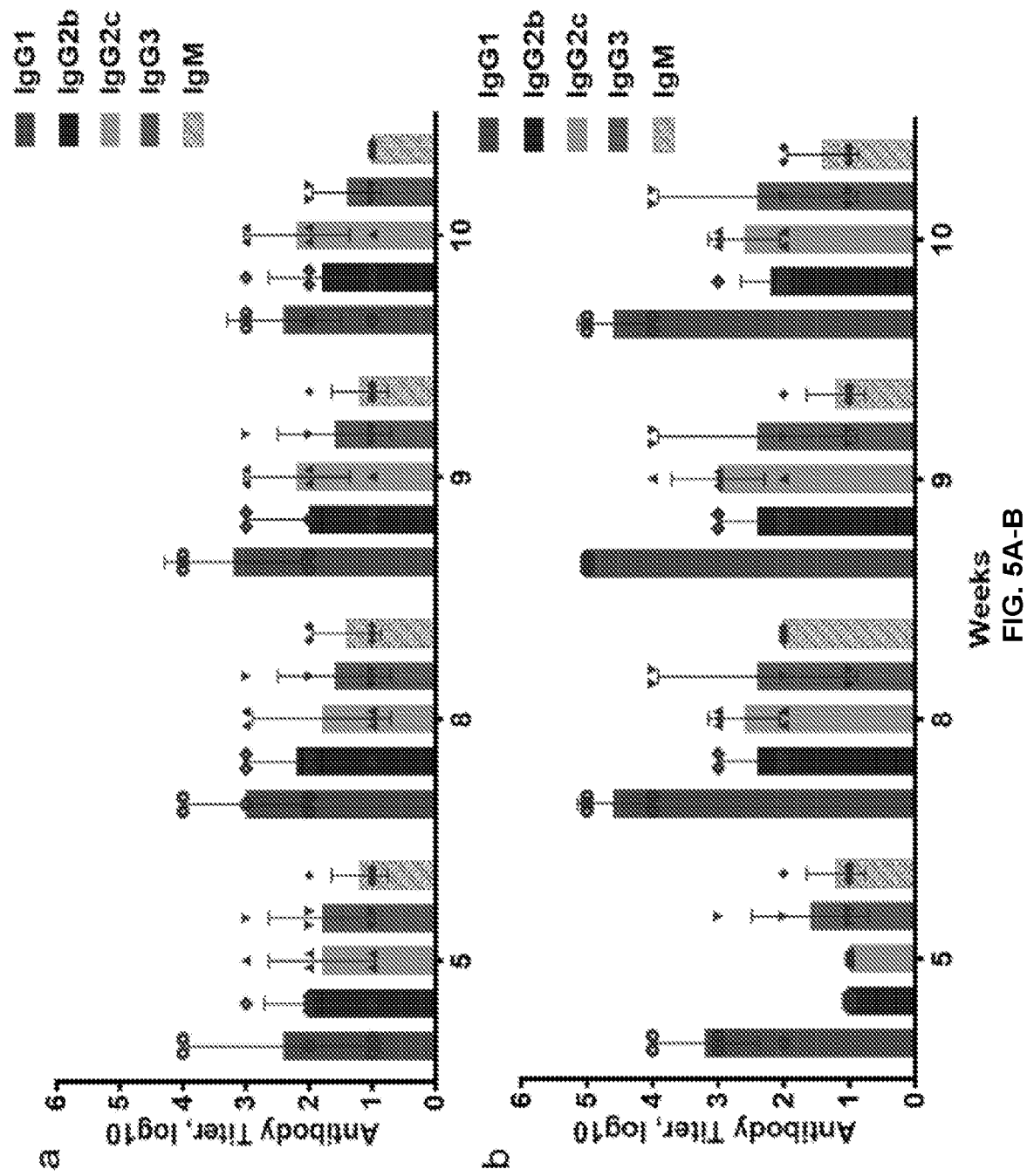
FIGS. 5A-5B: The Isotype distribution of antibody response against PEPvIII epitope for (FIG. 5A) PEPvIII/CFA group, and (FIG. 5B) PEPvIII-Coil29/PADRE-Coil29 group. Antibody isotypes were analyzed after two boost injections, on week 5 and week 8, and were monitored subsequently on week 9 and week 10. IgG1 was found to be the main isotype produced in the humoral immune response against PEPvIII peptide. Each time point comprises a bar for antibody titer data for IgG1, IgG2b, IgG2c, IgG3, and IgM, respectively.

IgG1 antibody isotypes are critical for anticancer therapeutic applications. In the current study, IgG1 is the main isotype produced in both PEPvIII-Coil29/PADRE-Coil29 and PEPvIII/CFA group, but the IgG1 level is more dominant for the nanofiber group (FIG. 5).

Finally, the temporary immunogenicity of this material is an advantage, because in many applications such as the one targeted here (cancer) one may not wish to have a life-long immunity against an endogenous protein. In this way, the reported vaccine platform is advantageous compared to conventional vaccines and compared to other fibrillized peptides based on β-sheet fibrillizing peptides, which elicit protracted antibody responses for the duration of the subject's life.

In conclusion, epitope-bearing Coil29 peptides self-assembled into α-helical fibers, with morphologies similar to the unmodified peptide. Specific antibody responses against an EGF receptor epitope relevant to the treatment of glioblastoma were raised without adjuvant. The co-assembly of PADRE-Coil29 augmented the response to a level higher than mice receiving a strong adjuvant, CFA. Additionally, IgG1 was found to be the main antibody isotype in the mice immunized by PEPvIII-Coil29/PADRE-Coil29 peptide group. These results indicate that this platform may be useful in the development of self-adjuvanting vaccines.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 3

A new self-assembly platform based on Coil29 peptides (QARILEADAEILRAYARILEAHAEILRAQ, SEQ ID NO: 6) was designed, which fold and assemble into α-helical nanofibers. This folding strategy allows for a greater structural control and tunable rates of assembly and disassembly. We expect this peptide to be useful in optimizing the materials trafficking and engagement of specific immune cells in vivo. The self-assembled peptide fiber was designed to incorporate both the universal CD4+ T cell epitope (PADRE, aKXVAAWTLKAa, where "X" is cyclohexylalanine, and "a" is D-alanine) and a B-cell epitope (PEPvIII, LEEKKGNYVVTDH) targeting the epidermal growth factor receptor class III variant (EGFRvIII), a tumor-specific receptor present in a significant proportion of glioblastomas and other human cancers. Both T cell and B cell epitopes were covalently linked to the helical peptide with N-terminal extensions. We also investigated the ability of alpha-helical peptide fibers to elicit CD8+ T cell response by conjugating the H-2kb-restricted OT-1 peptide epitope (SIINFEKL, SEQ ID NO: 23) with Coil29 via a proteasome-cleavable linker (AAYGG, SEQ ID NO: 24) to facilitate the epitope processing in APC.

Figure 7:
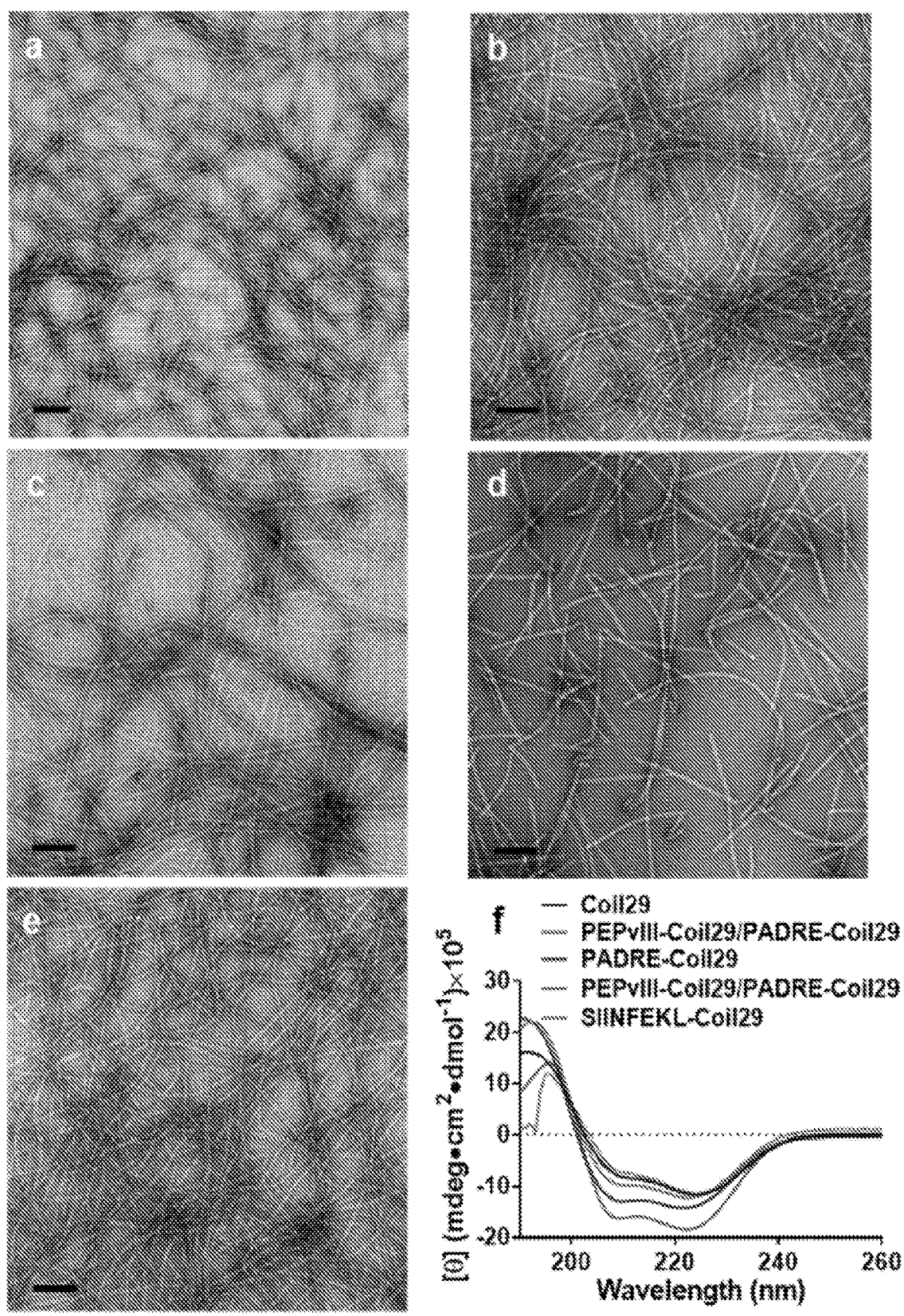
FIGS. 7A-7F: Coil29 peptide self-assembled into α-helical nanofibers with different functional epitopes.

The peptide Coil29 can self-assemble into nanofibers with four α-helical Coil29 peptides forming "square" intersection and the N-termini resting on the peripheral of the assembled fiber. This particular structural feature enabled the fusion of the epitopes onto the Coil29 sequence through N-terminal extension using solid phase peptide synthesis. The obtained peptides were confirmed using MALDI and purified via HPLC prior to the following studies. (TABLE 1 and FIG. 16). To examine whether the epitopes' inclusion impaired the modified Coil29 peptide's ability to assemble or altered the secondary structures, the morphologies of peptide assembly in 1×PBS were studied using TEM and CD (FIG. 7). Coil29 peptide self-assembled into the nanofibers in 1×PBS in our hands revealed by TEM imaging, and the α-helix structured was confirmed in CD spectra (FIG. 7A and FIG. 7E). With the epitopes attached, both PEPvIII-Coil29 (P-C) and SIINFEKL-Coil29 (S-C) self-assembled into nanofibers with a diameter (~10 nm) very similar to that of Coil29 peptide (~6 nm), demonstrating the well-behaved nature of the Coil29 peptide fibrilization process (FIG. 7B and FIG. 7E). Moreover, the α-helical characteristics were preserved in the presence of these epitopes, as evidenced by the two molar ellipticity minima at 208 nm and 222 nm from circular dichroism study (FIG. 7F). Although the PADRE epitope modification produced shorter α-helical fiber assembly possibly due to the hydrophobicity of PADRE sequence interfering the self-assembly process, the secondary structure of PADRE-Coil29 fiber was still unaltered (FIG. 7D and FIG. 7F). By mixing the PEPvIII-Coil29 with PADRE-Coil29 at a molar ratio of 20/1 (P-C/P) before dissolution in 1×PBS, the high aspect ratio nanofiber morphology resembling the Coil29 fibers was recovered according to TEM imaging. (FIG. 7C).

Figure 8A:
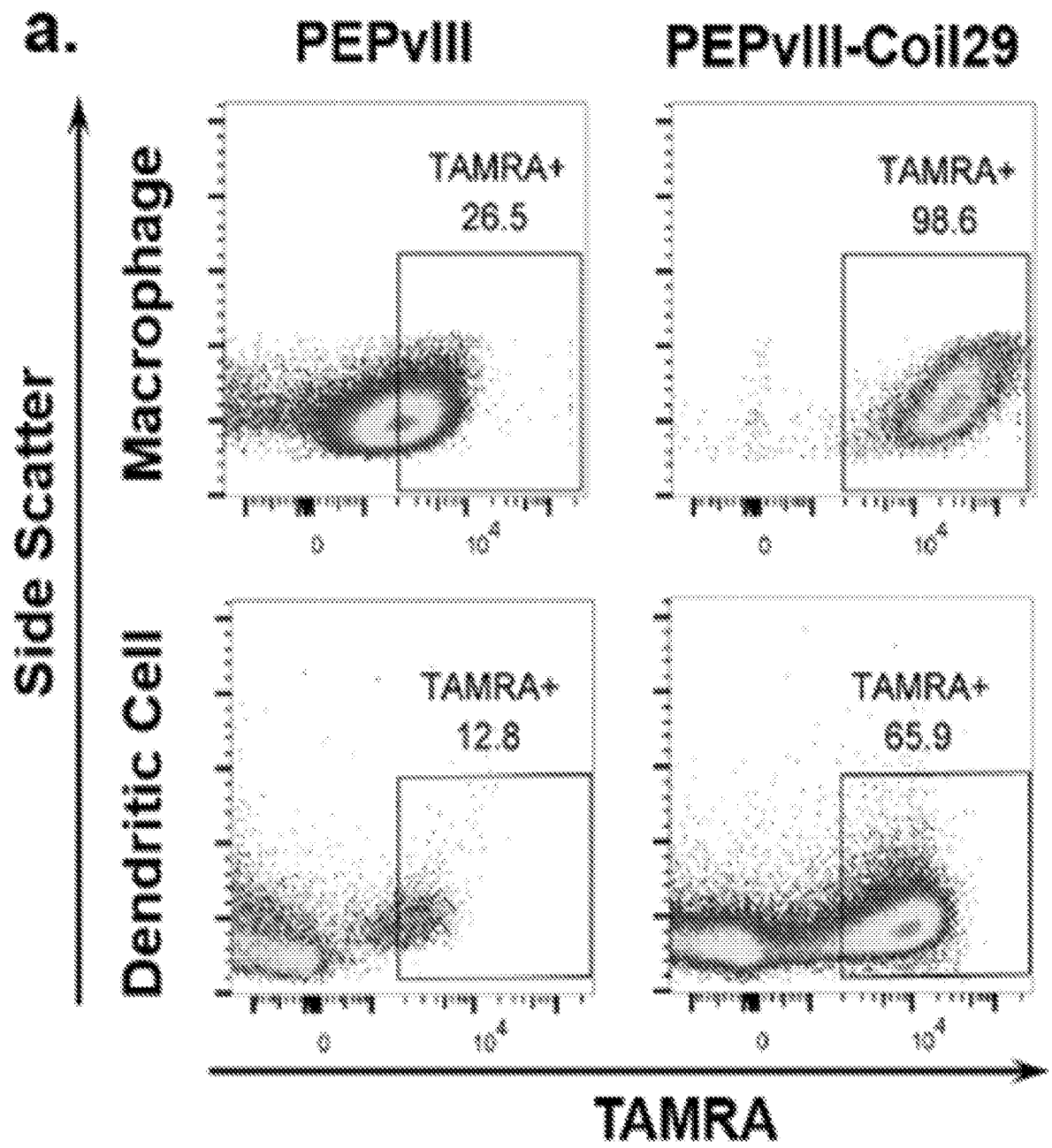
FIGS. 8A-8B. PEPvIII-Coil29 nanofibers were efficiently internalized by antigen presenting cells (APCs) in vivo.
Figure 8B:
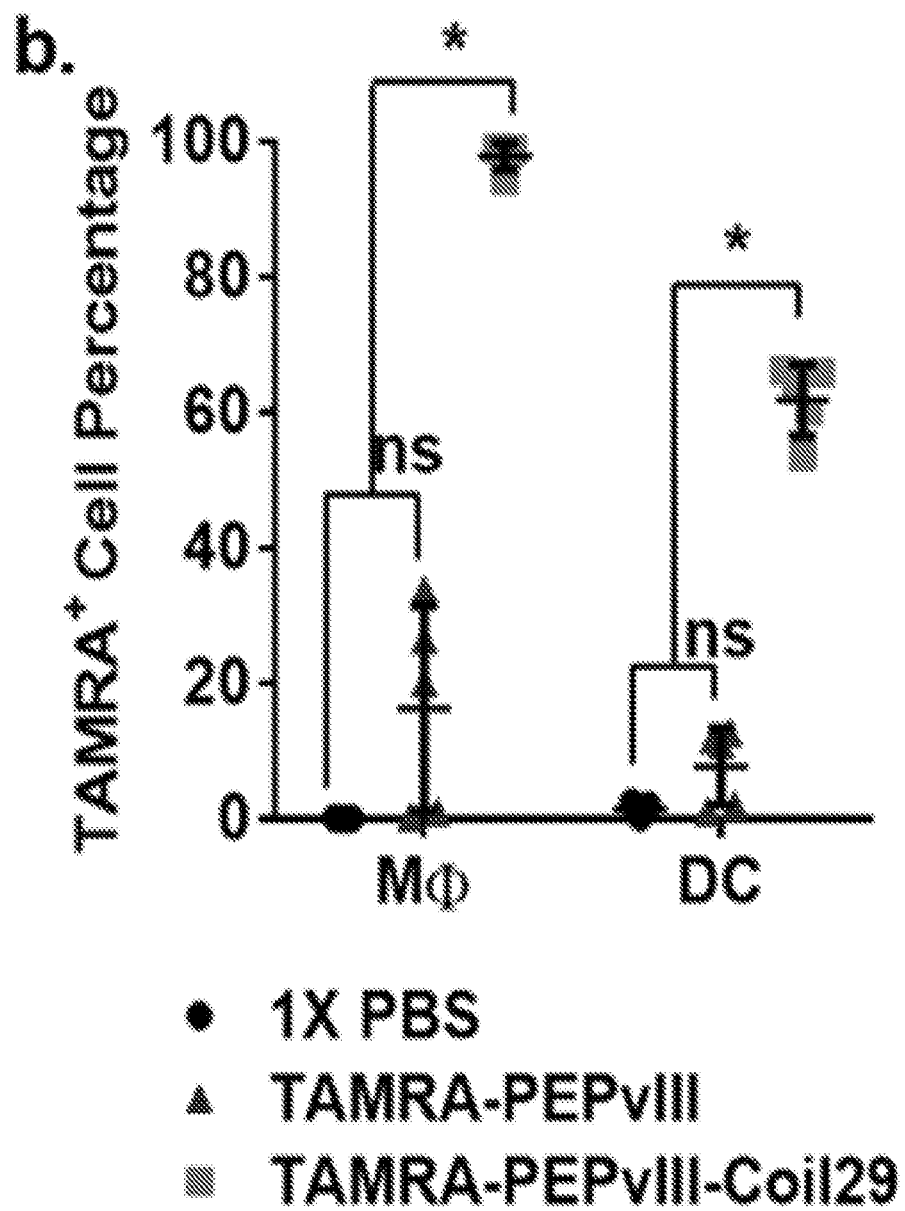
Figure 17:
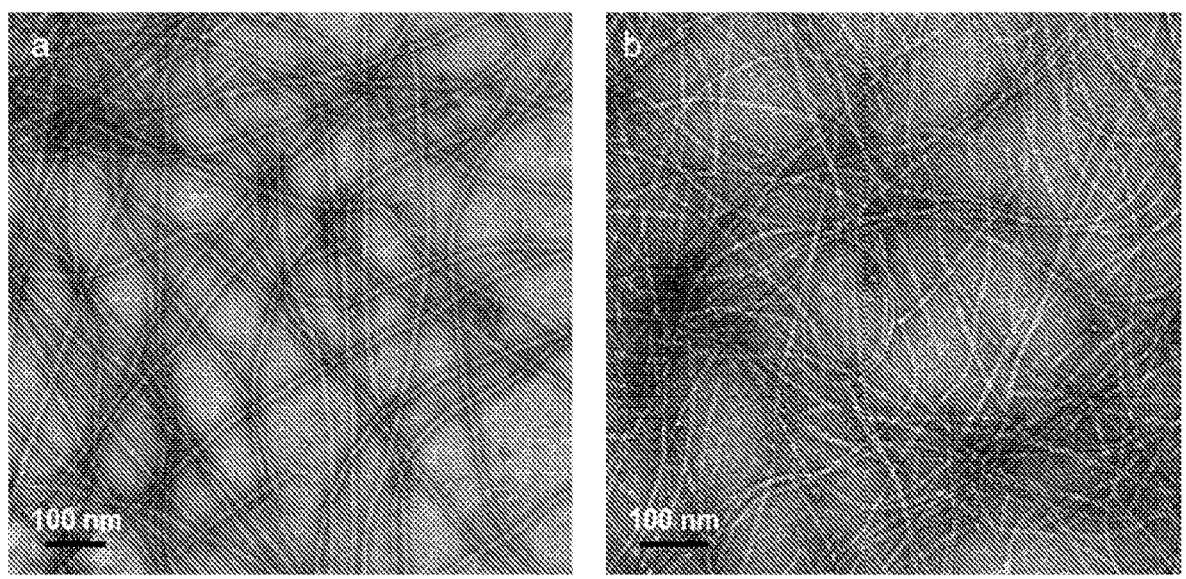
FIG. 17A-17B: TAMRA labeled PEPvIII-Coil29 peptide self-assembled into nanofibers with morphology similar to PEPvIII-Coil29 fibers.
Figure 18:
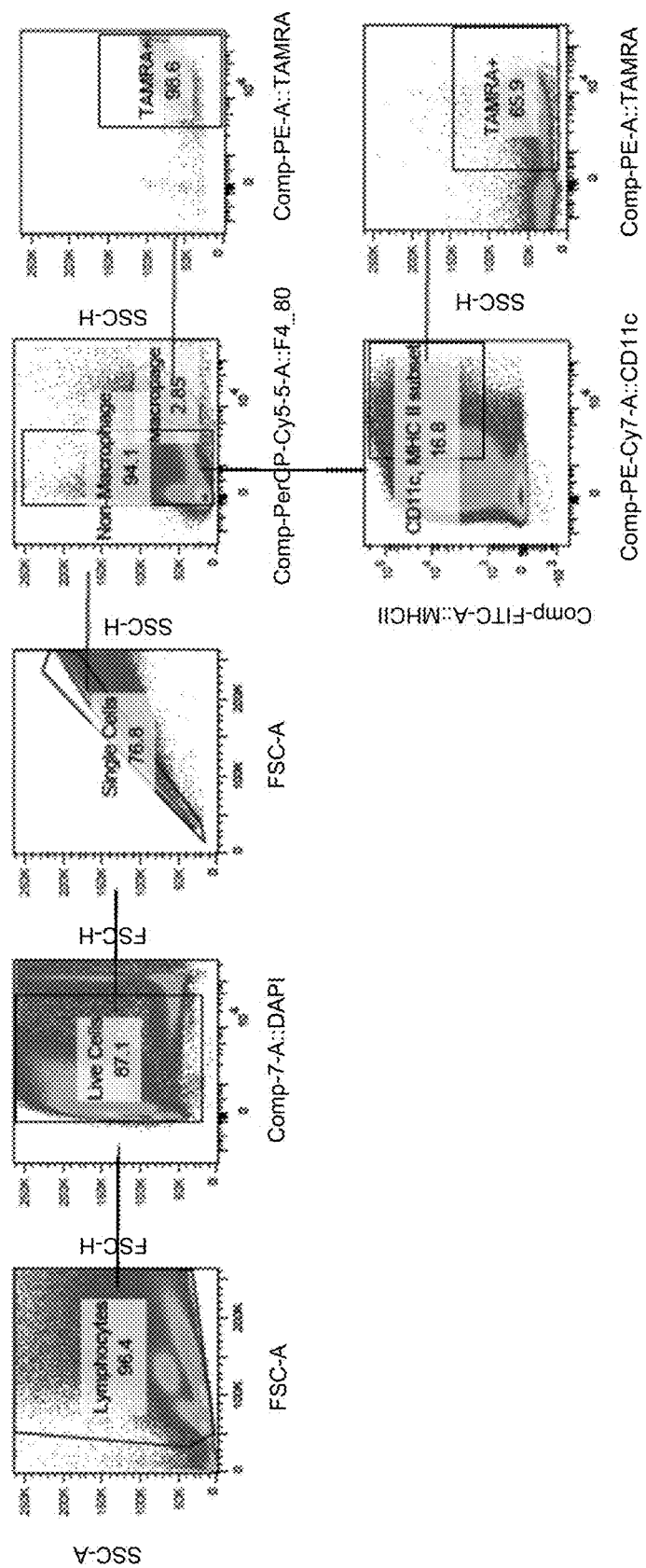
FIG. 18: Representative gating strategy for analyzing the dendritic cells and macrophages via flow cytometry.

To examine whether the epitope-bearing nanofibers could be internalized by APCs, C57BL/6 mice were immunized via i.p. injection with 1×PBS, or PEPvIII or P-C peptides fluorescently labelled with TAMRA (FIG. 8). The TAMRA modification did not alter the nanofiber morphology, according to TEM imaging (FIG. 17). The peritoneal lavage fluid was collected 20 h after injections, to analyze for the percentage of TAMRA positive DCs (CD11c$^+$MHCII$^+$F4/80$^-$) and MΦ (CD11c$^-$F4/80$^+$) using flow cytometry (FIG. 18). The uptake of soluble PEPvIII peptides by dendritic cells and macrophages was statistically indistinguishable from the 1×PBS negative control group. In contrast, about 98% of macrophages and 65% of dendritic cells exhibited TAMRA signal when the mice were immunized with TAMRA labeled P-C fibers, indicating that the self-assembled P-C peptide fibers significantly facilitated the uptake of epitopes by APCs relative to soluble epitopes.

Figure 9:
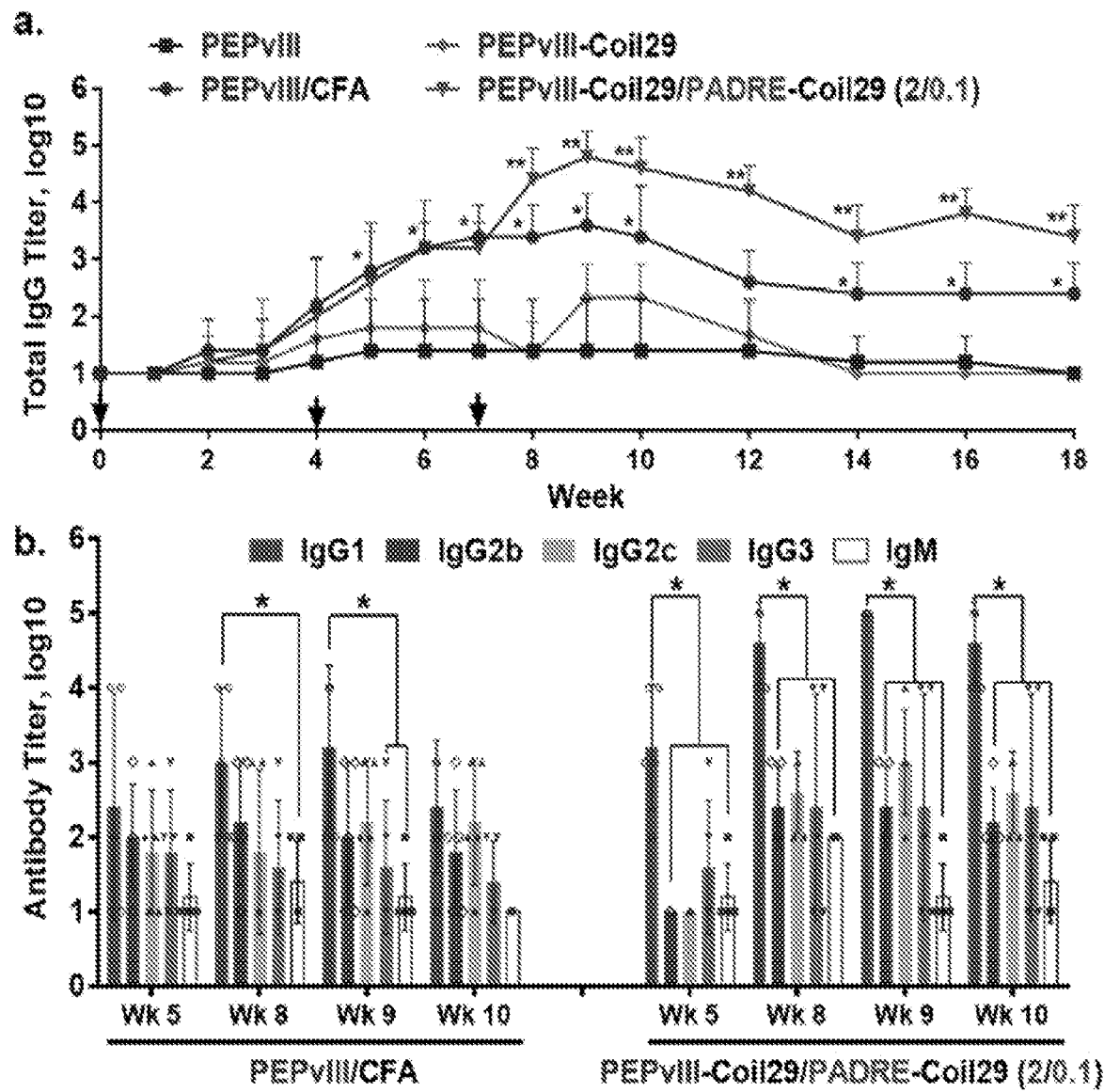
FIGS. 9A-9B: The Coil29 platform elicits strong PEPvIII epitope-specific antibody responses.
Figure 19:
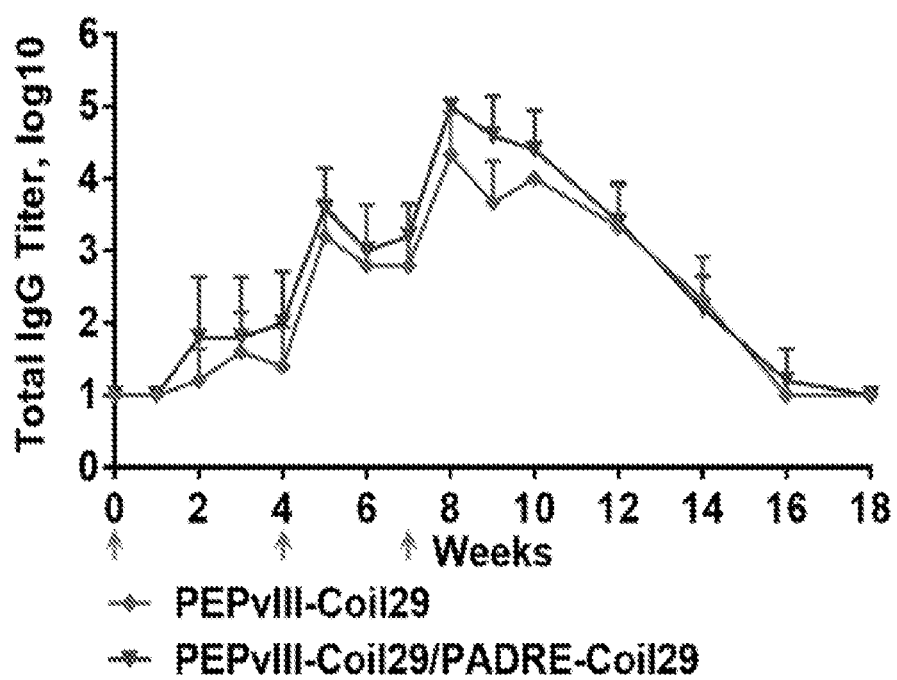
FIG. 19: SGSG-Coil29 specific antibody responses were elicited by self-assembled Coil29 platform. Two boosts containing half primary immunization dose were administrated on week 4 and week 7 after primary injection (N=5 mice per group).

We subsequently investigated the immunogenicity of the Coil29 peptide platform. Four groups of C57BL/6 mice were immunized subcutaneously with same amount of epitope peptides (2×10$^{-3}$M of PEPvIII epitopes, 100 μL per mouse) on week 0, and boosted twice with half of the primary doses (2×10$^{-3}$M of PEPvIII epitopes, 50 μL per mouse) at weeks 4 and 7. Mice primed with an emulsion of PEPvIII with complete Fruend's adjuvant (CFA), and boosted with PEPvIII and incomplete Fruend's adjuvant (IFA) served as a positive control. Sera were collected from all the groups at predesignated dates over 18 weeks, and analyzed for peptide-specific antibody titers via ELISA (FIG. 9). Consistent with the aforementioned uptake results, soluble PEPvIII peptide alone failed to elicit any antibody response during the study, while mice immunized with PEPvIII/CFA exhibited high levels of IgG, with the antibody titer level plateauing at over 10$^3$ following the second boost week 7. After week 10, the antibody titer slightly decreased about 10-fold over a 4 week period, and then maintained at a steady titer level of 10$^2$ afterward. While P-C alone was unable to raise a significant level of epitope-specific IgG antibody titer, the antibody response in mice immunized with the P-C/P nanofiber exhibited a kinetics similar to the CFA adjuvanting group (PEPvIII/CFA) over the initial 7 week period, with the antibody titer reaching 10$^3$ at week 7. Strikingly, the second boost at week 7 elevated the antibody titer nearly 100-fold, with the highest titer level reaching about 10$^5$ at week 9. Despite the gradual decline after week 9, the antibody level elicited by P-C/P nanofibers remained significantly higher than all other groups throughout the remaining duration of the study. The considerable difference in antibody response between P-C and P-C/P groups underlined the importance of the T cell epitope (PADRE) in promoting antibody responses with the Coil29 platform. We have previously established that co-assembling the PADRE epitope within peptide nanofibers can provide T cell help to generate antibody responses against B-cell epitopes. As the PEPvIII peptide lacks an inherent T cell epitope, the inclusion of the PADRE sequence was essential to promote T cell help, and significantly improved the magnitude of IgG production. Antibody isotype analysis revealed that P-C/P fibers also altered the immune phenotype in comparison with the adjuvanting group. (FIG. 9B) For the 4 different weeks examined (week 5, 8, 9, and 10), P-C/P peptide fiber prompted significantly higher IgG1 response over all other four isotypes, while antibody response elicited by CFA only exhibited slight bias toward IgG1 at week 8 and week 9 after the second boost injection on week 7. The IgG1 polarization suggests that the P-C/P fiber favored the Th2 response. The elevated level of IgG1 responses potentially could be beneficial, as IgG1 monoclonal antibodies were found to be more potent in mediating tumor cell killing via the mechanisms of antibody-dependent cellular cytotoxicity (ADCC) and complement-dependent cytotoxicity (CDC) in humans than other antibody isotypes. Interestingly, mice in P-C and P-C/P groups also exhibited humoral responses against the SGSG-Coil29 sequence, but the antibody response gradually diminished to a negligible level after the total IgG titers peaked at week 9 (FIG. 19).

Figure 10:
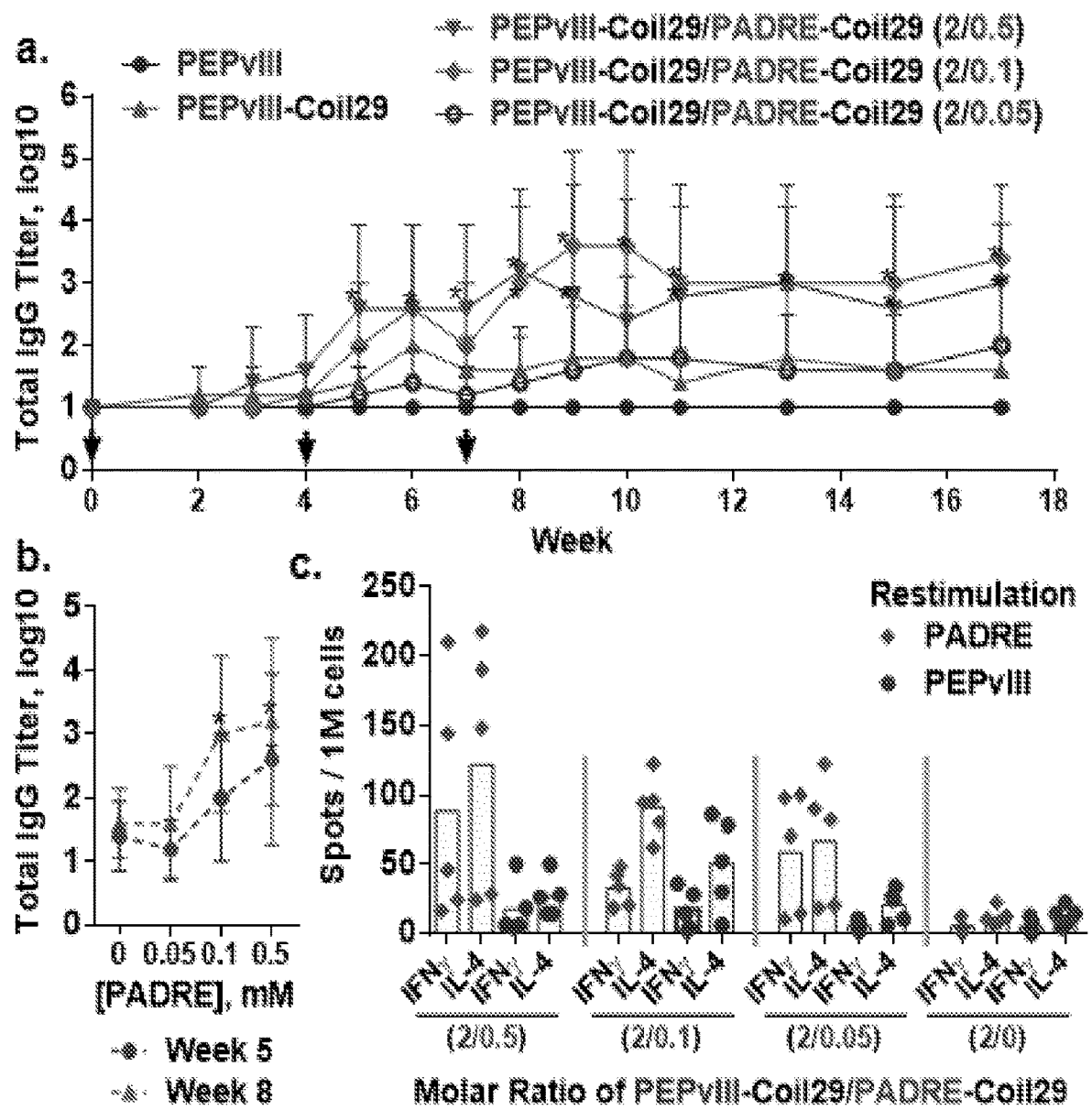
FIGS. 10A-10C: PADRE epitope dosing mediated PEPvIII epitope-specific antibody response.

We further analyzed how the PADRE epitope dosing could impact the humoral response in the current platform (FIG. 10). Four groups of mice were immunized with Coil29 nanofibers formulated with different PADRE epitope concentrations ranging from 0 to 0.5×10$^{-3}$M in final concentration, and the PEPvIII-specific total IgG titers were monitored over 17 weeks (FIG. 10A). The P-C nanofiber alone elicited negligible levels of IgG without T cell epitopes, consistent with our previous results. A slight increase in PADRE dosing within the nanofibers (0.05×10$^{-3}$ M) did not improve the humoral response for the nanofibers as the observed titers were statistically equal between P-C and P-C/P (2/0.05). However, by increasing the PADRE dosing to 0.1×10$^{-3}$M and 0.5×10$^{-3}$ M in final concentration, the antibody production increased to a significantly higher level and the average antibody titers maintained at about 10$^3$ after second boost over the experimental period. Furthermore, the comparison of the antibody response following the boost injections (weeks 5 and 8) revealed the trend that increasing the PADRE dosing led to a gradual increase in IgG response within the tested PADRE dosing range. (FIG. 10B) This observation differed from what we demonstrated in the beta-sheet peptide nanofiber platform, where the antibody response at different PADRE dosing regimens exhibited a bell-shaped curve with the peak response at $0.05$-$0.1 \times 10^{-3}$ M of PADRE epitopes. However, the difference in antibody response in relationship with PADRE dosing could possibly be caused by several reasons, including the use of a different B cell epitope. We are currently investigating the mechanism of this observation. It highlighted the significance in future application where the formulation of nanofibers should be fine-tuned for different epitopes induce optimal response. When T cell response was measured using ELISPOT, it was found to be specific to T cell epitope, PADRE. (FIG. 10C) Splenocytes collected from the mice in the P-C group responded to neither PADRE peptide nor PEPvIII peptide. Moreover, T cells from mice immunized with nanofibers containing higher doses of PADRE had correspondingly higher levels of of IFNγ and IL4 secretion. Stimulation with PEPvIII peptides elicited only very low levels of cytokine secretion. These results are consistent with our previous results, underlining the role of T cells in the antibody response against the PEPvIII epitope.

Figure 11:
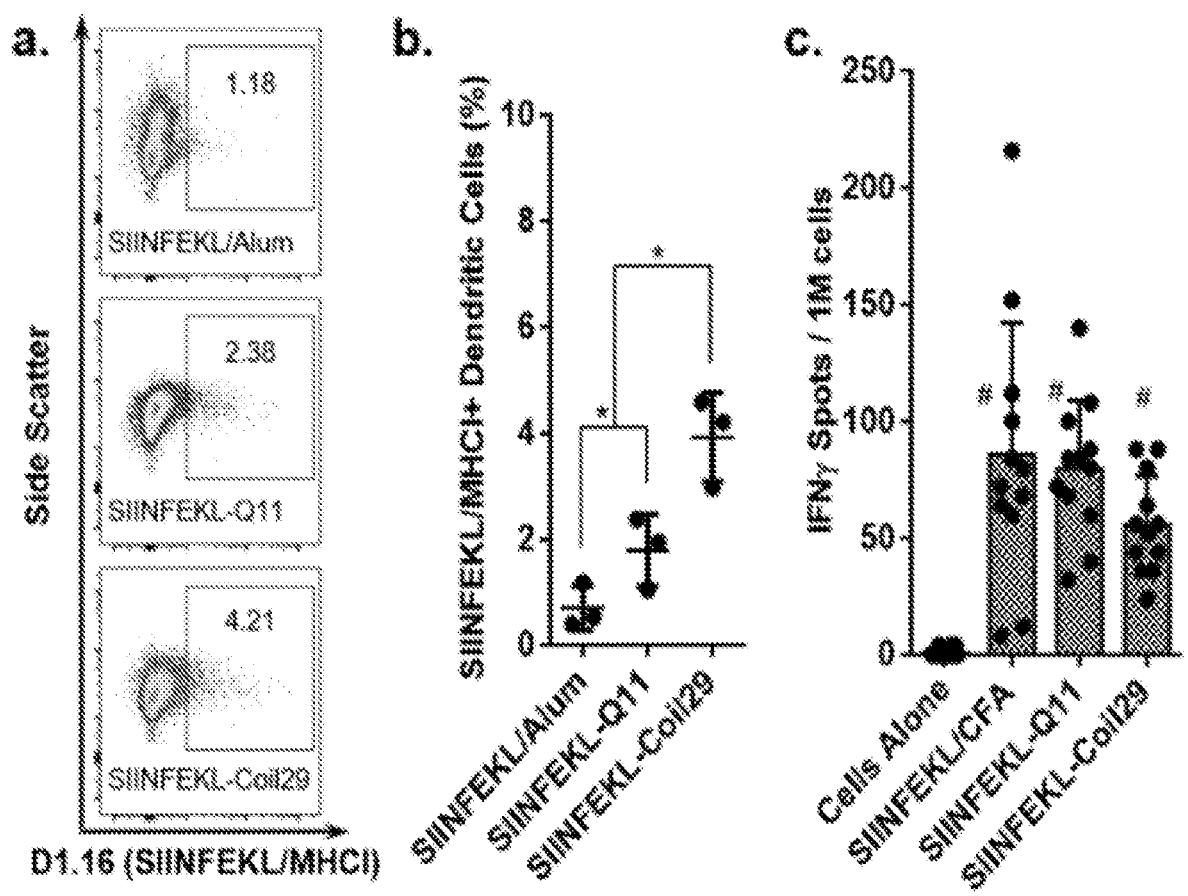
FIGS. 11A-11C. SIINFEKL-Coil29 nanofibers were efficiently presented by dendritic cells in vivo.

Finally, we examined the Coil29 peptide's ability to deliver a CD8+ T cell epitope. The model epitope SIINFEKL was covalently linked to Coil29 via an AAYGG linker through N-terminal extension. It was previously shown that Q11 can elicit robust CD8+ T cell responses. Compared with Q11, when introduced by Coil29 platform, the SIINFEKL epitope could be more efficiently presented by DCs 20 h after i.p. injection, whereas about 4.1% of dendritic cells were found to be SIINFEKL-presenting cells. To determine whether immunization with peptide nanofibers could lead to proper immune cell functions, IFNγ ELISPOTs were performed on splenocytes harvested from mice three weeks after primary injections. When restimulated with SIINFEKL peptides, Coil29 and Q11 platforms elicited a comparable level of immune cell IFNγ secretion to that of SIINFEKL/CFA group (FIG. 11).

In summary, we designed a vaccine delivery platform based on a self-assembling α-helical coiled-coil peptide fiber. The epitope modification did not significantly impact the self-assembly process. It was established that Coil29 nanofibers could be efficiently internalized by APCs. Peptide nanofibers incorporating a CD4+ T cell epitope, PADRE, were capable of eliciting durable PEPvIII epitope specific antibody responses that were even higher than a CFA adjuvanted formulation, while the B cell epitope bearing fiber alone failed to promote humoral responses. IgG1 titers elicited by P-C/P were significantly higher when compared with the CFA adjuvanted group, indicating that higher level of Th2 polarization promoted by nanofiber. Additionally, increasing the PADRE epitope dosing within the fibers was shown to gradually enhance the antibody production T cell responses were found to be PADRE specific and the response level was also tuned by the dosing of PADRE epitope. The ability of the Coil29 platform to elicit CD8+ T cell responses was also shown to be comparable to CFA emulsion. This represents the first example of using coiled-coil peptide fibers as a self-adjuvanting vaccine delivery platform.

Example 4

Coil29 Compared to Q11

OVA epitope (ISQAVHAAHAEINEAGR, SEQ ID NO: 22) was linked with Coil29 and Q11 peptide platform via a SGSG linker. This modification did not alter the nanofiber formation as characterized via TEM imaging (FIG. 12A and FIG. 12B). The morphologies of OVA-Coil29 and OVA-Q11 are similar to each other.

Figure 13:
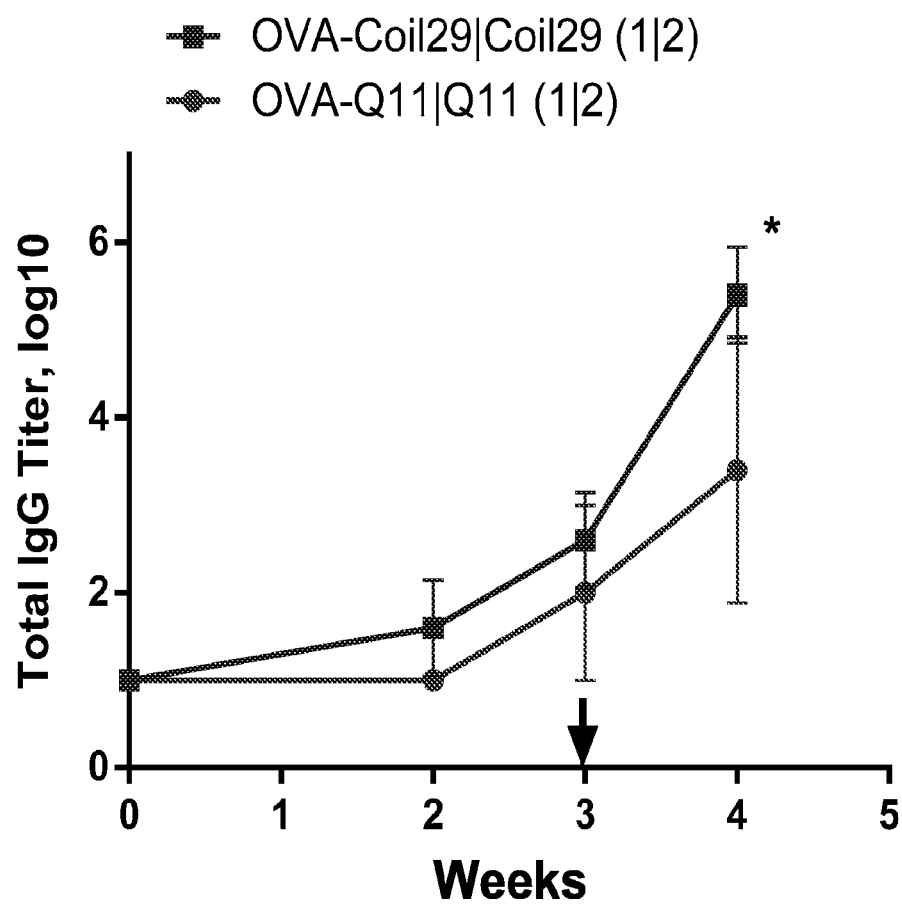
FIG. 13: Graph of time versus total IgG titer, showing the OVA specific antibody production comparison between Coil29 and Q11 (n=5).

A group of mice was immunized on week 0 with 100 μL of 2 mM each nanofiber in PBS with the epitope concentration 0.67 mM, and received boost injections that is half the dose of primary injections. The OVA specific antibody response was measured via ELISA assay. At week 3, the average antibody titer for both groups was around $10^2$. After the boost on week 3, the antibody response was significantly elevated in the Coil29 group, yielding the total IgG titer to be over $10^5$, which is significantly higher than the average IgG concentration elicited by OVA-Q11, $10^3$, with a p value <0.0001 (FIG. 13).

Figure 14:
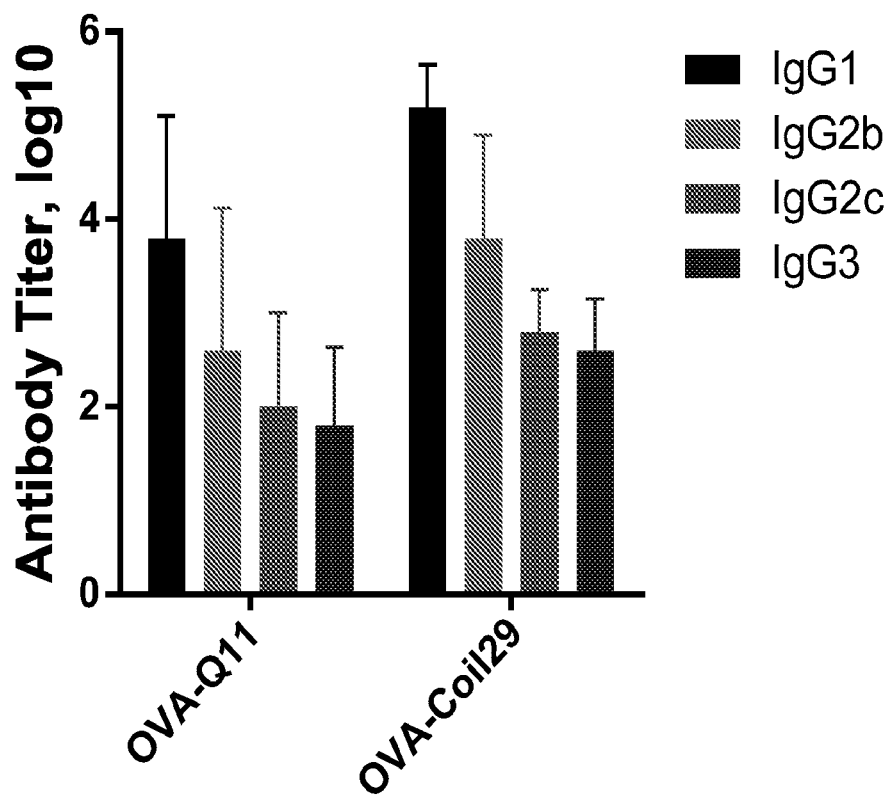
FIG. 14: Graph of antibody titers, showing OVA specific antibody isotypes distribution on week 4.

ELISA assay was carried out to analyze the OVA-specific antibody isotypes on week 4. With similar distribution profile, OVA-Coil29 nanofibers elevated the response on all 4 isotypes relative to OVA-Q11 (FIG. 14). These results revealed that Coil29 platform elevated the antibody responses significantly without biased toward a specific isotype as compared with Q11.

Example 5

Coil23

Figure 15:
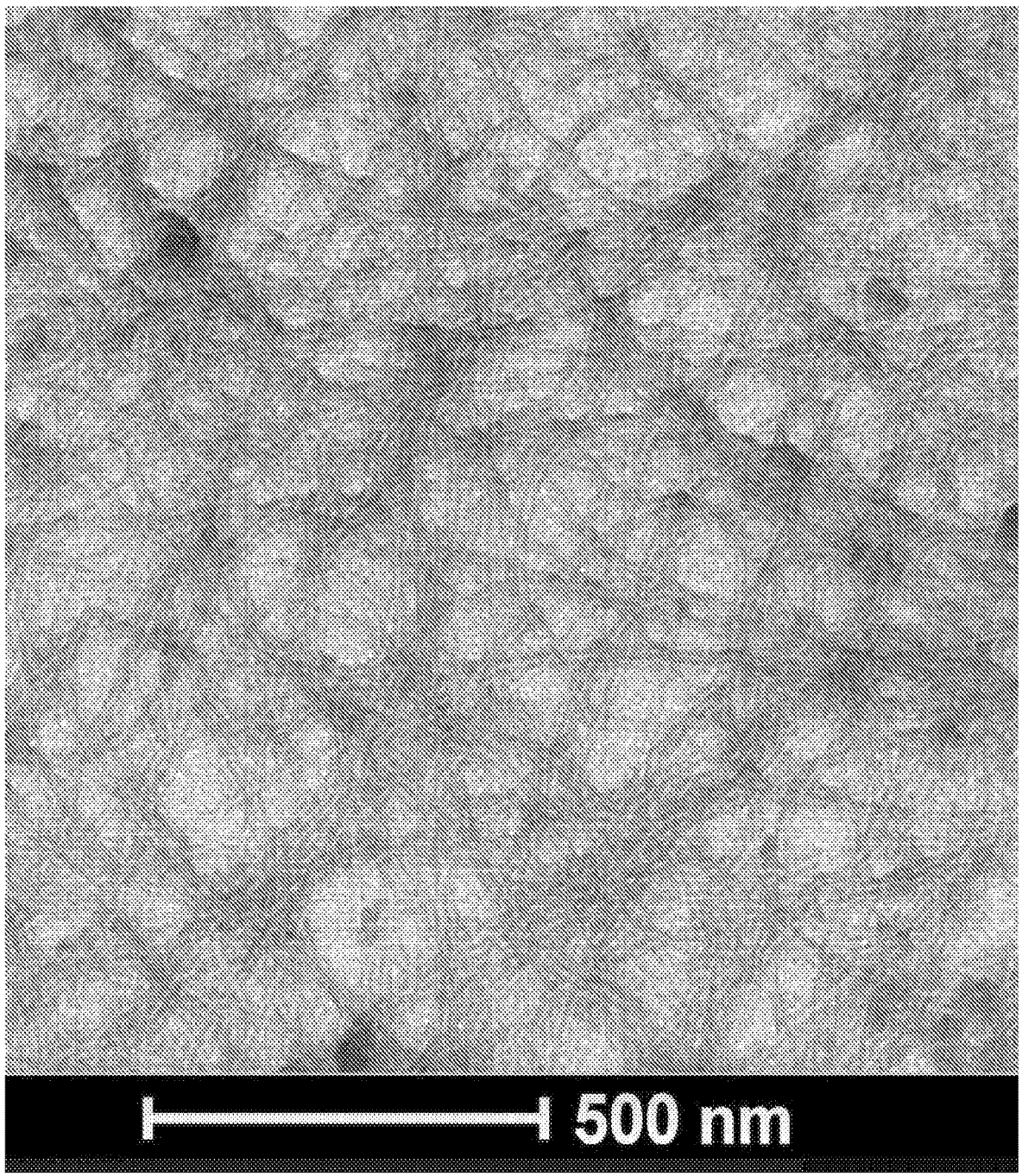
FIG. 15: TEM image of Coil23 peptide fibrils.
Figure 16A:
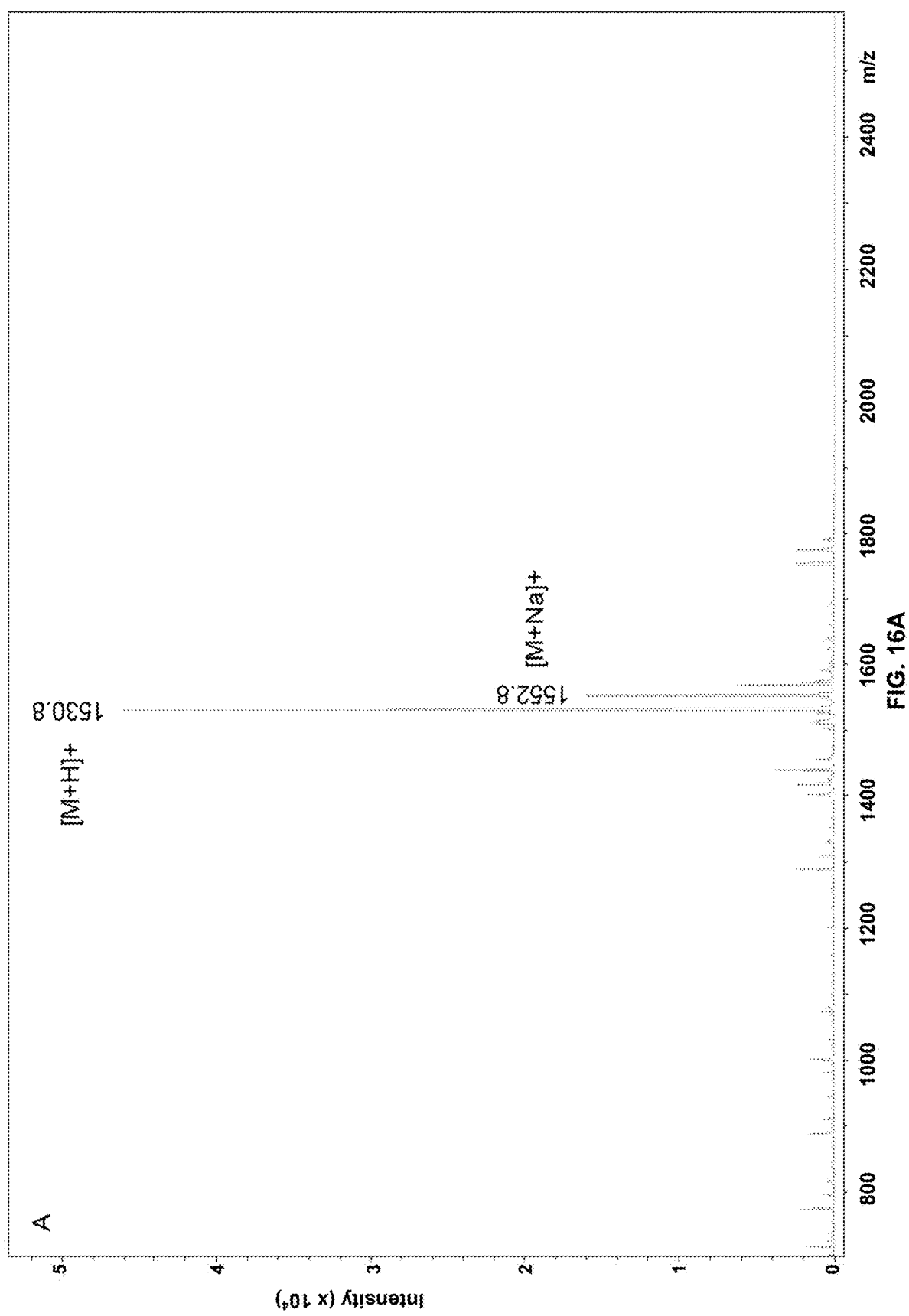
FIG. 16A-16G: MALDI spectra of all the peptides after purified by HPLC.
Figure 16B:
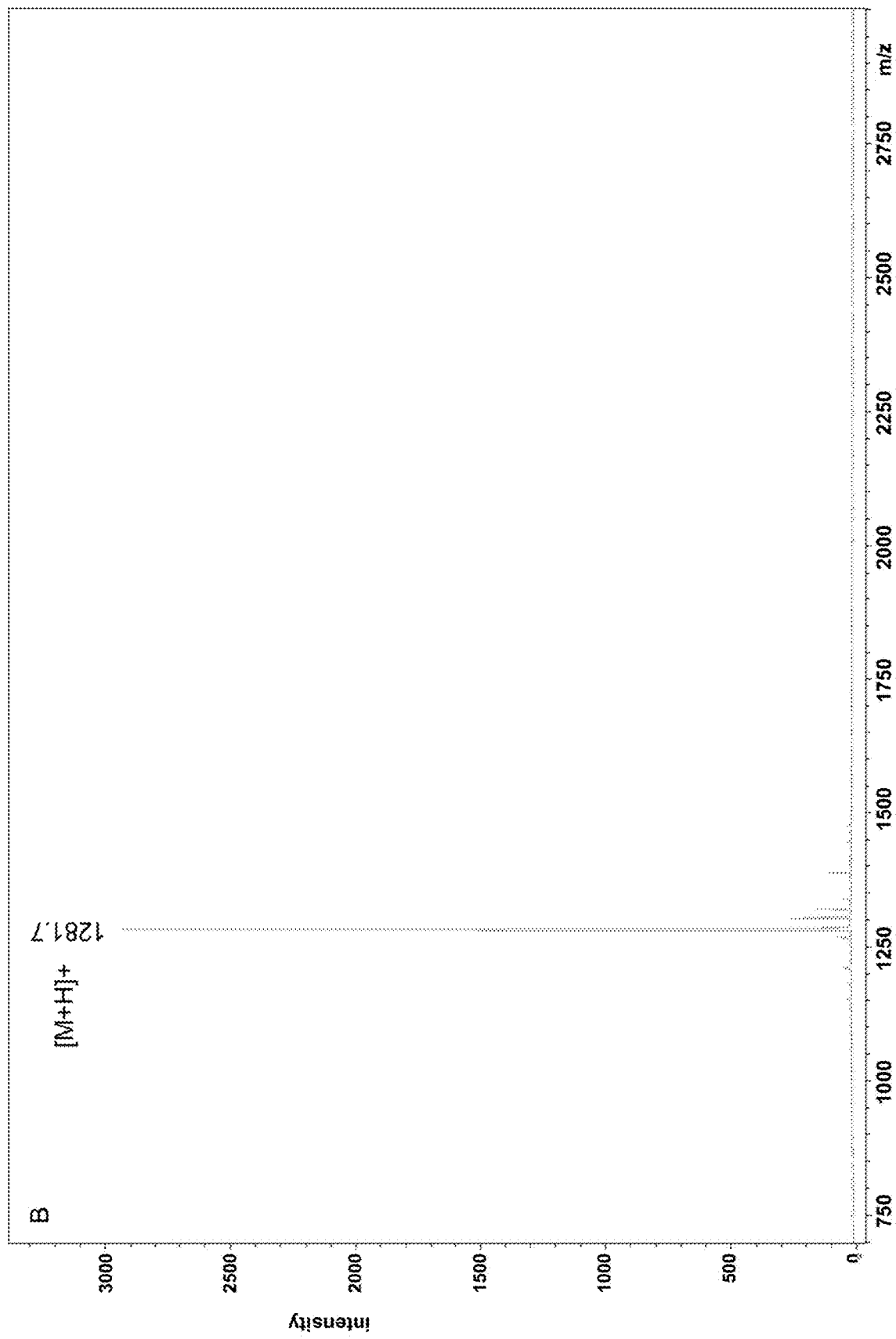
Figure 16C:
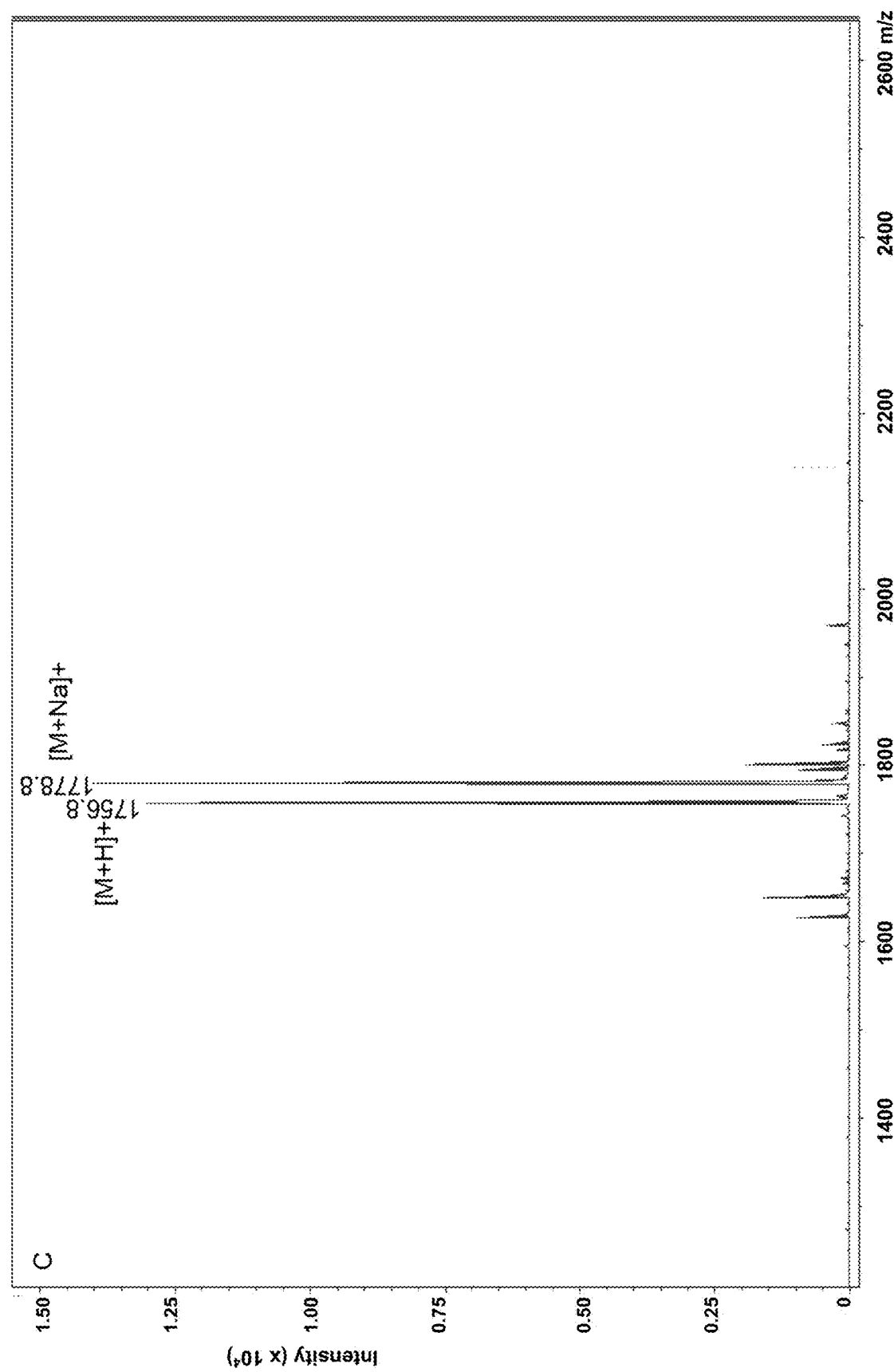
Figure 16D:
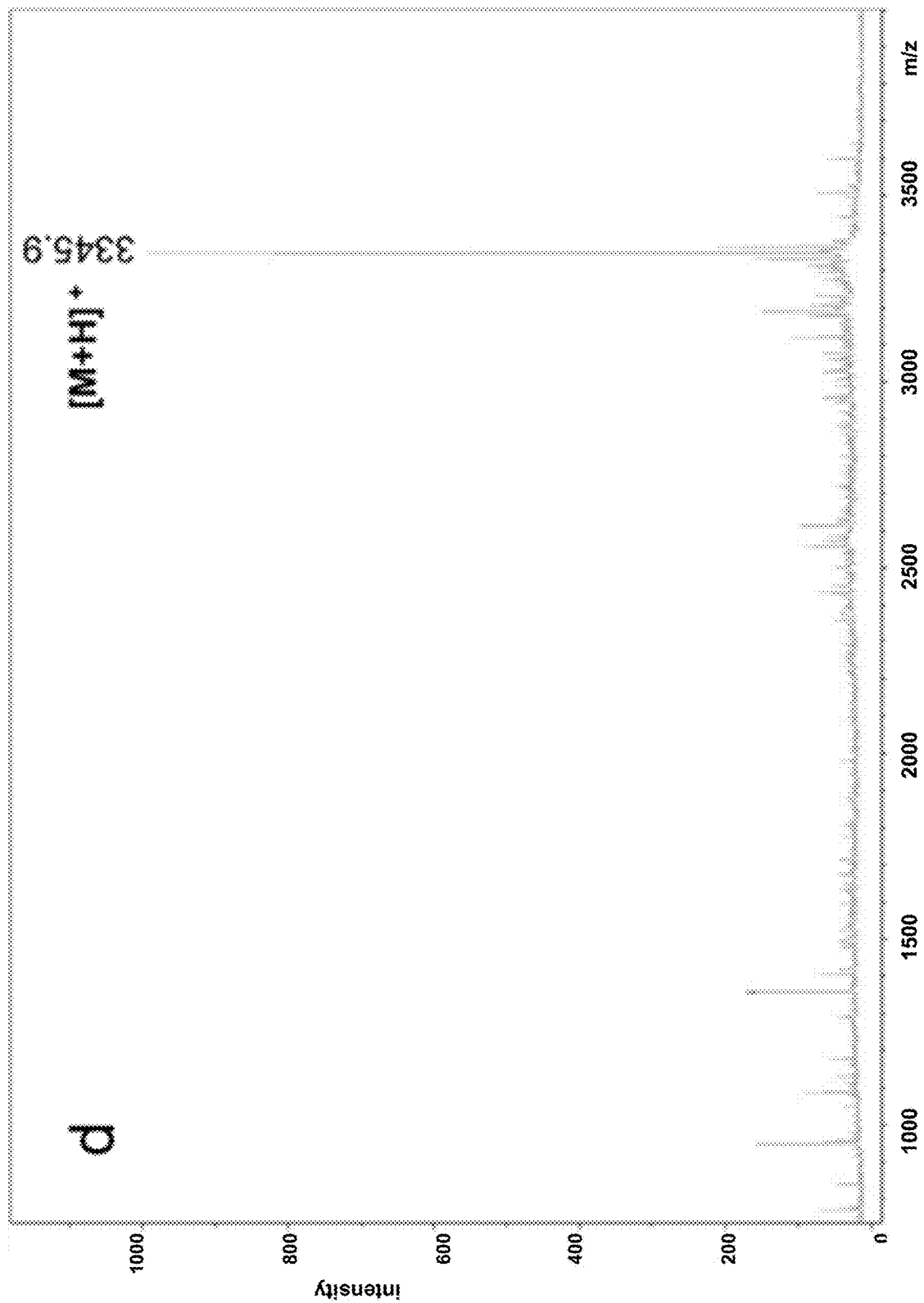
Figure 16E:
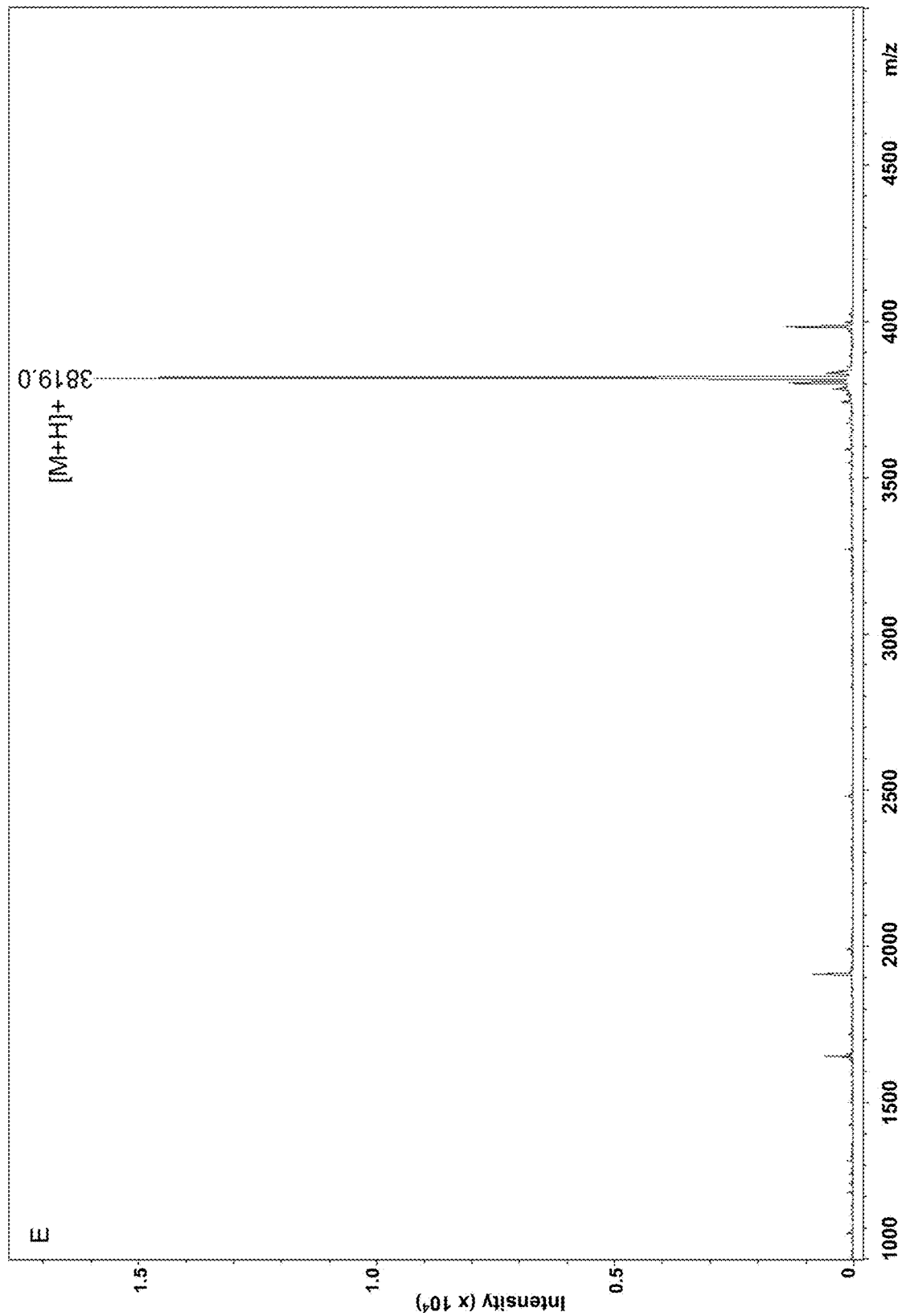
Figure 16F:
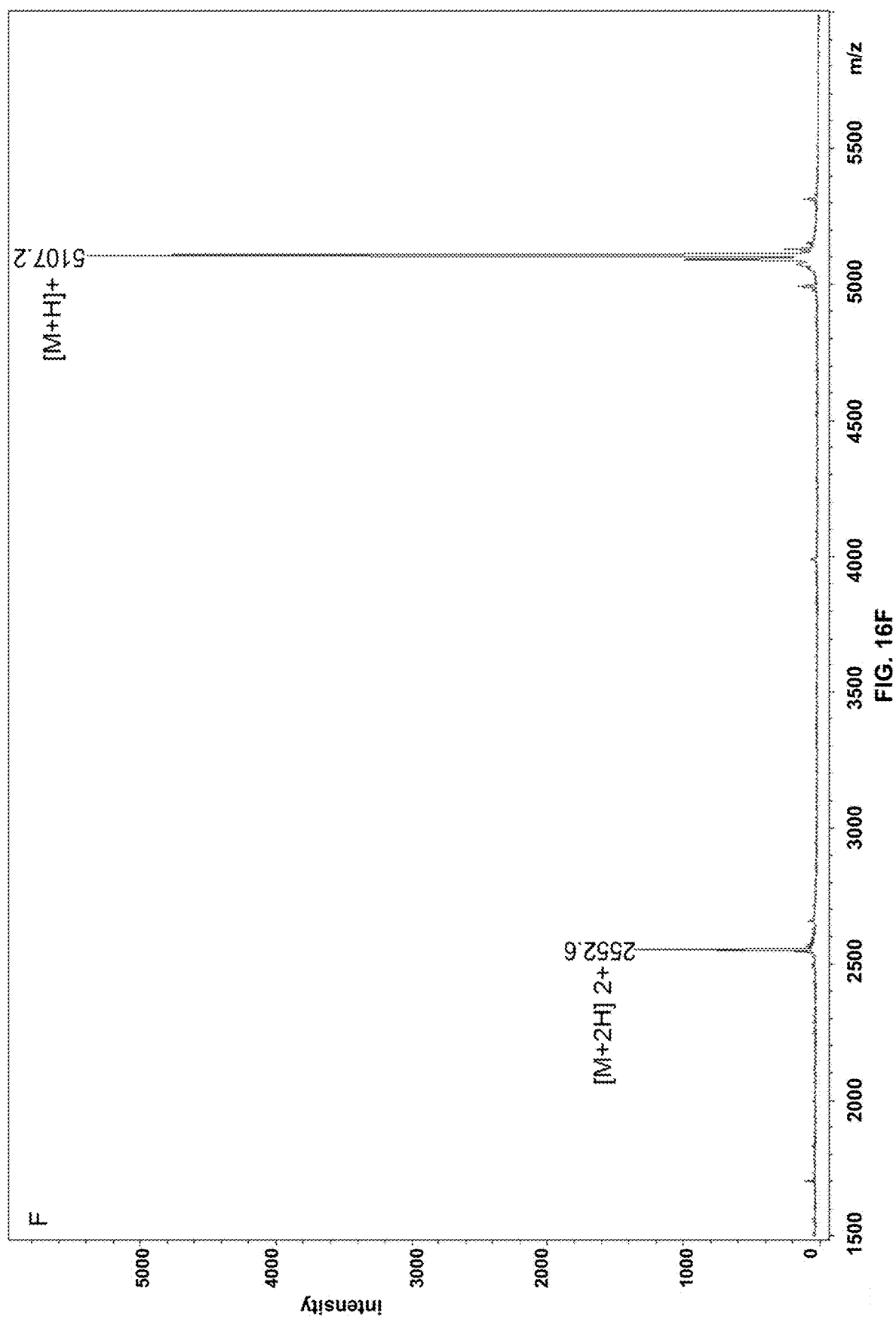
Figure 16G:
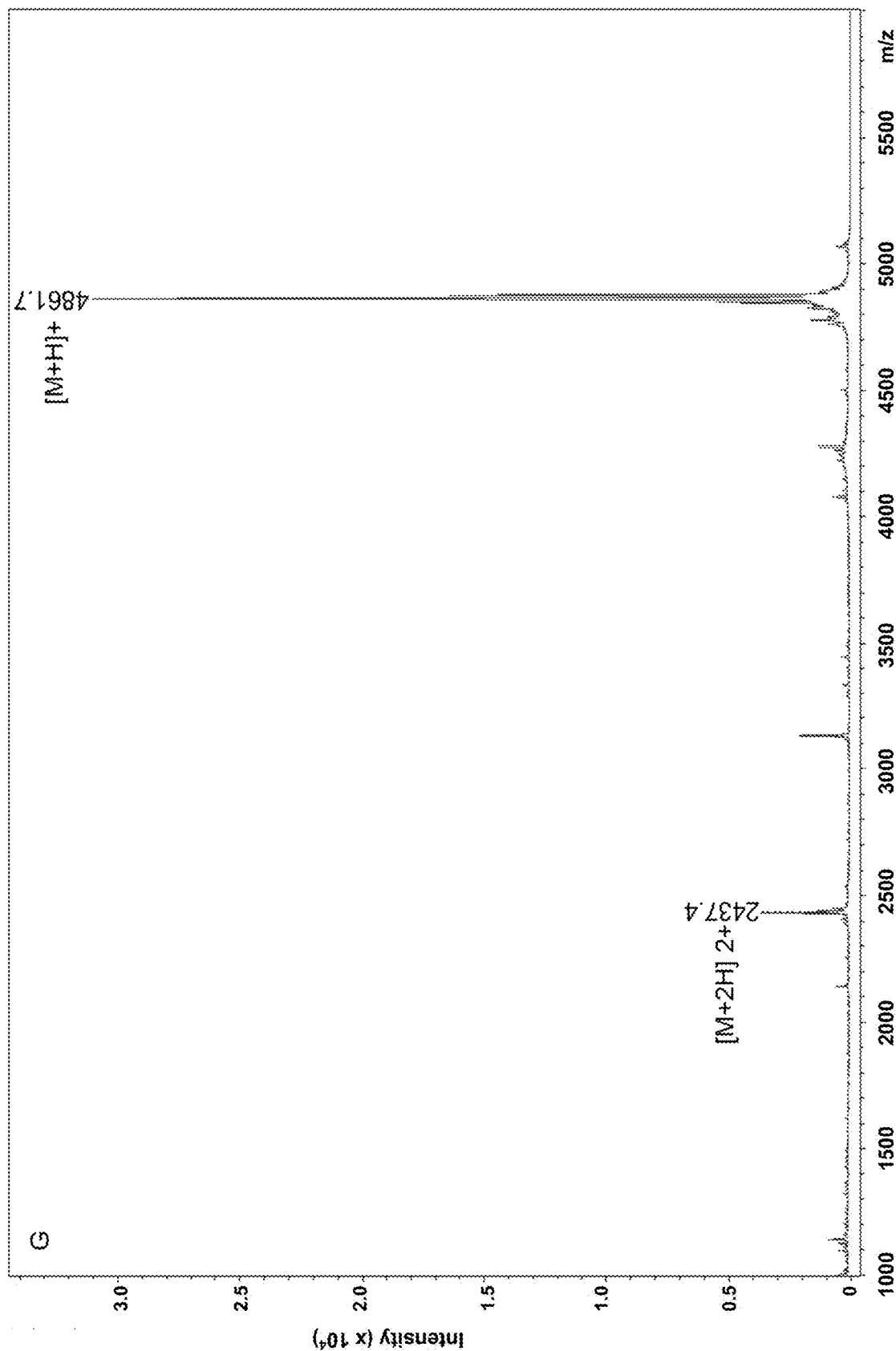

Coil23 self-assembling peptide was generated, with the sequence ADAEILRAYARILEAHAEILRAQ (SEQ ID NO: 8). TEM confirmed Coil23 forms helical filaments (FIG. 15).

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. An immunogenic composition comprising a peptide fibril coupled to a plurality of antigens, wherein the peptide fibril comprises a plurality of alpha helices.

Clause 2. The composition of clause 1, wherein the peptide fibril comprises a plurality of self-assembling peptides, wherein each self-assembling peptide forms an alpha-helix.

Clause 3. The composition of clause 1 or 2, wherein the peptide fibril has a coiled coil structure.

Clause 4. The composition of clause 1 or 2, wherein the peptide fibril has a structure of a helical filament formed around a central axis.

Clause 5. The composition of clause 4, wherein the N-terminus of each self-assembling peptide is positioned at the exterior of the helical filament.

Clause 6. The composition of any one of the previous clauses, wherein the self-assembling peptide is conjugated to an antigen.

Clause 7. The composition of any one of the previous clauses, wherein each self-assembling peptide is conjugated to an antigen.

Clause 8. The composition of any one of the previous clauses, wherein the antigen is covalently coupled to the self-assembling peptide.

Clause 9. The composition of any one of the previous clauses, wherein the antigen is covalently coupled to a terminus of the self-assembling peptide.

Clause 10. The composition of clause 9, wherein the antigen is covalently coupled to the N-terminus of the self-assembling peptide.

Clause 11. The composition of any one of the previous clauses, wherein the antigens are exposed on the exterior surface of the peptide fibril.

Clause 12. The composition of any one of clauses 4-11, wherein the antigens are exposed on the exterior surface of the helical filament of the peptide fibril.

Clause 13. The composition of any one of the previous clauses, wherein the antigen is selected from a small molecule, nucleotide, polynucleotide, peptide, polypeptide, protein, lipid, carbohydrate, and a combination thereof.

Clause 14. The composition of clause 13, wherein the antigen comprises a peptide.

Clause 15. The composition of clause 14, wherein the peptide is 5 to 35 amino acids in length.

Clause 16. The composition of clause 13, wherein the antigen is comprises a small molecule.

Clause 17. The composition of clause 13, wherein the antigen is comprises a cytokine.

Clause 18. The composition of any one of the above clauses, wherein the peptide fibril comprises at least two different antigens.

Clause 19. The composition of any one of the above clauses, wherein the peptide fibril comprises self-assembling peptides not conjugated to the antigen and self-assembling peptides conjugated to the antigen, and wherein the peptide fibril comprises at least two different antigens.

Clause 20. The composition of any one of the above clauses, wherein the plurality of antigens comprises a B cell epitope, or T cell epitope, or a combination thereof.

Clause 21 The composition of clause 20, wherein the plurality of antigens comprises a B cell epitope and a T cell epitope.

Clause 22. The composition of any one of the above clauses, wherein the peptide fibril is non-toxic.

Clause 23. The composition of any one of clauses 1-22, wherein the self-assembling peptide comprises an amino acid sequence of bXXXb (SEQ ID NO: 1), wherein X is independently any amino acid, and b is independently any positively charged amino acid.

Clause 24. The composition of clause 23, wherein b is independently selected from Arg and Lys.

Clause 25. The composition of clause 23, wherein b is Arg.

Clause 26. The composition of clause 23, wherein bXXXb (SEQ ID NO: 1) is RAYAR (SEQ ID NO: 2).

Clause 27. The composition of clause 23, wherein bXXXb (SEQ ID NO: 1) is KAYAK (SEQ ID NO: 3).

Clause 28. The composition of any one of clauses 1-222, wherein the self-assembling peptide comprises an amino acid sequence of $Z_n bXXXbZ_m$ (SEQ ID NO: 5), wherein b is independently any positively charged amino acid, Z is independently any amino acid, X is independently any amino acid, n is an integer from 0 to 20, and m is an integer from 0 to 20.

Clause 29. The composition of clause 28, wherein n is an integer from 5 to 15, and m is an integer from 5 to 15.

Clause 30. The composition of any one of the above clauses, wherein the self-assembling peptide comprises a glutamine at the C-terminus.

Clause 31. The composition of any one of the above clauses, wherein the self-assembling peptide comprises a glutamine at the N-terminus.

Clause 32. The composition of any one of clauses 1-24 or 28-30, wherein the self-assembling peptide comprises an amino acid sequence selected from

```
                                        (SEQ ID NO: 6)
QARILEADAEILRAYARILEAHAEILRAQ,
or
                                        (SEQ ID NO: 7)
QAKILEADAEILKAYAKILEAHAEILKAQ,
or
                                        (SEQ ID NO: 8)
ADAEILRAYARILEAHAEILRAQ.
```

Clause 33. The composition of clause 32, wherein the self-assembling peptide comprises an amino acid sequence of QARILEADAEILRAYARILEAHAEILRAQ (SEQ ID NO: 6).

Clause 34. The composition of clause 32, wherein the self-assembling peptide comprises an amino acid sequence of QAKILEADAEILKAYAKILEAHAEILKAQ (SEQ ID NO: 7).

Clause 35. The composition of clause 32, wherein the self-assembling peptide comprises an amino acid sequence of ADAEILRAYARILEAHAEILRAQ (SEQ ID NO: 8).

Clause 36. The composition of any one of the previous clauses, wherein the self-assembling peptide further comprises a linker between the antigen and self-assembling peptide.

Clause 37. The composition of clause 36, wherein the linker comprises oligoethylene glycol, polyethylene glycol, or an amino acid sequence selected from SEQ ID NO: 9 ($G_n$ wherein n is an integer from 1 to 10), SEQ ID NO: 10 (SGSG), SEQ ID NO: 11 (GSGS), SEQ ID NO: 12 (SSSS), SEQ ID NO: 13 (GGGS), SEQ ID NO: 14 (GGC), SEQ ID NO: 15 ($(GGC)_8$), and SEQ ID NO: 16 ($(G_4S)_3$).

Clause 38. The composition of clause 36 or 37, wherein the antigen is attached to the self-assembling peptide through a thiol reactive group in the linker.

Clause 39. The composition of any one of the previous clauses, wherein the peptide fibril is at least 250 nanometers in length.

Clause 40. The composition of any one of the previous clauses, wherein the composition further comprises an adjuvant.

Clause 41. The composition of any one of the previous clauses, wherein the composition does not further comprise an adjuvant.

Clause 42. The composition of any one of the previous clauses, wherein the peptide fibril is an adjuvant.

Clause 43. The composition of any one of the previous clauses, wherein the self-assembling peptide is synthesized by a solid phase peptide synthesis.

Clause 44. A method of inducing an antigen-specific immune response in a subject comprising administering to the subject the immunogenic composition of any one of clauses 1-43 in an amount sufficient to induce an immune response and antigen-specific immunity.

Clause 45. The method of clause 44, wherein the immunogenic composition is administered to the subject intravenously, intraarterially, intraperitoneally, subcutaneously, intranasally, intramuscularly, or intratumorally.

Clause 46. The method of clause 44 or 45 wherein the immune response is an antigen-specific immune response.

Clause 47. The method of any one of clauses 44-46, wherein the antigen-specific immune response is temporary or not life-long.

Clause 48. The method of any one of clauses 44-47, wherein the immune response comprises IgG1 antibody isotypes.

Clause 49. The method of any one of clauses 44-48, wherein the immunogenic composition has increased immunogenicity relative to a control.

Clause 50. The method of clause 49, wherein the control comprises the antigen without a self-assembling peptide.

Clause 51. The method of any one of clauses 44-50, wherein the subject has cancer.

Clause 52. The method of any one of clauses 44-51, wherein the immune response is an anti-cancer immune response.

Clause 53. An antibody produced in the immune response by the method of any one of clauses 44-52.

Clause 54. A method of treating a subject having or at risk of developing a microbial infection or pathological condition comprising administering to the subject an effective amount of a composition of any one of clauses 1-43 or the antibody of clause 53.

Clause 55. The method of clause 54, wherein the pathological condition is cancer or autoimmunity.

Clause 56. A method for making the composition of any one of clauses 1-43, the method comprising: providing a first peptide fibril comprising self-assembling peptides conjugated to a first antigen; providing a second peptide fibril comprising self-assembling peptides conjugated to a second antigen; and mixing together the first and the second peptide fibrils.

Clause 57. A method for making the composition of any one of clauses 1-43, the method comprising: providing a first peptide fibril comprising self-assembling peptides conjugated to an antigen; providing a second peptide fibril comprising self-assembling peptides not conjugated to an antigen; and mixing together the first and the second peptide fibrils.

Clause 58. A method for making the composition of any one of clauses 1-43, the method comprising: providing a first peptide fibril comprising self-assembling peptides conjugated to a first antigen; providing a second peptide fibril comprising self-assembling peptides conjugated to a second antigen; providing a third peptide fibril comprising self-assembling peptides not conjugated to an antigen; and mixing together the first, the second, and the third peptide fibrils.

Clause 59. A method for making the composition of any one of clauses 1-43, the method comprising: providing a first mixture comprising a plurality of self-assembling peptides, each self-assembling peptide conjugated to a first antigen; providing a second mixture comprising a plurality of self-assembling peptides, each self-assembling peptide conjugated to a second antigen; and mixing together the first mixture and the second mixture to form peptide fibrils, each peptide fibril comprising the first and second antigen.

Clause 60. A method for making the composition of any one of clauses 1-43, the method comprising: providing a first mixture comprising a plurality of self-assembling peptides conjugated to an antigen; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen.

Clause 61. A method for making the composition of any one of clauses 1-43, the method comprising: providing a first mixture comprising a plurality of self-assembling peptides conjugated to a first antigen; providing a second mixture comprising a plurality of self-assembling peptides conjugated to a second antigen; providing a third mixture comprising a plurality of self-assembling peptides not conjugated to an antigen; and mixing together the first, the second, and the third mixtures to form peptide fibrils, each peptide fibril comprising the first antigen, the second antigen, and a portion of the self-assembling peptides not conjugated to an antigen.

Clause 62. The method of clause 56, 58, 59, and 61, wherein the first and second antigens are different.

Clause 63. A method for making the composition of any one of clauses 1-43, the method comprising: providing a first mixture comprising a plurality of self-assembling peptides conjugated to one or more antigens; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen.

Clause 64. The method of clause 63, wherein the antigens are the same.

Clause 65. The method of clause 63, wherein the antigens are different.

Clause 66. The method of clause 63, wherein the peptide fibril comprises n different antigens, wherein n is an integer from 1 to 10,000

REFERENCES

The following references, to the extent that they provide exemplary procedural or other details supplementary to those set forth herein, are specifically incorporated herein by reference.

U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 6,651,655
U.S. Pat. No. 6,733,754
U.S. Pat. No. 6,793,923

Aggeli et al., *Nature*, 386:259-262, 1997.
Bettahi et al., *Cancer Immunol. Immunother.*, 58:187-200, 2009.
Cao et al., *Neurosci.*, 9:25, 2008.
Collier and Messersmith, *Bioconjug. Chem.*, 14:748-755, 2003.
Collier, *Soft Matter*, 4:2310-2315, 2008.
Daftarian et al., *Vaccine*, 24:5235-5244, 2006.
Davis et al., *Circulation*, 111:442-450, 2005.
Dubois et al., *J. Biomed. Mater. Res. B Appl. Biomater.*, 87:222-228, 2008.
Genove et al., *Biomaterials*, 26:3341-3351, 2005.
Gras et al., *Biomaterials*, 29:1553-1562, 2008.
Guler et al., *Biomacromolecules*, 7:1855-1863, 2006.
Hartgerink et al., *Science*, 294:1684-1688, 2001.
Holmes et al., *Proc. Natl. Acad. Sci. USA*, 97:6728-6733, 2000.
Horii et al., *PLoS ONE*: 2:e190, 2007.
Hsieh et al., *J. Clin. Invest.*, 116:237-248, 2006.
Ishii and Akira, *J. Clin. Immunol.*, 27:363-371, 2007.
Jung et al., *Biomaterials*, 29:2143-2151, 2008.
Jung et al., *Biomaterials*, 30:2400-2410, 2009.
Lambrecht et al., *Curr. Opin. Immunol.*, 21:23-29, 2009.
Lutolf and Hubbell, *Nat. Biotechnol.*, 23:47-55, 2005.
Maraskovsky et al., *Immunol. Cell Biol.*, 87:371-376, 2009.
Marrack et al., *Nat. Rev. Immunol.*, 9:287-293, 2009.
McKee et al., *Immunity*, 27:687-690, 2007.
McSorley et al., *J. Immunol.*, 169:3914-3919, 2002.
Place et al., *Nat. Mater.*, 8:457-470, 2009.
Purcell et al., *Nat. Rev. Drug Discov.*, 6:404-414, 2007.
*Remington's Pharmaceutical Sciences*, 15th Ed., 1035-1038 and 1570-1580, 1990.
Riley et al., *Biotechnol. Bioeng.*, 103:241-251, 2009.
Schneider et al., *J. Am. Chem. Soc.*, 124:15030-15037, 2002.
Silva et al., *Science*, 303:1352-1355, 2004.
Sun et al., *Vaccine*, 27:1787-1796, 2009.
Toth et al., *Int. J. Pept. Res. Ther.*, 14:333-340, 2008.
Tysseling-Mattiace et al., *J. Neurosci.*, 28:3814-3823, 2008.
Wendorf et al., *J. Pharm. Sci.*, 95:2738-2750, 2006.
Yang and Mine, *Biochem. Biophys. Res. Commun.*, 378:203-208, 2009.
Zhou et al., *Biomaterials*, 30:2523-2530, 2009.
Rudra, J. S. et al., *Proc. Natl. Acad. Sci. U.S.A.*, 2010, 107, 622-7.
Egelman, E. H. et al., *Structure* 2015, 23, 280-289.
Pompano, R. R. et al., *Adv Healthc Mater* 2014, 3, 1898-908.
Choi, B. et al., *Brain Pathology* 2009.
Scott, A. et al., *Nat Rev Cancer* 2012, 12, 278-287.

SEQUENCES

SEQ ID NO: 1
bXXXb wherein X is independently any amino acid, and b is independently any positively charged amino acid.

SEQ ID NO: 2
RAYAR

SEQ ID NO: 3
KAYAK

SEQ ID NO: 4
RXXXR wherein X is any amino acid.

SEQ ID NO: 5
$Z_n$bXXXb$Z_m$ wherein b is independently any positively charged amino acid, Z is independently any amino acid, X is independently any amino acid, n is an integer from 0 to 20, and m is an integer from 0 to 20.

Coil29
SEQ ID NO: 6
QARILEADAEILRAYARILEAHAEILRAQ

SEQ ID NO: 7
QAKILEADAEILKAYAKILEAHAEILKAQ

Coil23
SEQ ID NO: 8
ADAEILRAYARILEAHAEILRAQ

SEQ ID NO: 9
$G_n$ wherein n is an integer from 1 to 10

SEQ ID NO: 10
SGSG

SEQ ID NO: 11
GSGS

SEQ ID NO: 12
SSSS

SEQ ID NO: 13
GGGS

SEQ ID NO: 14
GGC

SEQ ID NO: 15
$(GGC)_8$

SEQ ID NO: 16
$(G_4S)_3$

PEPvIII
SEQ ID NO: 17
LEEKKGNYVVTDH

PADRE
SEQ ID NO: 18
aKXVAAVVTLKAa where "X" is cyclohexylalanine, and "a" is D-alanine Linker-Coil29
SEQ ID NO: 19
SGSG QARILEADAEILRAYARILEAHAEILRAQ PEPvIII-linker-Coil29
SEQ ID NO: 20
LEEKKGNYVVTDHSGSGQARILEADAEILRAYARILEAHAEILRAQ PADRE-linker-Coil29
SEQ ID NO: 21
aKXVAAVVTLKAaSGSGQARILEADAEILRAYARILEAHAEILRAQ OVA epitope
SEQ ID NO: 22
ISQAVHAAHAEINEAGR

SEQ ID NO: 23
SIINFEKL

SEQ ID NO: 24
AAYGG

What is claimed is:

1. An immunogenic composition comprising a peptide fibril coupled to a plurality of antigens, wherein the peptide fibril comprises a plurality of self-assembling peptides, wherein each self-assembling peptide forms an alpha-helix, and wherein the self-assembling peptide comprises an amino acid sequence of bXXXb (SEQ ID NO: 1), wherein X is independently any amino acid, and b is independently any positively charged amino acid.

2. The composition of claim 1, wherein the peptide fibril has a coiled coil structure.

3. The composition of claim 1, wherein the peptide fibril has a structure of a helical filament formed around a central axis.

4. The composition of claim 3, wherein the N-terminus of each self-assembling peptide is positioned at the exterior of the helical filament.

5. The composition of claim 1, wherein at least one self-assembling peptide is conjugated to an antigen.

6. The composition of claim 1, wherein the antigen is selected from a small molecule, nucleotide, polynucleotide, peptide, polypeptide, protein, lipid, carbohydrate, and a combination thereof.

7. The composition of claim 1, wherein the peptide fibril comprises self-assembling peptides not conjugated to the antigen and self-assembling peptides conjugated to the antigen, and wherein the peptide fibril comprises at least two different antigens.

8. The composition of claim 1, wherein bXXXb (SEQ ID NO: 1) is RAYAR (SEQ ID NO: 2) or KAYAK (SEQ ID NO: 3).

9. The composition of claim 1, wherein the self-assembling peptide comprises an amino acid sequence of $Z_n bXXXbZ_m$ (SEQ ID NO: 5), wherein b is independently any positively charged amino acid, Z is independently any amino acid, X is independently any amino acid, n is an integer from 0 to 20, and m is an integer from 0 to 20.

10. The composition of claim 1, wherein the self-assembling peptide comprises an amino acid sequence selected from QARILEADAEILRAYARILEAHAEILRAQ, (SEQ ID NO: 6)
or
QAKILEADAEILKAYAKILEAHAEILKAQ, (SEQ ID NO: 7)
or
ADAEILRAYARILEAHAEILRAQ. (SEQ ID NO: 8)

11. The composition of claim 1, wherein the self-assembling peptide further comprises a linker between the antigen and self-assembling peptide.

12. The composition of claim 11, wherein the linker comprises oligoethylene glycol, polyethylene glycol, or an amino acid sequence selected from SEQ ID NO: 9 ($G_n$, wherein n is an integer from 1 to 10), SEQ ID NO: 10 (SGSG), SEQ ID NO: 11 (GSGS), SEQ ID NO: 12 (SSSS), SEQ ID NO: 13 (GGGS), SEQ ID NO: 14 (GGC), SEQ ID NO: 15 ($(GGC)_8$), and SEQ ID NO: 16 ($(G_4S)_3$).

13. A method of inducing an antigen-specific immune response in a subject, the method comprising administering to the subject the immunogenic composition of claim 1 in an amount sufficient to induce an immune response and antigen-specific immunity.

14. An antibody produced in the immune response by the method of claim 13.

15. A method of treating a subject having or at risk of developing a microbial infection or pathological condition comprising administering to the subject an effective amount of a composition of claim 1.

16. A method for making the composition of claim 1, the method comprising: (i) providing a first peptide fibril comprising self-assembling peptides conjugated to a first antigen; providing a second peptide fibril comprising self-assembling peptides conjugated to a second antigen; and mixing together the first and the second peptide fibrils; or ii) providing a first peptide fibril comprising self-assembling peptides conjugated to an antigen; providing a second peptide fibril comprising self-assembling peptides not conjugated to an antigen; and mixing together the first and the second peptide fibrils; or (iii) providing a first peptide fibril comprising self-assembling peptides conjugated to a first antigen; providing a second peptide fibril comprising self-assembling peptides conjugated to a second antigen; providing a third peptide fibril comprising self-assembling peptides not conjugated to an antigen; and mixing together the first, the second, and the third peptide fibrils; or (iv) providing a first mixture comprising a plurality of self-assembling peptides, each self-assembling peptide conjugated to a first antigen; providing a second mixture comprising a plurality of self-assembling peptides, each self-assembling peptide conjugated to a second antigen; and mixing together the first mixture and the second mixture to form peptide fibrils, each peptide fibril comprising the first and second antigen; or (v) providing a first mixture comprising a plurality of self-assembling peptides conjugated to an antigen; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen; or (vi) providing a first mixture comprising a plurality of self-assembling peptides conjugated to a first antigen; providing a second mixture comprising a plurality of self-assembling peptides conjugated to a second antigen; providing a third mixture comprising a plurality of self-assembling peptides not conjugated to an antigen; and mixing together the first, the second, and the third mixtures to form peptide fibrils, each peptide fibril comprising the first antigen, the second antigen, and a portion of the self-assembling peptides not conjugated to an antigen.

17. The method of claim 16, wherein the first and second antigens are different.

18. A method for making the composition of claim 1, the method comprising: providing a first mixture comprising a plurality of self-assembling peptides conjugated to one or more antigens; providing a second mixture comprising a plurality of self-assembling peptides not conjugated to an antigen; and mixing together the first mixture and the second mixture to form peptide fibrils, each peptide fibril comprising a portion of the self-assembling peptides conjugated to an antigen and a portion of the self-assembling peptides not conjugated to an antigen.

19. The method of claim 18, wherein the antigens are the same or different.

* * * * *

SEQUENCE LISTING

<160> NUMBER OF SEQ ID NOS: 24

<210> SEQ ID NO 1
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is any positively charged amino acid
      independent of Xaa at position 5
<220> FEATURE:
<221> NAME/KEY: misc_feature
<222> LOCATION: (2)..(4)
<223> OTHER INFORMATION: Xaa is independently any amino acid
<220> FEATURE:
<221> NAME/KEY: misc_feature
<222> LOCATION: (5)..(5)
<223> OTHER INFORMATION: Xaa is any positively charged amino acid
      independent of Xaa at position 1

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic

<400> SEQUENCE: 2

Arg Ala Tyr Ala Arg
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic

<400> SEQUENCE: 3

Lys Ala Tyr Ala Lys
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa is independently any amino acid

<400> SEQUENCE: 4

Arg Xaa Xaa Xaa Arg
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic

```
<220> FEATURE:
<221> NAME/KEY: misc_feature
<222> LOCATION: (1)..(1)
<223> OTHER INFORMATION: Xaa is 0 to 20 amino acids, each of which is
      independently any amino acid
<220> FEATURE:
<221> NAME/KEY: misc_feature
<222> LOCATION: (2)..(2)
<223> OTHER INFORMATION: Xaa is any positively charged amino acid
      independent of Xaa at position 6
<220> FEATURE:
<221> NAME/KEY: misc_feature
<222> LOCATION: (3)..(5)
<223> OTHER INFORMATION: Xaa is independently any amino acid
<220> FEATURE:
<221> NAME/KEY: misc_feature
<222> LOCATION: (6)..(6)
<223> OTHER INFORMATION: Xaa is any positively charged amino acid
      independent of Xaa at position 2
<220> FEATURE:
<221> NAME/KEY: misc_feature
<222> LOCATION: (7)..(7)
<223> OTHER INFORMATION: Xaa is 0 to 20 amino acids, each of which is
      independently any amino acid

<400> SEQUENCE: 5

Xaa Xaa Xaa Xaa Xaa Xaa Xaa
1               5

<210> SEQ ID NO 6
<211> LENGTH: 29
<212> TYPE: PRT
<213> ORGANISM: Artificial sequence
<220> FEATURE:
<223> OTHER INFORMATION: Synthetic

<400> SEQUENCE: 6

Gln Ala Arg Ile Leu Glu Ala Asp Ala Glu Ile Leu Arg Ala Tyr Ala
1               5                   10                  15

Arg Ile Leu Glu Ala His Ala Glu Ile Leu Arg Ala Gln
            20                  25

<210> SEQ ID NO 7
<211> LENGTH: 29
<212> TYPE: PRT
<213> ORGANISM: Artificial sequence
<220> FEATURE:
<223> OTHER INFORMATION: Synthetic

<400> SEQUENCE: 7

Gln Ala Lys Ile Leu Glu Ala Asp Ala Glu Ile Leu Lys Ala Tyr Ala
1               5                   10                  15

Lys Ile Leu Glu Ala His Ala Glu Ile Leu Lys Ala Gln
            20                  25

<210> SEQ ID NO 8
<211> LENGTH: 23
<212> TYPE: PRT
<213> ORGANISM: Artificial sequence
<220> FEATURE:
<223> OTHER INFORMATION: Synthetic

<400> SEQUENCE: 8

Ala Asp Ala Glu Ile Leu Arg Ala Tyr Ala Arg Ile Leu Glu Ala His
1               5                   10                  15

Ala Glu Ile Leu Arg Ala Gln
            20
```

```
<210> SEQ ID NO 9
<211> LENGTH: 1
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is 1 to 10 glycine residues

<400> SEQUENCE: 9

Xaa
1

<210> SEQ ID NO 10
<211> LENGTH: 4
<212> TYPE: PRT
<213> ORGANISM: Artificial sequence
<220> FEATURE:
<223> OTHER INFORMATION: Synthetic

<400> SEQUENCE: 10

Ser Gly Ser Gly
1

<210> SEQ ID NO 11
<211> LENGTH: 4
<212> TYPE: PRT
<213> ORGANISM: Artificial sequence
<220> FEATURE:
<223> OTHER INFORMATION: Synthetic

<400> SEQUENCE: 11

Gly Ser Gly Ser
1

<210> SEQ ID NO 12
<211> LENGTH: 4
<212> TYPE: PRT
<213> ORGANISM: Artificial sequence
<220> FEATURE:
<223> OTHER INFORMATION: Synthetic

<400> SEQUENCE: 12

Ser Ser Ser Ser
1

<210> SEQ ID NO 13
<211> LENGTH: 4
<212> TYPE: PRT
<213> ORGANISM: Artificial sequence
<220> FEATURE:
<223> OTHER INFORMATION: Synthetic

<400> SEQUENCE: 13

Gly Gly Gly Ser
1

<210> SEQ ID NO 14
<211> LENGTH: 3
<212> TYPE: PRT
<213> ORGANISM: Artificial sequence
<220> FEATURE:
<223> OTHER INFORMATION: Synthetic
```

```
<400> SEQUENCE: 14

Gly Gly Cys
1

<210> SEQ ID NO 15
<211> LENGTH: 24
<212> TYPE: PRT
<213> ORGANISM: Artificial sequence
<220> FEATURE:
<223> OTHER INFORMATION: Synthetic

<400> SEQUENCE: 15

Gly Gly Cys Gly Gly Cys Gly Gly Cys Gly Gly Cys Gly Gly Cys Gly
1               5                   10                  15

Gly Cys Gly Gly Cys Gly Gly Cys
            20

<210> SEQ ID NO 16
<211> LENGTH: 15
<212> TYPE: PRT
<213> ORGANISM: Artificial sequence
<220> FEATURE:
<223> OTHER INFORMATION: Synthetic

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 13
<212> TYPE: PRT
<213> ORGANISM: Artificial sequence
<220> FEATURE:
<223> OTHER INFORMATION: Synthetic

<400> SEQUENCE: 17

Leu Glu Glu Lys Lys Gly Asn Tyr Val Val Thr Asp His
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is D-alanine
<220> FEATURE:
<221> NAME/KEY: misc_feature
<222> LOCATION: (3)..(3)
<223> OTHER INFORMATION: Xaa is cyclohexylalanine
<220> FEATURE:
<221> NAME/KEY: misc_feature
<222> LOCATION: (12)..(12)
<223> OTHER INFORMATION: Xaa is D-alanine

<400> SEQUENCE: 18

Xaa Lys Xaa Val Ala Ala Trp Thr Leu Lys Ala Xaa
1               5                   10

<210> SEQ ID NO 19
<211> LENGTH: 33
<212> TYPE: PRT
<213> ORGANISM: Artificial sequence
<220> FEATURE:
<223> OTHER INFORMATION: Synthetic
```

<400> SEQUENCE: 19

Ser Gly Ser Gly Gln Ala Arg Ile Leu Glu Ala Asp Ala Glu Ile Leu
1               5                   10                  15

Arg Ala Tyr Ala Arg Ile Leu Glu Ala His Ala Glu Ile Leu Arg Ala
            20                  25                  30

Gln

<210> SEQ ID NO 20
<211> LENGTH: 46
<212> TYPE: PRT
<213> ORGANISM: Artificial sequence
<220> FEATURE:
<223> OTHER INFORMATION: Synthetic

<400> SEQUENCE: 20

Leu Glu Glu Lys Lys Gly Asn Tyr Val Val Thr Asp His Ser Gly Ser
1               5                   10                  15

Gly Gln Ala Arg Ile Leu Glu Ala Asp Ala Glu Ile Leu Arg Ala Tyr
            20                  25                  30

Ala Arg Ile Leu Glu Ala His Ala Glu Ile Leu Arg Ala Gln
        35                  40                  45

<210> SEQ ID NO 21
<211> LENGTH: 45
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is D-alanine
<220> FEATURE:
<221> NAME/KEY: misc_feature
<222> LOCATION: (3)..(3)
<223> OTHER INFORMATION: Xaa is cyclohexylalanine
<220> FEATURE:
<221> NAME/KEY: misc_feature
<222> LOCATION: (12)..(12)
<223> OTHER INFORMATION: Xaa is D-alanine

<400> SEQUENCE: 21

Xaa Lys Xaa Val Ala Ala Trp Thr Leu Lys Ala Xaa Ser Gly Ser Gly
1               5                   10                  15

Gln Ala Arg Ile Leu Glu Ala Asp Ala Glu Ile Leu Arg Ala Tyr Ala
            20                  25                  30

Arg Ile Leu Glu Ala His Ala Glu Ile Leu Arg Ala Gln
        35                  40                  45

<210> SEQ ID NO 22
<211> LENGTH: 17
<212> TYPE: PRT
<213> ORGANISM: Artificial sequence
<220> FEATURE:
<223> OTHER INFORMATION: Synthetic

<400> SEQUENCE: 22

Ile Ser Gln Ala Val His Ala Ala His Ala Glu Ile Asn Glu Ala Gly
1               5                   10                  15

Arg

```
<210> SEQ ID NO 23
<211> LENGTH: 8
<212> TYPE: PRT
<213> ORGANISM: Artificial sequence
<220> FEATURE:
<223> OTHER INFORMATION: Synthetic

<400> SEQUENCE: 23

Ser Ile Ile Asn Phe Glu Lys Leu
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic

<400> SEQUENCE: 24

Ala Ala Tyr Gly Gly
1               5
```